United States Patent
Cid-Núñez et al.

(10) Patent No.: US 8,415,347 B2
(45) Date of Patent: Apr. 9, 2013

(54) SUBSTITUTED TETRACYCLIC TETAHYDROFURAN, PYRROLIDINE AND TETRAHYDROTHIOPHENE DERIVATIVES

(75) Inventors: José Maria Cid-Núñez, Toledo (ES); Antonius Adrianus Hendrikus Petrus Megens, Beerse (BE); Andrés Avelino Trabanco-Suárez, Toledo (ES); Mohamed Koukni, Leuven (BE); Georges Joseph Cornelius Hoornaert, Kessel-Lo (BE); Frans Josef Cornelius Compernolle, Herent (BE); Tomasz Kozlecki, Wroclaw (PL); Hua Mao, Fayetteville, AR (US); Sushil Chandra Jha, Hull (GB); Francisco Javier Fernández-Gadea, Toledo (ES)

(73) Assignee: Janssen Pharmaceutica, NV (BE)

( * ) Notice: Subject to any disclaimer, the term of this patent is extended or adjusted under 35 U.S.C. 154(b) by 30 days.

(21) Appl. No.: 12/850,958

(22) Filed: Aug. 5, 2010

(65) Prior Publication Data
US 2010/0331325 A1 Dec. 30, 2010

Related U.S. Application Data

(62) Division of application No. 11/815,726, filed as application No. PCT/EP2005/056544 on Dec. 6, 2005, now Pat. No. 7,799,785.

(51) Int. Cl.
| A61K 31/5377 | (2006.01) |
| A61K 31/403 | (2006.01) |
| A61K 31/496 | (2006.01) |
| A61K 31/381 | (2006.01) |
| A61K 31/4985 | (2006.01) |
| A61K 31/352 | (2006.01) |
| A61K 31/435 | (2006.01) |
| C07D 491/044 | (2006.01) |
| C07D 209/58 | (2006.01) |
| C07D 413/04 | (2006.01) |
| C07D 333/80 | (2006.01) |
| C07D 487/04 | (2006.01) |

(52) U.S. Cl. ............... 514/232.8; 514/410; 514/254.08; 514/443; 514/250; 514/453; 514/284; 544/372; 544/142; 544/342; 548/426; 548/418; 549/42; 549/383; 546/77

(58) Field of Classification Search .................. None
See application file for complete search history.

(56) References Cited

U.S. PATENT DOCUMENTS
7,799,785 B2 9/2010 CID-Nunez et al.
2009/0023721 A1 1/2009 Megens et al.

FOREIGN PATENT DOCUMENTS
| WO | WO 97/38991 A | 10/1997 |
| WO | WO 99/19317 A | 4/1999 |
| WO | 03/040122 | 5/2003 |
| WO | 03/048146 | 6/2003 |
| WO | 03/048147 | 6/2003 |

OTHER PUBLICATIONS

Ueda et al., Chemical & Pharmaceutical Bulletin (1978), vol. 26(10), p. 3058-3070.*
Gad et al., Phosphorus, Sulfur and Silicon and the Related Elements (1992), 66(1-4), 183-6, Abstract.
Mao, H et al: "Diastereoselective synthesis of trans-fused tetrahydropyran derivatives of 5H-dibenzo [a,d]cycloheptene" Tetrahedron Letters, Elsevier, Amsterdam, NL, vol. 43, No. 48, Nov. 25, 2002, pp. 8697-8700.
Meert et al., Drug Dev. Res., 13, 237-244 (1988).
Stella et al., Drugs, 1985, 29, pp. 455-473.
Stella, V. J. et al., "Prodrugs", *Drug Delivery Systems*, 1980, pp. 112-176.
Textbook of Organic Medicinal and Pharmaceutical Chemistry, 1977, pp. 70-75.
Thornber C.W.: "Isosterism and Molecular Modification in Drug Design" Chemical Society Reviews, Chemical Society, London, GB, vol. 8, No. 4, 1979, pp. 563-580.

* cited by examiner

Primary Examiner — Yong Chu

(57) ABSTRACT

This invention concerns novel substituted tetracyclic tetrahydrofuran, pyrrolidine and tetrahydrothiophene derivatives with binding affinities towards serotonin receptors, in particular 5-$HT_{2A}$ and 5-$HT_{2C}$ receptors, and towards dopamine receptors, in particular dopamine D2 receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

The compounds according to the invention can be represented by general Formula (I)

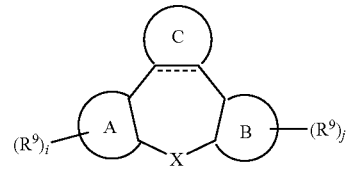

and comprises also the pharmaceutically acceptable acid or base addition salts thereof, the stereochemically isomeric forms thereof, the N-oxide form thereof and prodrugs thereof, wherein all substituents are defined as in Claim 1.

9 Claims, No Drawings

SUBSTITUTED TETRACYCLIC TETAHYDROFURAN, PYRROLIDINE AND TETRAHYDROTHIOPHENE DERIVATIVES

CROSS REFERENCE TO RELATED APPLICATIONS

This divisional application claims the benefit of parent application Ser. No. 11/815,726, filed 7 Aug. 2007, now U.S. Pat. No. 7,799,785 which is the national stage of Application No. PCT/EP2005/056544, filed 6 Dec. 2005, which application claims priority from PCT/EP04106373.6 filed 7 Dec. 2004.

FIELD OF THE INVENTION

This invention concerns novel substituted tetracyclic tetrahydrofuran, pyrrolidine and tetrahydrothiophene derivatives with binding affinities towards serotonin receptors, in particular 5-$HT_{2A}$ and 5-$HT_{2C}$ receptors, and towards dopamine receptors, in particular dopamine D2 receptors and with norepinephrine reuptake inhibition properties, pharmaceutical compositions comprising the compounds according to the invention, the use thereof as a medicine, in particular for the prevention and/or treatment of a range of psychiatric and neurological disorders, in particular certain psychotic, cardiovascular and gastrokinetic disorders and processes for their production.

BACKGROUND PRIOR ART

WO 97/38991, published Oct. 23, 1997 (Janssen Pharmaceutica N.V.) discloses substituted tetracyclic tetrahydrofuran derivatives that may be used as therapeutic agents in the treatment or prevention of CNS disorders, cardiovascular disorders or gastrointestinal disorders. In particular, the compounds show affinity for the serotonin 5-$HT_2$ receptors, particularly for the 5-$HT_{2A}$ and 5-$HT_{2C}$-receptors.

WO 99/19317, published Apr. 22, 1999 (Janssen Pharmaceutica N.V.) discloses substituted tetracyclic tetrahydrofuran derivatives with a specific halogen substitution pattern on the dibenzoazepine, dibenzooxepine, dibenzothiepine or dibenzosuberane ring. The compounds are useful in the treatment or prevention of CNS disorders, cardiovascular disorders or gastrointestinal disorders and show a faster onset of action over the compounds as disclosed in WO 97/38991.

Both WO 03/048146, published Jun. 12, 2003 (Janssen Pharmaceutica N.V.) and WO 03/048147, published Jun. 12, 2003 (Janssen Pharmaceutica N.V.) disclose processes for the preparation of each of the 4 diastereomers of cis-, respectively trans-fused 3,3a,8,12b-tetrahydro-2H-dibenzo[3,4:6,7]cyclohepta[1,2-b]furan derivatives in a stereochemically pure form from a single enantiomerically pure precursor. The compounds show affinity for the serotonin 5-$HT_{2A}$, 5-$HT_{2C}$ and 5-$HT_7$ receptors and the $H_1$-receptors ($pIC_{50}$=7.15-7.89), D2 and/or D3 receptors and for the norepinephrine reuptake transporters ($pIC_{50}$=6.01-7.34).

WO 03/040122, published May 15, 2003 (Janssen Pharmaceutica N.V.) discloses mandelate salts of the compounds according to WO 97/38991 and WO 99/19317. Said salts were surprisingly found to be more stable at enhanced temperature and relative humidity than the compounds disclosed in WO 97/38991 and WO 99/19317.

DESCRIPTION OF THE INVENTION

It is the object of the present invention to provide novel analogues of the tetracyclic tetrahydrofuran derivatives of WO 97/38991 and WO 99/19317, which differ from such derivatives in that they demonstrate in general more selectivity for the norepinephrine reuptake transporter than the 5-$HT_{2A}$, 5-$HT_{2C}$ and dopamine $D_2$ receptors, resulting in compounds which have a more pronounced antidepressant effect in relation to their antipsychotic properties. The compounds of formula (I) below where the basic nitrogen atom at the C-2 position is embedded in a cyclic system demonstrate a potent antagonistic effect against the 5-$HT_{2A}$, 5-$HT_{2C}$ and dopamine $D_2$ receptors.

This goal is achieved by the present novel compounds according to Formula (I):

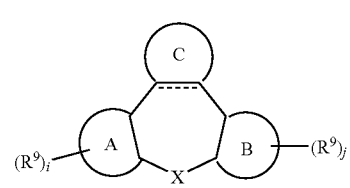

(I)

an N-oxide form, a pharmaceutically acceptable addition salt or a stereochemically isomeric form thereof, wherein:

the dotted line represents an optional bond;

i and j are integers, independently from each other, equal to zero, 1, 2, 3 or 4;

A and B are, each independently from each other, benzo, naphtho or a radical selected from the group of furo; thieno; pyrrolo; oxazolo; thiazolo; imidazolo; isoxazolo; isothiazolo; oxadiazolo; triazolo; pyridino; pyridazino; pyrimidino; pyrazino; indolo; indolizino; isoindolo; benzofuro; isobenzofuro; benzothieno; indazolo; benzimidazolo; benzthiazolo; quinolizino; quinolino; isoquinolino; phthalazino; quinazolino; quinoxalino; chromeno and naphthyridino;

each $R^9$ is, independently from each other, selected from the group of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkyloxy; alkylcarbonyl and alkyloxycarbonyl;

X represents $CR^6R^7$, O, S, S(=O), S(=O)$_2$ or $NR^8$; wherein:

$R^6$ and $R^7$ each independently are selected from the group of hydrogen, hydroxy, alkyl and alkyloxy; or $R^6$ and $R^7$ taken together may form a radical selected from the group of methylene (=$CH_2$); mono- or di(cyano)methylene; a bivalent radical of formula —($CH_2$)$_2$—, —($CH_2$)$_3$—, —($CH_2$)$_4$—, —($CH_2$)$_5$—, —O($CH_2$)$_2$O—, —O($CH_2$)$_3$O—; or together with the carbon atom to which they are attached, a carbonyl;

$R^8$ is selected from the group of hydrogen; alkyl; alkylcarbonyl; arylcarbonyl; arylalkyl; arylalkylcarbonyl; alkylsulfonyl; arylsulfonyl and arylalkylsulfonyl;

C is a group of formula (c-1), (c-2), (c-3) or (c-4);

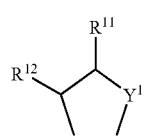

(c-1)

-continued

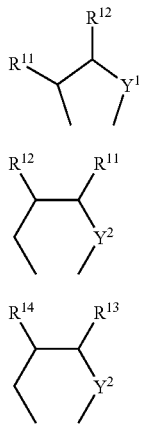
(c-2)

(c-3)

(c-4)

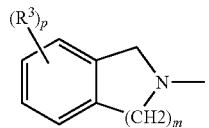
(a-1)

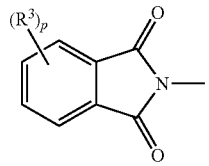
(a-2)

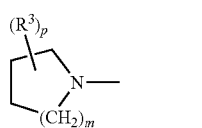
(a-3)

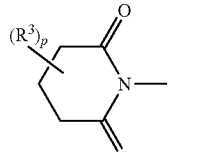
(a-4)

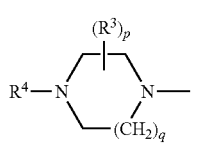
(a-5)

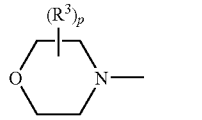
(a-6)

wherein:
$Y^1$ is S; S(=O); S(=O)$_2$ or NR$^{10}$; wherein R$^{10}$ is selected from the group of hydrogen, cyano, alkyl, alkyloxyalkyl, formyl, alkylcarbonyl, alkyloxycarbonyl, alkyloxyalkylcarbonyl, arylcarbonyl, arylalkyl, arylalkylcarbonyl, alkylsulfonyl, arylsulfonyl and arylalkylsulfonyl;
$Y^2$ is $Y^1$ or O;
$R^{10}$ and $R^{11}$ may form together a bivalent radical (e-1), (e-2) or (e-3);

—CH$_2$—NH—CH$_2$— (e-1)

—CH$_2$—NH—CH$_2$—CH$_2$— (e-2)

—CH$_2$CH$_2$—NH—CH$_2$— (e-3)

each bivalent radical (e-1), (e-2) and (e-3) optionally substituted by one or more substituents selected from oxo, thioxo, alkyl and alkylthio;
$R^{12}$ is hydrogen or alkyl;
$R^{13}$ is hydrogen or alkyl;
$R^{14}$ is hydrogen, hydroxy, oxo or a group of formula (d-1)
$R^{11}$ is a group of formula (d-1);

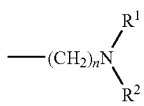
(d-1)

wherein:
n is zero, 1, 2, 3, 4, 5 or 6;
$R^1$ and $R^2$ each independently are hydrogen; alkyl; alkylcarbonyl; alkyloxyalkyl; alkylcarbonyloxyalkyl; alkyloxycarbonylalkyl; arylalkyl; arylcarbonyl; alkyloxycarbonyl; aryloxycarbonyl; arylalkylcarbonyl; alkyloxycarbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl; arylalkylsulphonyl; mono- or di(alkyl)aminothiocarbonyl; mono- or di(aryl)aminothiocarbonyl; mono- or di(arylalkyl)aminothiocarbonyl; mono-, di- or tri(alkyl)-amidino; mono-, di- or tri(aryl)amidino and mono-, di- or tri(arylalkyl)amidino; or
$R^1$ and $R^2$ taken together with the nitrogen atom to which they are attached may form a radical of formula (a-1), (a-2), (a-3), (a-4), (a-5) or (a-6);

wherein:
P is zero, 1, 2, 3 or 4;
q is 1 or 2;
m is zero, 1, 2, or 3;
each R$^3$ independently is selected from the group of hydrogen; halo; hydroxy; cyano; alkyl; alkyloxyalkyl; aryloxyalkyl; mono- or di(alkyl)aminoalkyl; hydroxycarbonylalkyl; alkyloxycarbonylalkyl; mono- or di(alkyl)aminocarbonylalkyl; mono- or di(aryl)aminocarbonylalkyl; mono- or di(alkyl)aminocarbonyloxyalkyl; alkyloxycarbonyloxyalkyl; arylaminocarbonyloxyalkyl; arylalkylaminocarbonyloxyalkyl; aryl; alkyloxy; aryloxy; alkylcarbonyloxy; arylcarbonyloxy; arylalkylcarbonyloxy; alkylcarbonyl; arylcarbonyl; aryloxycarbonyl; hydroxycarbonyl; alkyloxycarbonyl; alkylcarbonylamino; arylalkylcarbonylamino; arylcarbonylamino; alkyloxycarbonylamino; aminocarbonylamino; mono- or di(arylalkyl)aminocarbonylamino; alkylsulphonylalkylaminocarbonylamino; or two R$^3$-radicals may form together a bivalent radical —CR$^5$R$^5$—CR$^5$R$^5$—O— (b-1)

—O—CR$^5$R$^5$—CR$^5$R$^5$— (b-2)

—O—CR$^5$R$^5$—CR$^5$R$^5$—O— (b-3)

—O—CR$^5$R$^5$—CR$^5$R$^5$—CR$^5$R$^5$— (b-4)

—CR$^5$R$^5$—CR$^5$R$^5$—CR$^5$R$^5$—O— (b-5)

$$-O-CR^5R^5-CR^5R^5-CR^5R^5-O- \quad (b-6)$$

$$-O-CR^5R^5CR^5R^5CR^5R^5CR^5R^5- \quad (b-7)$$

$$CR^5R^5CR^5R^5CR^5R^5CR^5R^5-O- \quad (b-8)$$

$$-O-CR^5R^5-CR^5R^5-CR^5R^5-O- \quad (b-9)$$

wherein $R^5$ is selected from the group of hydrogen, halo, hydroxy, alkyloxy and alkyl;

$R^4$ is selected from the group of hydrogen; alkyl; arylalkyl; alkyloxyalkyl; alkylcarbonyloxyalkyl; alkyloxycarbonylalkyl; arylcarbonylalkyl; alkylsulphonyloxyalkyl; aryloxyaryl; alkyloxycarbonylaryl; alkylcarbonyl; arylalkylcarbonyl; alkyloxycarbonylalkylcarbonyl; arylcarbonyl; alkyloxycarbonyl; aryloxycarbonyl; arylalkyloxycarbonyl; mono- or di(alkyl)-aminocarbonyl; mono- or di(aryl)aminocarbonyl; mono- or di(arylalkyl) aminocarbonyl; mono- or di(alkyloxycarbonylalkyl) aminocarbonyl; alkyloxyalkylaminocarbonyl; mono-, di- or tri(alkyl)amidino; mono-, di- or tri(aryl)amidino; mono-, di- or tri(arylalkyl)amidino; alkylsulphonyl; arylalkylsulphonyl or arylsulphonyl;

aryl is phenyl or naphthyl; each radical optionally substituted with 1, 2 or 3 substituents selected from the group of halo, nitro, cyano, hydroxy, alkyloxy or alkyl;

alkyl represents a straight or branched saturated hydrocarbon radical having from 1 to 10 carbon atoms, a cyclic saturated hydrocarbon radical having from 3 to 8 carbon atoms or a saturated hydrocarbon radical containing a straight or branched moiety having from 1 to 10 carbon atoms and a cyclic moiety having from 3 to 8 carbon atoms, optionally substituted with one or more halo, cyano, oxo, hydroxy, formyl, carboxyl or amino radicals; and halo represents fluoro, chloro, bromo and iodo.

More in particular, the invention relates to a compound according to Formula (I), the pharmaceutically acceptable acid or base addition salts thereof, the stereochemically isomeric forms thereof, the N-oxide form thereof and a prodrug thereof, wherein A and B are each benzo, optionally substituted with fluoro. Preferably, A is unsubstituted and B is substituted with fluoro at the 11-position.

More in particular, the invention relates to a compound according to Formula (I), the pharmaceutically acceptable acid or base addition salts thereof, the stereochemically isomeric forms thereof, the N-oxide form thereof and a prodrug thereof, wherein C is a group of formula (c-1) or (c-2); wherein $Y^1$ is S; S(=O); S(=O)$_2$ or NR$^{10}$; wherein R$^{10}$ is selected from the group of hydrogen, cyano, alkyl, alkyloxyalkyl, formyl, alkylcarbonyl, alkyloxycarbonyl and alkyloxyalkylcarbonyl;

adjacent $R^{10}$ and $R^{11}$ may form together a bivalent radical (e-1), (e-2) or (e-3); each radical optionally substituted by one or more substituents selected from oxo, thioxo, alkyl and alkylthio; and $R^{12}$ is hydrogen.

More in particular, the invention relates to a compound according to Formula (I), the pharmaceutically acceptable acid or base addition salts thereof, the stereochemically isomeric forms thereof, the N-oxide form thereof and a prodrug thereof, wherein C is a group of formula (c-3) or (c-4); wherein $Y^2$ is O;

$R^{12}$ is hydrogen;

$R^{13}$ is hydrogen; and $R^{14}$ is hydrogen, hydroxy, oxo or a group of formula (d-1).

More in particular, the invention relates to a compound according to Formula (I), the pharmaceutically acceptable acid or base addition salts thereof, the stereochemically isomeric forms thereof, the N-oxide form thereof and a prodrug thereof, wherein (d-1) is defined as wherein:

n is zero or 1;

$R^1$ and $R^2$ each independently are hydrogen; alkyl or alkyloxycarbonylalkyl; or $R^1$ and $R^2$ taken together with the nitrogen atom to which they are attached may form a radical of formula (a-3), (a-5) or (a-6); wherein:

p is zero or 1;

q is 1;

m is 1;

each $R^3$ independently is selected from the group of hydrogen and hydroxy; and $R^4$ is alkyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:

i and j are integers, independently from each other, equal to zero or 1;

A and B are, each independently from each other, benzo, optionally substituted with fluoro;

each $R^9$ is, independently from each other, selected from the group of hydrogen and halo;

X represents CH$_2$ and O;

C is a group of formula (c-1), (c-2), (c-3) or (c-4); wherein $Y^1$ is S; S(=O); S(=O)$_2$ or NR$^{10}$; wherein R$^{10}$ is selected from the group of hydrogen, cyano, alkyl, alkyloxyalkyl, formyl, alkylcarbonyl, alkyloxycarbonyl and alkyloxyalkylcarbonyl;

$Y^2$ is O;

adjacent $R^{10}$ and $R^{11}$ may form together a bivalent radical (e-1), (e-2) or (e-3); each radical optionally substituted by one or more substituents selected from oxo, thioxo, alkyl and alkylthio;

$R^{12}$ is hydrogen;

$R^{13}$ is hydrogen;

$R^{14}$ is hydrogen, hydroxy, oxo or a group of formula (d-1)

$R^{11}$ is a group of formula (d-1); wherein:

n is zero or 1;

$R^1$ and $R^2$ each independently are hydrogen; alkyl or alkyloxycarbonylalkyl; or $R^1$ and $R^2$ taken together with the nitrogen atom to which they are attached may form a radical of formula (a-3), (a-5) or (a-6); wherein:

p is zero or 1;

q is 1;

m is 1;

each $R^3$ independently is selected from the group of hydrogen and hydroxy; and $R^4$ is alkyl.

Preferably, alkyl is methyl, ethyl or propyl, optionally substituted with one or more halo, cyano, oxo, hydroxy, formyl, carboxyl or amino radicals. Preferably, alkyl is optionally substituted with hydroxy.

Preferably, aryl is phenyl, optionally substituted with 1, 2 or 3 substituents selected from the group of halo, nitro, cyano, hydroxy, alkyloxy or alkyl. Preferably, aryl is unsubstituted.

Preferably, halo is fluoro.

Preferred compounds are also those particular compounds according to the invention wherein the hydrogen atoms on carbon atoms 3a and 12b have a trans configuration and those having the (2α,3aα,12bβ) stereochemical configuration.

Most preferred compounds are also those compounds according to the invention where the compounds are selected from the group of compounds defined by the compound numbers given in Tables 1 to 4.

DETAILED DESCRIPTION OF THE INVENTION

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl and hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluor is mentioned, it is understood to refer to $^{18}F$, $^{19}F$ and mixtures thereof.

The compounds according to the invention therefore also comprise compounds with one or more isotopes of one or more element, and mixtures thereof, including radioactive compounds, also called radiolabelled compound, wherein one or more non-radioactive atoms has been replaced by one of its radioactive isotopes. By the term "radiolabelled compound" is meant any compound according to Formula (I), an N-oxide form, a pharmaceutically acceptable addition salt or a stereochemically isomeric form thereof, which contains at least one radioactive atom. For example, compounds can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}$, all of which are accelerator produced and have half-lives of 20, 100, 2 and 10 minutes respectively.

Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or piperidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with much the same effects.

The compounds according to the invention possess at least 1 oxydizable nitrogen (tertiary amines moiety). It is therefore highly likely that N-oxides are to form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

The numbering of the tetracyclic ring-systems present in the compounds of Formula (I-a) and (I-b) when A and B are benzo, as defined by Chemical Abstracts nomenclature is shown below.

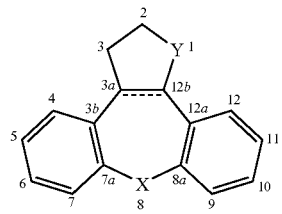

I-a

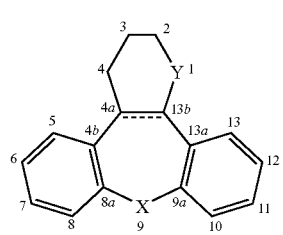

I-b

The compounds of Formula (I-a) and (I-b) have at least two asymmetric centers at respectively carbon atom 2 and 3. Said asymmetric center and any other asymmetric center, which may be present (e.g. at atom 8 in (I-a) or 9 in (I-b)), are indicated by the descriptors R and S. When e.g. a monocyanomethylene moiety is present in the compounds of Formula (I-a) at position 8, said moiety may have the E- or Z-configuration.

The invention also comprises derivative compounds (usually called "pro-drugs") of the pharmacologically active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Prodrugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the Formula —COOR$^x$, where R$^x$ is a C$_{1-6}$alkyl, phenyl, benzyl or one of the following groups:

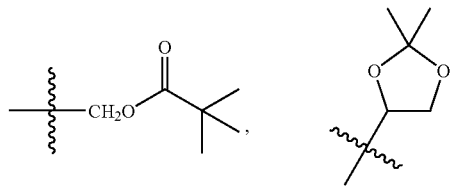

Amidated groups include groups of the Formula —CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

The compounds of the present invention show affinity for 5-HT$_2$ receptors, particularly for 5-HT$_{2A}$ and 5-HT$_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden) and affinity for the D2 receptor as well as norepinephrine reuptake inhibition activity. The serotonin antagonistic properties of the present compounds may be demonstrated by their inhibitory effect in the "5-hydroxytryptophan Test on Rats" which is described in Drug Dev. Res., 13, 237-244 (1988).

In view of their capability to block 5-HT$_2$ receptors, and in particular to block 5-HT$_{2A}$ and 5-HT$_{2C}$ receptors, as well as the D2 receptor and by also effecting the norepinephrine reuptake inhibition activity, the compounds according to the invention are useful as a medicine, in particular in the prophylactic and therapeutic treatment of conditions mediated through either of these receptors.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to the general Formula (I), the pharmaceutically acceptable acid or base addition salts thereof, the stereochemically isomeric forms thereof, the N-oxide form thereof and prodrugs thereof for the manufacture of a medicament for treating, either prophylactic or therapeutic or both, conditions mediated through the 5-HT$_2$, and D2 receptor, as well as the through norepinephrine reuptake inhibition.

In view of these pharmacological and physicochemical properties, the compounds of Formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children such as ADHD, aggression, memory disorders and attitude disorders in older people, addiction, obesity, bulimia and similar disorders. In particular, the present compounds may be used as anxiolytics, antidepressants, antipsychotics, anti-schizophrenia agents, antimigraine agents and as agents having the potential to overrule the addictive properties of drugs of abuse.

The compounds of Formula (I) may also be used as therapeutic agents in the treatment of motoric disorders. It may be advantageous to use the present compounds in combination with classical therapeutic agents for such disorders.

The compounds of Formula (I) may also serve in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like.

In view of the above uses of the compounds of Formula (I), it follows that the present invention also provides a method of treating warm-blooded animals suffering from such diseases, said method comprising the systemic administration of a therapeutic amount of a compound of Formula (I) effective in treating the above described disorders, in particular, in treating anxiety, psychosis, depression, migraine and addictive properties of drugs of abuse.

The present invention thus also relates to compounds of Formula (I) as defined hereinabove for use as a medicine, in particular, the compounds of Formula (I) may be used for the manufacture of a medicament for treating anxiety, psychosis, depression, migraine and addictive properties of drugs of abuse.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a prodrug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be Formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to Formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Preparation

Suitable preparation schemes for the compounds of the invention are described below:

The following abbreviations are used throughout the text:

| APCI | Atmospheric Pressure Chemical Ionization |
|---|---|
| AcOH | acetic acid |
| AcSH | thioacetic acid |
| Bu | n-butyl |
| Boc | t-butyloxycarbonyl |
| Cbz- | 4-carboxybenzoyl (e.g. CBzCl) |
| Celite ® | diatomaceous earth from Celite Corporation |
| CI | chemical ionization |
| CSA | camphorsulfonic acid |
| DBU | 1,8-diazabicyclo[5,4,0]undec-7-ene |
| DIAD | diisopropyl diazodicarboxylate |
| DMAP | 4-dimethylaminopyridine |
| DMF | N,N-dimethylformamide |
| DOWEX ® | ion exchange resin from the company DOW |
| DPPA | diphenyl phosphoryl azide |
| EEDQ | 2-ethoxy-1-ethoxycarbonyl-1,2-dihydroquinoline |
| EI | electron ionization |
| Et | ethyl |
| Et$_3$N | triethylamine |
| EtOH | ethanol |
| Et$_2$O | diethylether |
| EtOAc | ethyl acetate |
| HFIP | hexafluoroisopropanol |
| i-PrOH | isopropanol |
| IPy$_2$BF$_4$ | bis(pyridine)iodonium tetrafluoroborate |
| t-BuOK | potassium salt of 2-methyl-2-propanol |
| mCPBA | m-chloroperoxybenzoic acid |
| Me | methyl |
| MeOH | methanol |
| Ms | mesyl (e.g. MsCl) |
| PCC | pyridinium chlorochromate |
| PNBz | 4-nitrobenzoyl |
| P(Ph)$_3$ | triphenylphosphine |
| TFA | trifluoroacetic acid |
| THF | tetrahydrofuran |
| THP | tetrahydropyranyl |
| Tr | trityl (i.e. triphenylmethyl) (e.g. TrCl) |
| TsCl | tosyl (i.e. 4-toluenesulfonyl) chloride |

The following reaction schemes A to D illustrate the preparation of compounds of formula (I) in which C is a group of formula (c-1) in which Y$^1$ is NH and R$^{11}$ is a group of formula (d-1), represented by formulae Ia and Ib below:

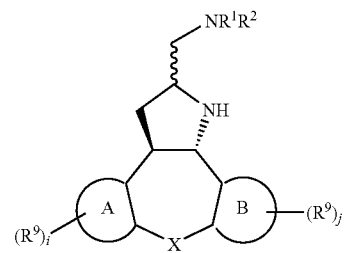

Ia: 2R,3aR,xS, wherein x is 12b if A and B are benzo
Ib: 2S,3aR,xS, wherein x is 12b if A and B are benzo Method A: Preparation of Pyrrolidine Derivatives Scheme A1: Synthesis of (2R, 3aR, 12bS)-intermediate compounds.

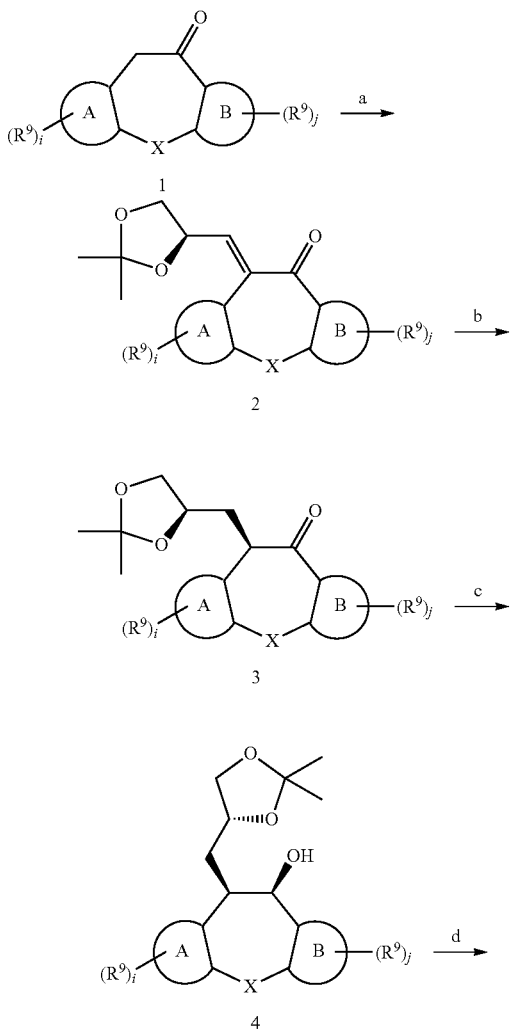

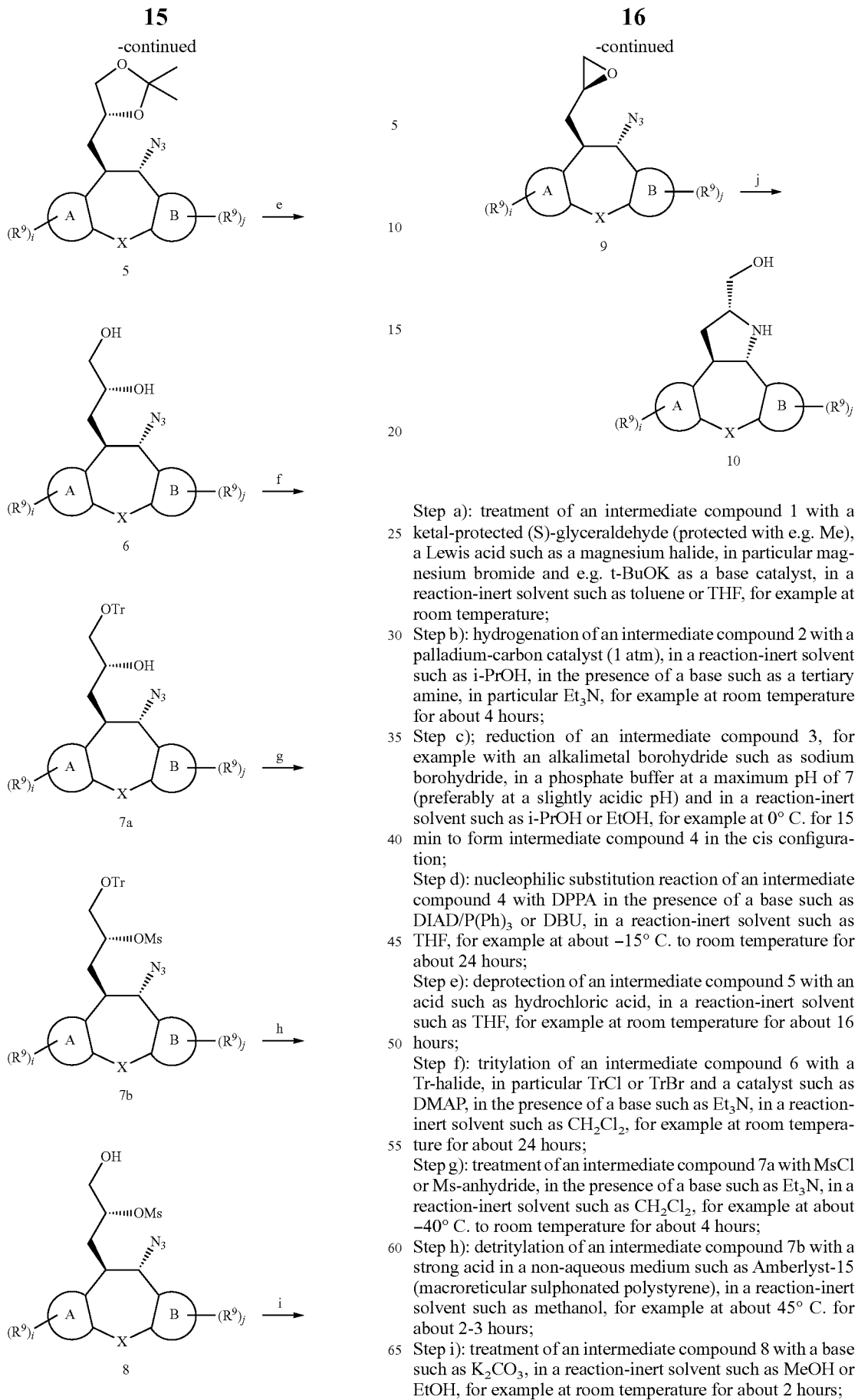

Step a): treatment of an intermediate compound 1 with a ketal-protected (S)-glyceraldehyde (protected with e.g. Me), a Lewis acid such as a magnesium halide, in particular magnesium bromide and e.g. t-BuOK as a base catalyst, in a reaction-inert solvent such as toluene or THF, for example at room temperature;

Step b): hydrogenation of an intermediate compound 2 with a palladium-carbon catalyst (1 atm), in a reaction-inert solvent such as i-PrOH, in the presence of a base such as a tertiary amine, in particular $Et_3N$, for example at room temperature for about 4 hours;

Step c): reduction of an intermediate compound 3, for example with an alkalimetal borohydride such as sodium borohydride, in a phosphate buffer at a maximum pH of 7 (preferably at a slightly acidic pH) and in a reaction-inert solvent such as i-PrOH or EtOH, for example at 0° C. for 15 min to form intermediate compound 4 in the cis configuration;

Step d): nucleophilic substitution reaction of an intermediate compound 4 with DPPA in the presence of a base such as $DIAD/P(Ph)_3$ or DBU, in a reaction-inert solvent such as THF, for example at about −15° C. to room temperature for about 24 hours;

Step e): deprotection of an intermediate compound 5 with an acid such as hydrochloric acid, in a reaction-inert solvent such as THF, for example at room temperature for about 16 hours;

Step f): tritylation of an intermediate compound 6 with a Tr-halide, in particular TrCl or TrBr and a catalyst such as DMAP, in the presence of a base such as $Et_3N$, in a reaction-inert solvent such as $CH_2Cl_2$, for example at room temperature for about 24 hours;

Step g): treatment of an intermediate compound 7a with MsCl or Ms-anhydride, in the presence of a base such as $Et_3N$, in a reaction-inert solvent such as $CH_2Cl_2$, for example at about −40° C. to room temperature for about 4 hours;

Step h): detritylation of an intermediate compound 7b with a strong acid in a non-aqueous medium such as Amberlyst-15 (macroreticular sulphonated polystyrene), in a reaction-inert solvent such as methanol, for example at about 45° C. for about 2-3 hours;

Step i): treatment of an intermediate compound 8 with a base such as $K_2CO_3$, in a reaction-inert solvent such as MeOH or EtOH, for example at room temperature for about 2 hours;

Step j): hydrogenation of an intermediate compound 9 with a palladium-carbon catalyst (1 atm) in a reaction-inert solvent such as MeOH, in the presence of a base such as Et₃N, for example at room temperature for about 3 hours. The resulting intermediate compound 10 may be used as a starting material as described in Scheme A3.

Step d): nucleophilic substitution of an intermediate compound 11 or 12 with an alkalimetal azide such sodium azide, in a reaction-inert solvent such as DMF, for example at about 90° C.;

Step e): mesylation of an intermediate compound 14 with MsCl and optionally DMAP, with a tertiary amine base such Scheme A2: Synthesis of (2S, 3aR, 12bS)-intermediate and final compounds.

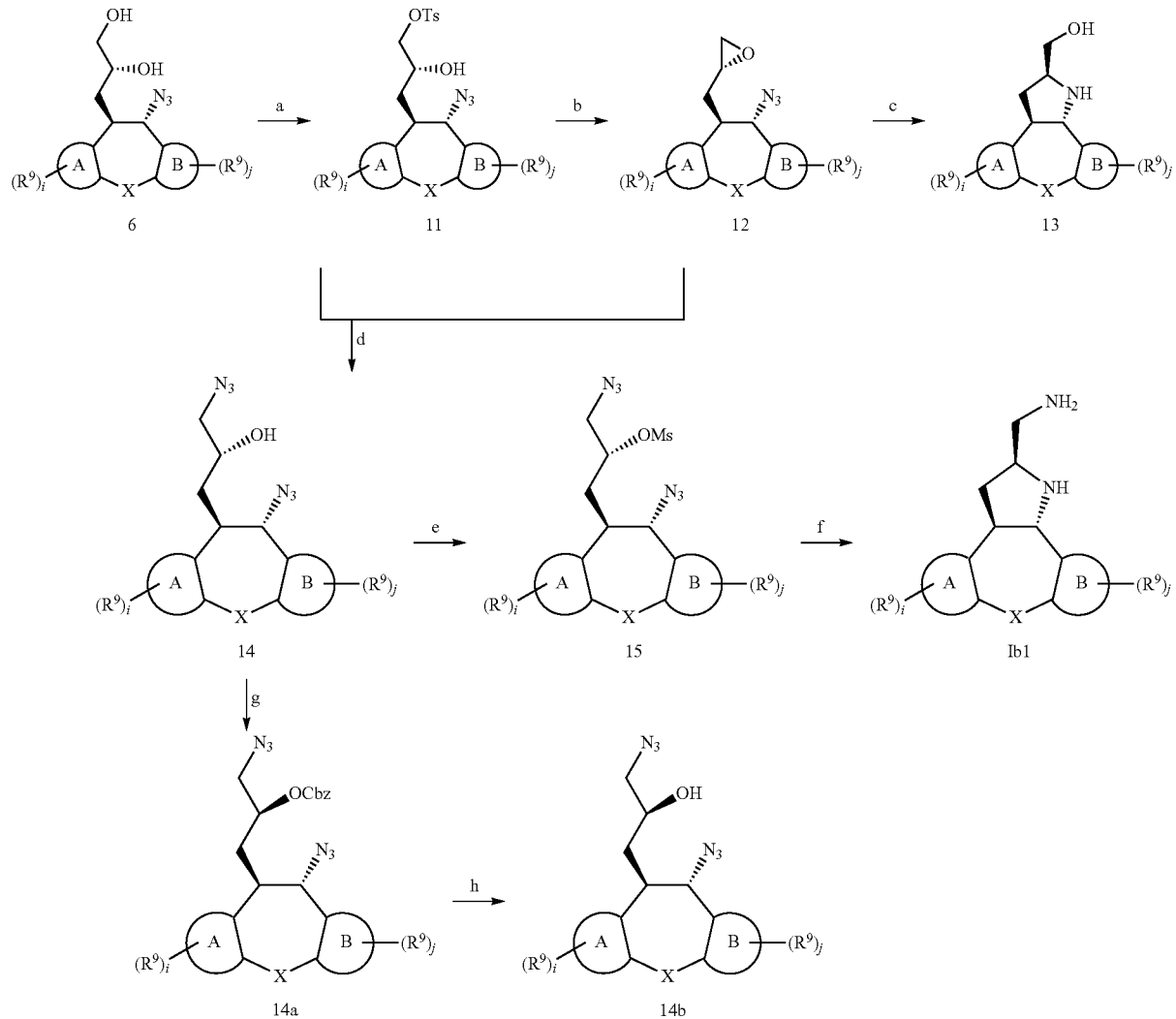

Step a): tosylation of an intermediate compound 6 with TsCl in the presence of a base such as Et₃N and a catalyst such as Bu₂SnO, in a reaction-inert solvent such as CH₂Cl₂, for example at room temperature for about 16 hours;

Step b): treatment of an intermediate compound 11 with a base such as K₂CO₃, in a reaction-inert solvent such as MeOH, for example at room temperature for about 10 minutes;

Step c): hydrogenation of an intermediate compound 12 with a palladium-carbon catalyst (1 atm), in a reaction-inert solvent such as MeOH, for example at room temperature for about 16 hours; The resulting compound 13 can be used as a starting material as described in Scheme A3.

as Et₃N in a reaction-inert solvent such as CH₂Cl₂, for example at about −40° C. to room temperature for about 4 hours;

Step f): hydrogenation of an intermediate compound 15 with a palladium-carbon catalyst (1 atm) with a base such as Et₃N, in a reaction-inert solvent such as MeOH, for example at room temperature for about 3 hours leads to a final compound of formula (I-b1), i.e. a compound of Formula (I-b) wherein $R^1$ and $R^2$ are both hydrogen.

Step g): Mitsonobu inversion of an intermediate compound 14 using DIAD/P(Ph)₃ and CbzOH in THF at about 0° C. to room temperature for about 2 hours;

Step h) hydrolysis of the intermediate compound 14a using for example K₂CO₃ in methanol.

Scheme A3: Synthesis of (2R, 3aR, 12bS)- and (2S, 3aR, 12bS)-final compounds

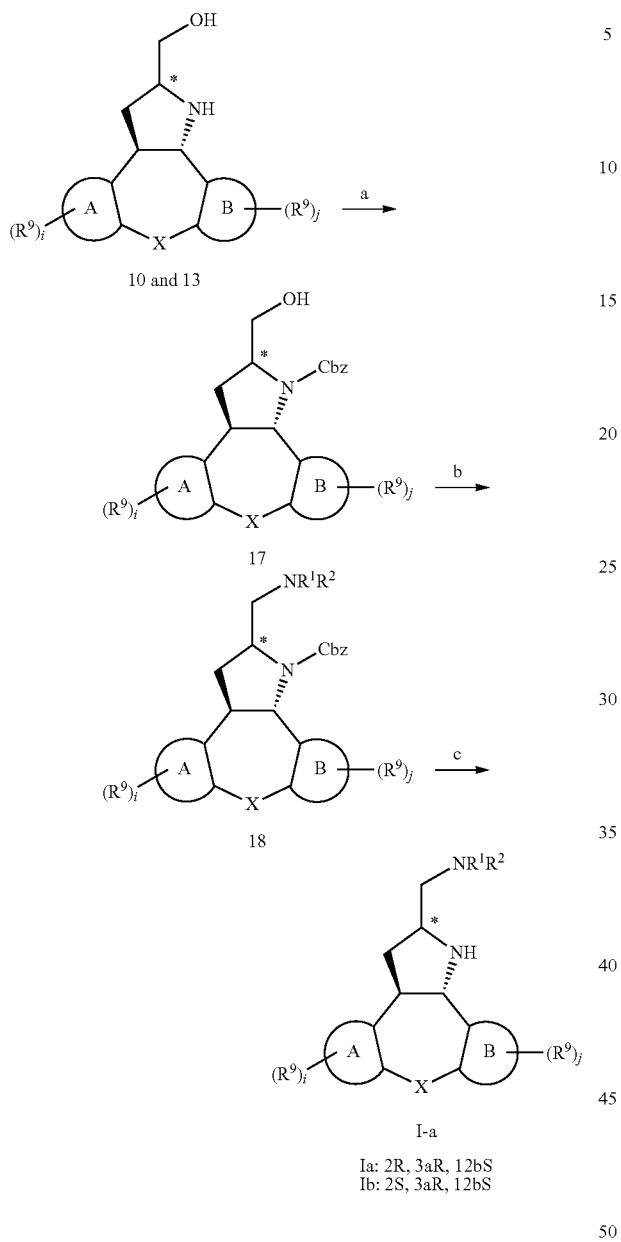

10 and 13

17

18

I-a

Ia: 2R, 3aR, 12bS
Ib: 2S, 3aR, 12bS

Step a) treatment of an intermediate compound 10 or 13 with CbzCl, with an aqueous solution of a base, such as $K_2CO_3$, in a reaction-inert solvent such as THF, for example at room temperature for 15 minutes;

Step b): Method 1: oxidation of an intermediate compound 17 with PCC; then, reductive amination with $HNR^1R^2$ using a reducing agent such as $NaBH_4$; or Method 2: mesylation of an intermediate compound 17 with MsCl and DMAP, a base such as $Et_3N$, in a reaction-inert solvent such as $CH_2Cl_2$; then nucleophilic substitution with an excess of $HNR^1R^2$, optionally in the presence of a base such as $K_2CO_3$;

Step c) removal of the Cbz protecting group by hydrogenation of an intermediate compound 18 with a palladium-carbon catalyst (1 atm) in a reaction-inert solvent such as MeOH, and in the presence of a base such as $Et_3N$, for example at room temperature for about 3 hours.

An intermediate compound 10 leads to a final compound of formula (Ia); an intermediate compound 13 leads to a final compound of formula (Ib).

Methods B-D below represent alternative routes to the preparation of the above final compounds of formula Ia and Ib:

Method B: Synthesis of (2R,3aR,12bS)- and (2S,3aR,12bS)-Final Compounds

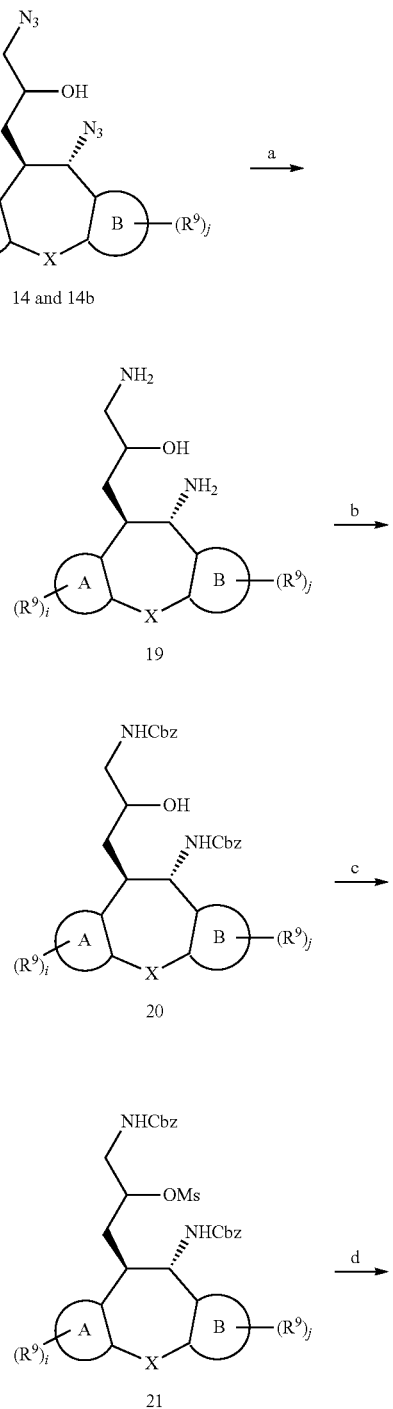

14 and 14b

19

20

21

-continued

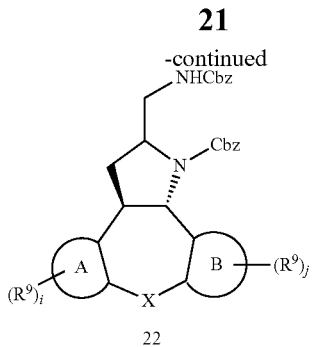

22

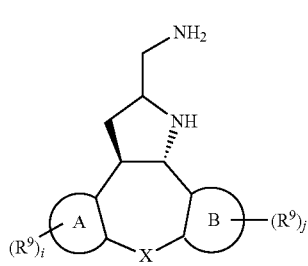

Ia1: 2R,3aR,12bS
Ib1: 2S,3aR,12bS

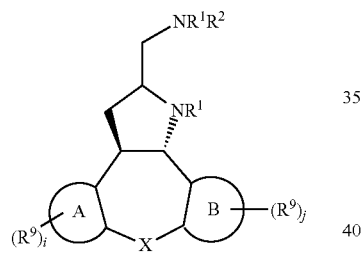

Ia2: 2R,3aR,12bS (R¹ and R² are not hydrogen)
Ib2: 2S,3aR,12bS

Step a): hydrogenation of an intermediate compound 14 or 14b with a palladium-carbon catalyst (1 atm), in a reaction-inert solvent such as MeOH and in the presence of a base such as $Et_3N$, for example at room temperature for about 3 hours;

Step b): treatment of an intermediate compound 19 with CbzCl, with base such as $K_2CO_3$, in a reaction-inert solvent mixture such as THF—$H_2O$;

Step c): mesylation of an intermediate compound 20 with MsCl and DMAP, with a base such as $Et_3N$, in a reaction-inert solvent such as $CH_2Cl_2$, for example at room temperature for about 16 hours;

Step d): treatment of an intermediate compound 21 with a base such as t-BuOK, in a reaction-inert polar aprotic solvent such as THF;

Step e): hydrogenation of an intermediate compound 22 with a palladium-carbon catalyst (1 atm), in a reaction-inert solvent such as MeOH, for example at room temperature for about 3 hours;

Step f) treatment of an final compound Ia1 (having the 2R (down) configuration) with an aldehyde such formaldehyde or ketone, in an alcoholic solvent in the presence of AcOH and a reducing agent such as hydrogen/palladium on carbon or $NaCNBH_3$ leads to a trisubstituted final compound Ia2.

Method C: Synthesis of (2RS,3aR*,12bS*)-Final Compounds

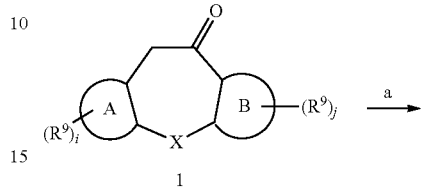

1

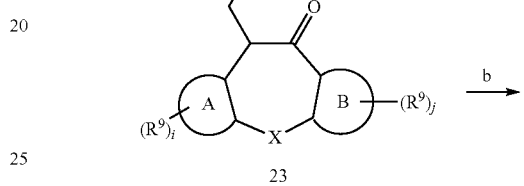

23

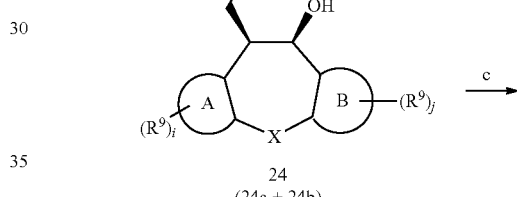

24
(24a + 24b)

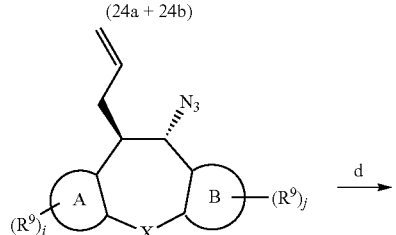

25

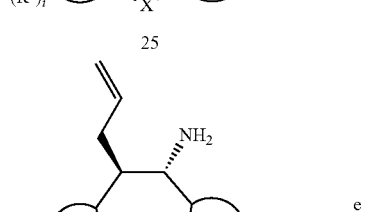

26

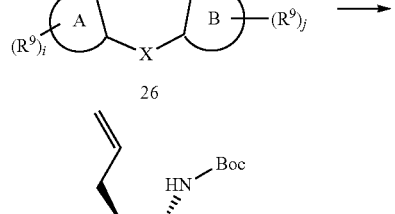

27

-continued

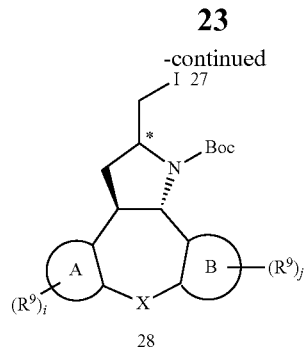

28

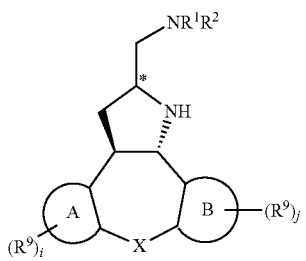

Ia: 2R,3aR,12bS
Ib: 2S,3aR,12bS

Step a): allylation of an intermediate 1 with a base such as NaH and allyl bromide, in a reaction-inert solvent such as THF, for example at about 65° C. for about 2-3 hours;

Step b): reduction of an intermediate compound 23 with a reducing agent such as NaBH$_4$ (in a phosphate buffer at pH 7), in a reaction-inert solvent such as i-PrOH, for example at room temperature, leads to intermediate compound 24 comprising a enantiomeric mixture of 24a and 24b with both substituents in either the up or down configuration;

Step c): treatment of an intermediate compound 24 with DPPA, DIAD/P(Ph)$_3$, in a reaction-inert solvent such as THF, for example at about −15° C. to room temperature for about 24 hours;

Step d): reduction of an intermediate compound 25 with a reducing agent, most preferably LiAlH$_4$, in a reaction-inert solvent such as THF, for example between about 0° C. and room temperature;

Step e): protection of an intermediate compound 26 with Boc$_2$O with an aqueous base such as K$_2$CO$_3$, in a reaction-inert solvent such as THF, for example at room temperature;

Step f): iodocyclization of an intermediate compound 27 with IPy$_2$BF$_4$ in a reaction-inert solvent such as CH$_2$Cl$_2$, for example at room temperature;

Step g): amination of an intermediate compound 28 with excess HNR$^1$R$^2$ in aqueous THF, at about 135° C. in a pressurized vessel (for example a steel bomb) for about 3-6 hours; or alternatively for example with HNMe$_2$ in anhydrous THF and calcium oxide to remove the leaving group.

Step h): deprotection with an acid such as HBr in AcOH, or HCl in MeOH, for about 1-2 hours under reflux or at room temperatures.

Method D: Synthesis of (2RS,3aR,12bS)-Final Compounds

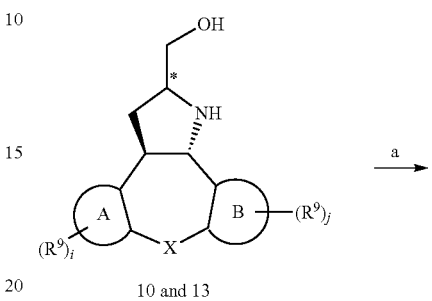

10 and 13

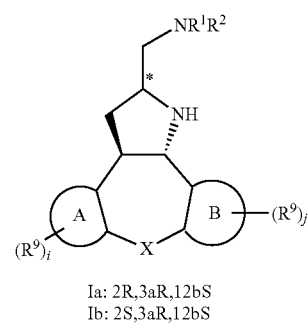

29

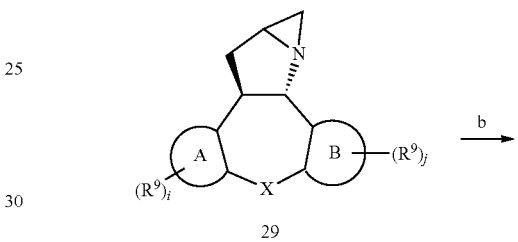

Ia: 2R,3aR,12bS
Ib: 2S,3aR,12bS

Step a): Mitsonobu-reaction of an intermediate compound 10 or 13 with DIAD/P(Ph)$_3$, in a reaction-inert solvent such as THF, for example at about −15° C. to room temperature for about 24 hours;

Step b): iodotrimethylsilane-mediated opening of the aziridine ring of an intermediate compound 29, followed by an in-situ reaction with an appropriate amine HNR$^1$R$^2$ in boiling acetonitrile. An intermediate compound 10 leads to a final compound of formula Ia; an intermediate compound 13 leads to a final compound of formula Ib.

Method E: Preparation of Pyrroloimidazole Derivatives

The following reaction scheme illustrates the preparation of compounds of formula (I) in which C is a group of formula (c-1) in which R$^{11}$ and R$^{10}$ form a condensed imidazole residue, represented by formula II below.

(III)

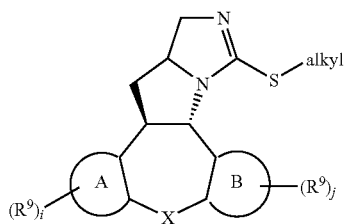

Method F: Preparation of Pyrrolopiperazine Derivatives

The following reaction schemes illustrate the preparation of compounds of formula (I) in which C is a group of formula (c-1) in which $R^{11}$ and $R^{10}$ form a condensed piperazine residue, represented by formula III below in which $R^x$ is hydrogen or alkyl and the piperazine ring has the S configuration (Scheme F1) or the R configuration (Scheme F2).

Scheme E

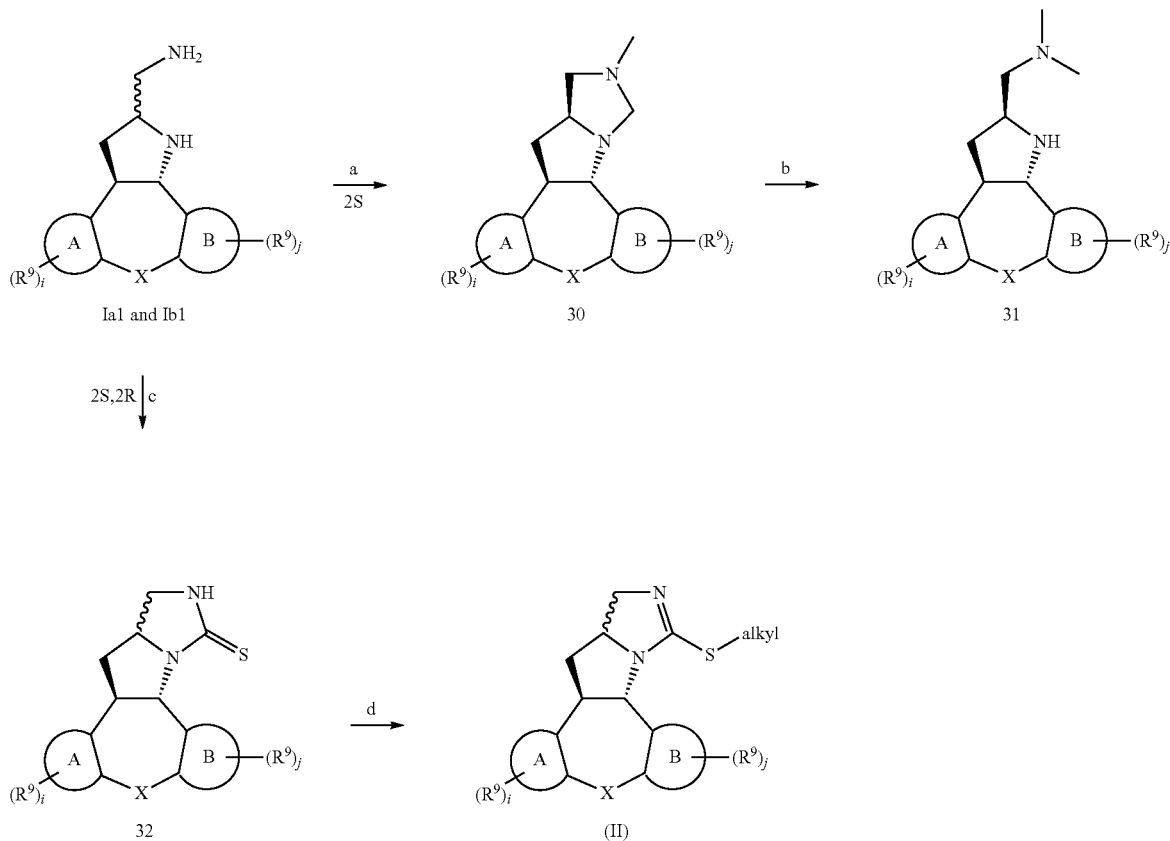

Step a): hydrogenation of a final compound I-b1 (having the 2S(up) configuration) with a palladium-carbon catalyst (1 atm) with formaldehyde, in a reaction-inert solvent such as MeOH, for example at room temperature for about 3 hours, resulting in a final compound 30;

Step b): treatment of a final compound 30 with $NaCNBH_3$/TFA, in a solvent such as MeOH, resulting in a final compound 31;

Step c): treatment of a final compound I-a1 or I-b1 (having respectively the 2R (down) or 2S (up) configuration) with $CS_2$ in a reaction-inert solvent such as DMF, for example at about 50-60° C. for about 30 minutes, resulting in a final compound 32;

Step d): alkylation of a final compound 32 with for example an alkyl halide, in a reaction-inert solvent such as MeOH or $Et_3N$, for example under reflux resulting in a final compound II.

(III)

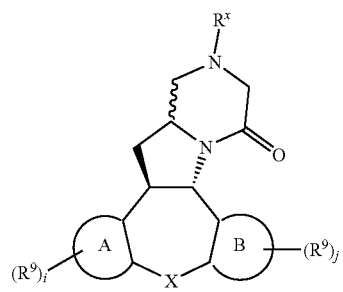

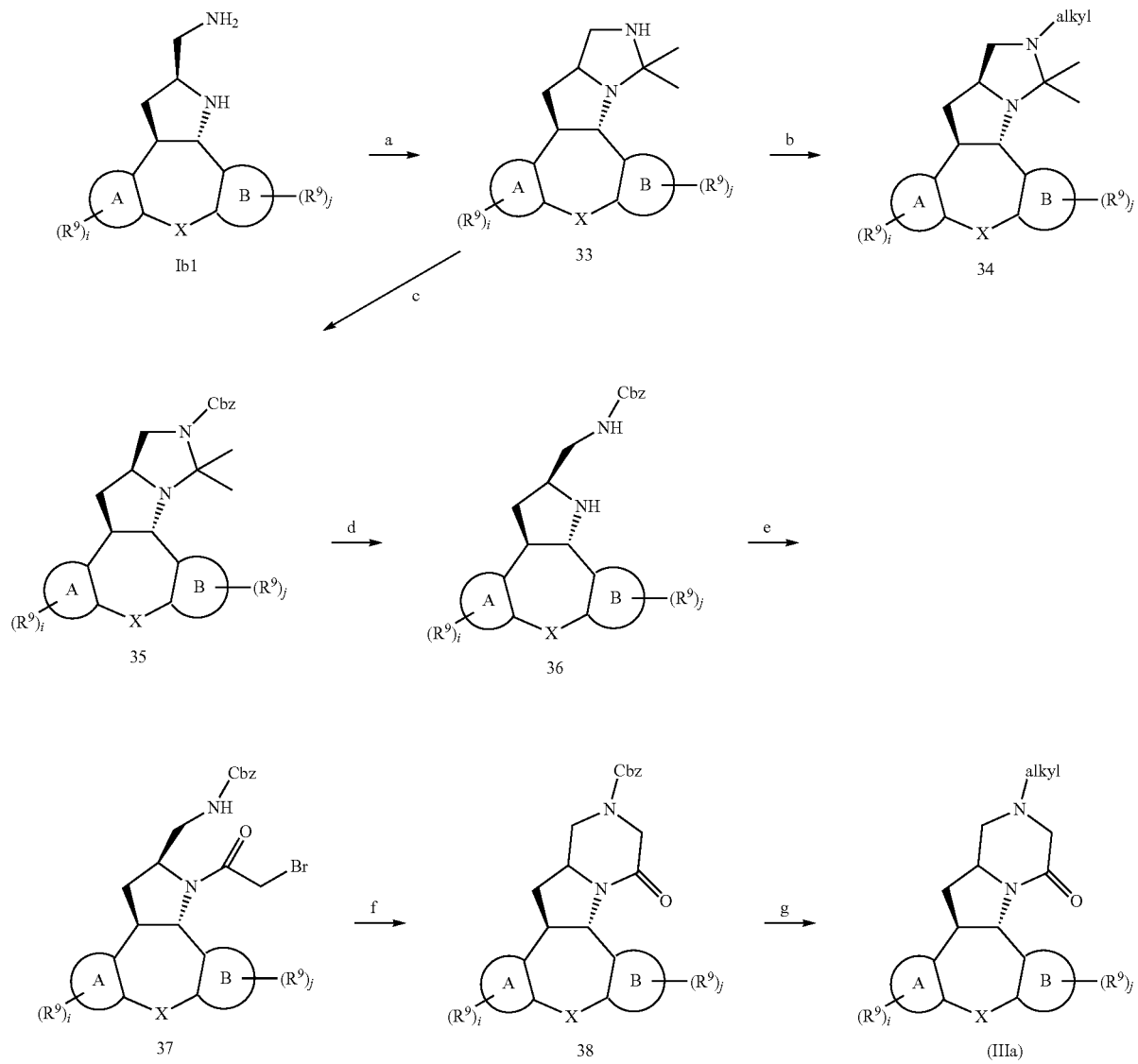

Scheme F1

Step a): aminal formation from a final compound Ib1 with acetone in a reaction-inert solvent such as MeOH, for example at about 60° C. for about 4 hours;
Step b): trans-aminalisation and reductive amination of a final compound 33 with an appropriate aldehyde or ketone for example formaldehyde, and hydrogenation with a palladium-carbon catalyst (1 atm);
Step c): protection of a final compound 33 with CbzCl, with base such as $K_2CO_3$, in a reaction-inert solvent mixture such as THF—$H_2O$;
Step d): hydrolysis of intermediate compound 35 with an acid such as hydrochloric acid, in aqueous THF, for example at room temperature for about 12 hours;
Step e): acylation of an intermediate compound 36 with an acid halide, in particular BrC(=O)$CH_2$Br, in EtAc in the presence of aqueous sodium hydroxide;
Step f): intramolecular cyclization of an intermediate compound 37 with a base such as $K_2CO_3$ in a reaction-inert solvent such as DMF;
Step g): removal of the Cbz-moiety by hydrogenation of an intermediate compound 38 with a palladium-carbon catalyst (1 atm) and in-situ treatment with an aldehyde or ketone, for example formaldehyde, in a reaction-inert solvent such as MeOH, for example at room temperature for about 3 hours;

Scheme F2

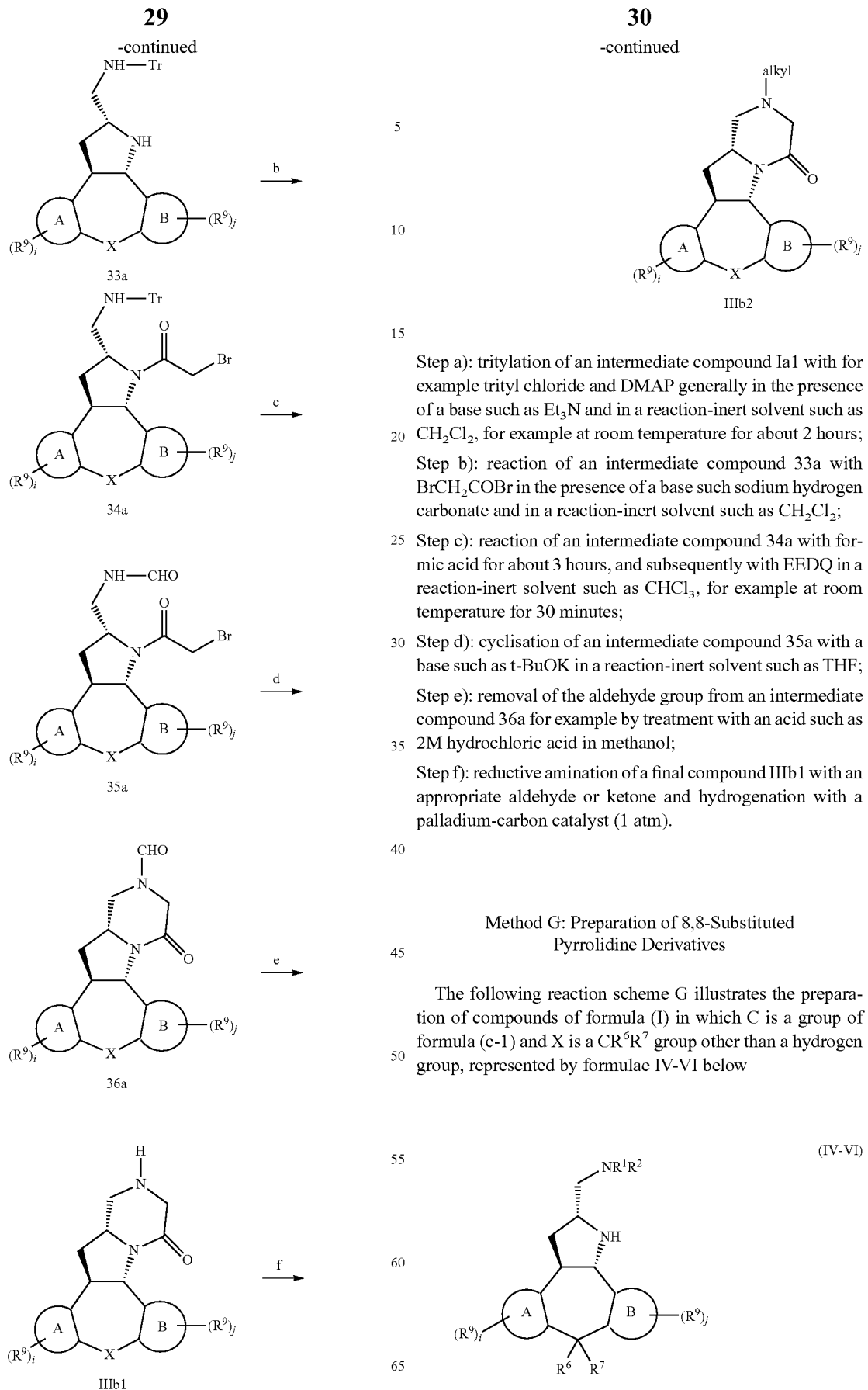

Step a): tritylation of an intermediate compound Ia1 with for example trityl chloride and DMAP generally in the presence of a base such as Et$_3$N and in a reaction-inert solvent such as CH$_2$Cl$_2$, for example at room temperature for about 2 hours;

Step b): reaction of an intermediate compound 33a with BrCH$_2$COBr in the presence of a base such sodium hydrogen carbonate and in a reaction-inert solvent such as CH$_2$Cl$_2$;

Step c): reaction of an intermediate compound 34a with formic acid for about 3 hours, and subsequently with EEDQ in a reaction-inert solvent such as CHCl$_3$, for example at room temperature for 30 minutes;

Step d): cyclisation of an intermediate compound 35a with a base such as t-BuOK in a reaction-inert solvent such as THF;

Step e): removal of the aldehyde group from an intermediate compound 36a for example by treatment with an acid such as 2M hydrochloric acid in methanol;

Step f): reductive amination of a final compound IIIb1 with an appropriate aldehyde or ketone and hydrogenation with a palladium-carbon catalyst (1 atm).

Method G: Preparation of 8,8-Substituted Pyrrolidine Derivatives

The following reaction scheme G illustrates the preparation of compounds of formula (I) in which C is a group of formula (c-1) and X is a CR$^6$R$^7$ group other than a hydrogen group, represented by formulae IV-VI below Scheme G

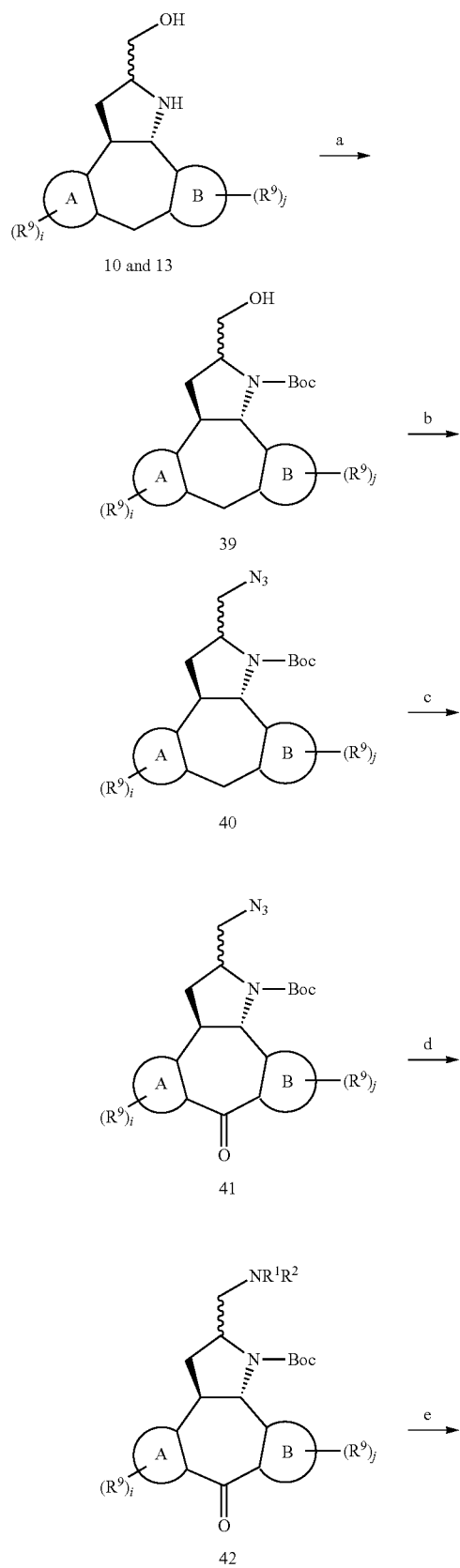

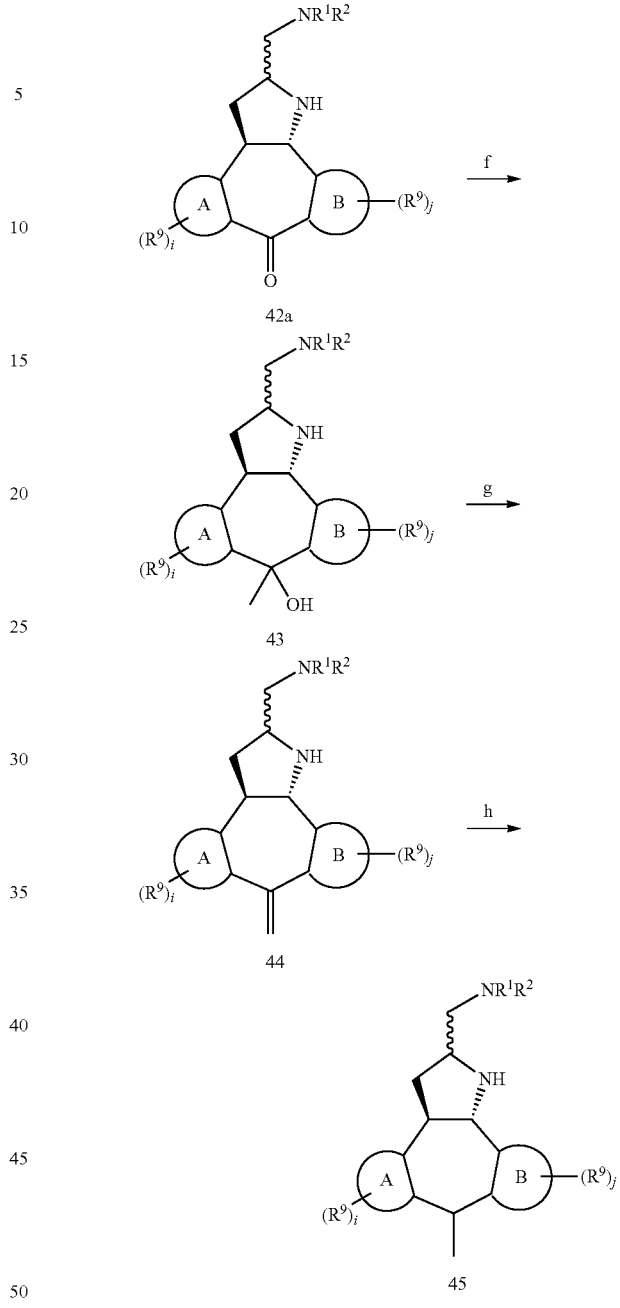

Step a): treatment of an intermediate compound 10 or 13 with Boc$_2$O and with a base such as aqueous KOH or NaOH, in a solvent such as THF or dioxane, for example at room temperature for about 6 hours;

Step b): treatment of an intermediate compound 39 with DIAD/P(Ph)$_3$, in a solvent such as THF, for example at about −15 C to room temperature;

Step c): oxidation of an intermediate compound 40 with KMnO$_4$, in the presence of a phase-transfer catalyst such as n-Bu$_4$NHSO$_4$, in a solvent system such as CH$_2$Cl$_2$-H$_2$O, for example at room temperature for about 16 hours;

Step d): hydrogenation of an intermediate compound 41 with a palladium-carbon catalyst (1 atm), in a reaction-inert solvent such as MeOH, for example at room temperature; followed by treatment with an aldehyde or ketone, such as formaldehyde, in the presence of AcOH to form an intermediate compound in which $R^1$ and $R^2$ are each alkyl;

Step e) treatment of intermediate compound 42 with 50% sulfuric acid in dioxane, for example at room temperature for 3 hours to remove the Boc protecting group to form a final compound 42a;

Step f): subjecting a final compound 42a to a Grignard reaction with methyl magnesium bromide, in a solvent such as THF, for example at room temperature to form a final compound 43;

Step g): treatment of a final compound 43 with sulfonyl chloride and pyridine, for example at room temperature for 16 hours to form a final compound 44;

Step h): hydrogenation of a final compound 44 with a palladium-carbon catalyst (1 atm), in a solvent such as MeOH, for example at room temperature to form a final compound 45.

Method H: Preparation of 3-Substituted Pyrrolidine Derivatives

The following reaction scheme H illustrates the preparation of compounds of formula (I) in which C is a group of formula (c-3), $Y^1$ is NH and $R^{11}$ is a group of formula (d-1) represented by formula VII below.

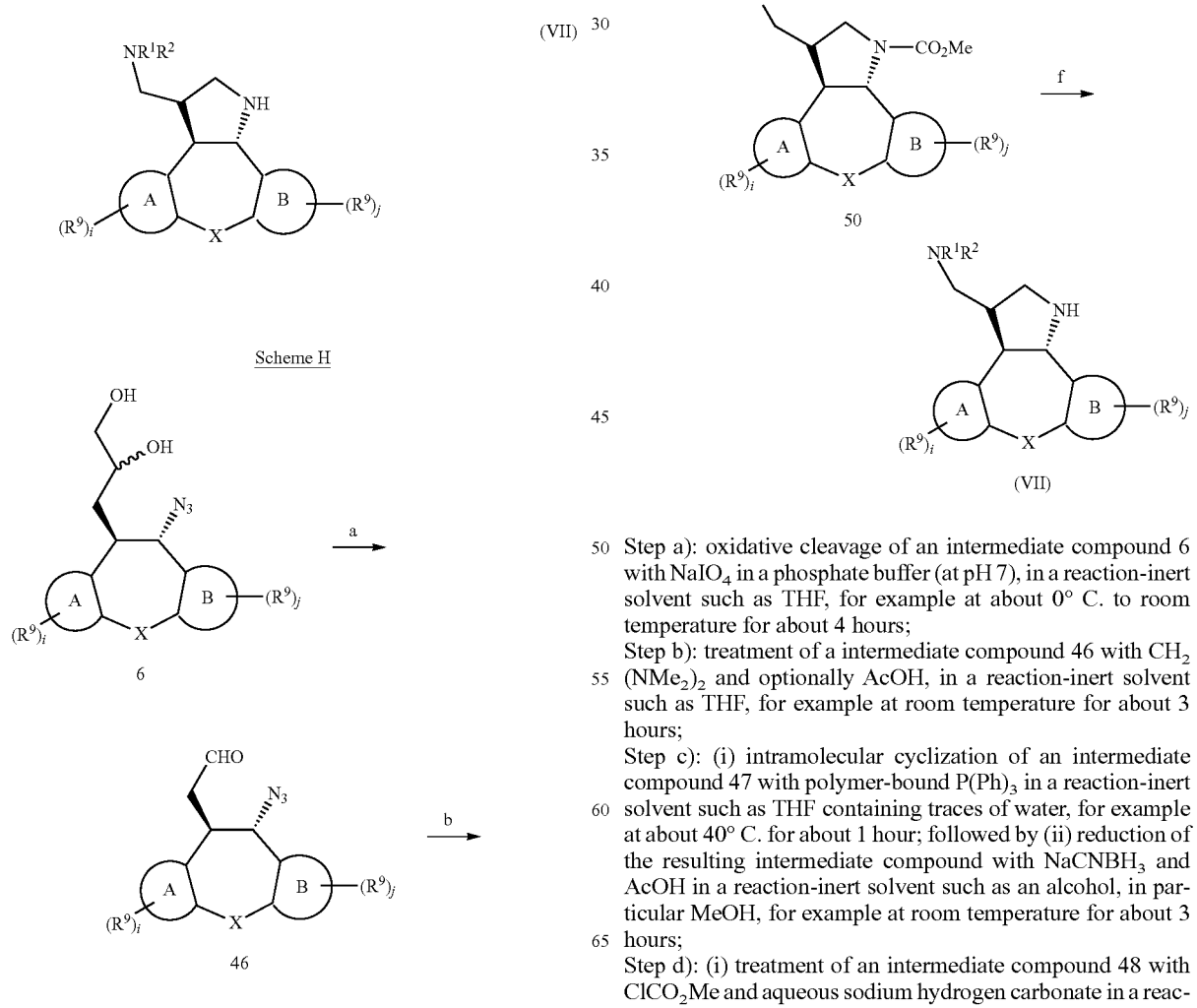

Step a): oxidative cleavage of an intermediate compound 6 with $NaIO_4$ in a phosphate buffer (at pH 7), in a reaction-inert solvent such as THF, for example at about 0° C. to room temperature for about 4 hours;

Step b): treatment of a intermediate compound 46 with $CH_2(NMe_2)_2$ and optionally AcOH, in a reaction-inert solvent such as THF, for example at room temperature for about 3 hours;

Step c): (i) intramolecular cyclization of an intermediate compound 47 with polymer-bound $P(Ph)_3$ in a reaction-inert solvent such as THF containing traces of water, for example at about 40° C. for about 1 hour; followed by (ii) reduction of the resulting intermediate compound with $NaCNBH_3$ and AcOH in a reaction-inert solvent such as an alcohol, in particular MeOH, for example at room temperature for about 3 hours;

Step d): (i) treatment of an intermediate compound 48 with $ClCO_2Me$ and aqueous sodium hydrogen carbonate in a reaction-inert solvent such as $CH_2Cl_2$; (ii) followed by the treatment of the resulting intermediate compound with $NaBH_4$, $BF_3^-Et_2O$ in a reaction-inert solvent such as THF, for example at room temperature for about 24 h; and (iii) followed by the treatment of the resulting intermediate compound with $H_2O_2$ and aqueous KOH, for example at room temperature for about 3 hours;

Step e): treatment of an intermediate compound 49 with DIAD/P(Ph)$_3$ and DPPA in a reaction-inert solvent such as THF, for example at about −15° C. to room temperature;

Step f): (i) subjecting an intermediate compound 50 to a Staudinger reaction or hydrogenating with a palladium-carbon catalyst (1 atm) in a reaction-inert solvent such as MeOH, for example at room temperature; and then (ii) followed by a reductive amination with an aldehyde or ketone, for example formaldehyde.

Method I: Preparation of
Tetrahydrofurane-3-Substituted Derivatives

The following reaction scheme I illustrates the preparation of compounds of formula (I) in which C is a group of formula (c-3), $Y^2$ is O and $R^{11}$ is a group of formula (d-1), represented by formula VIII below.

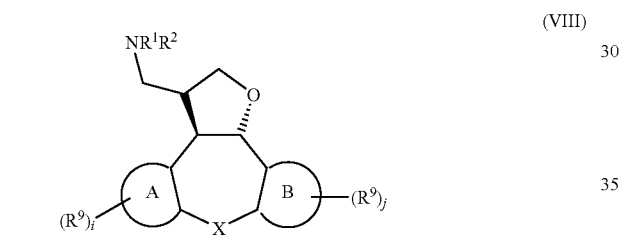

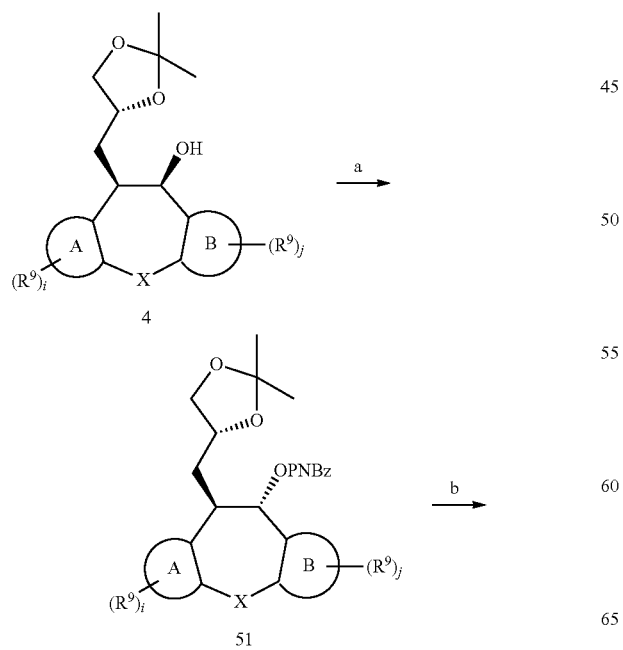

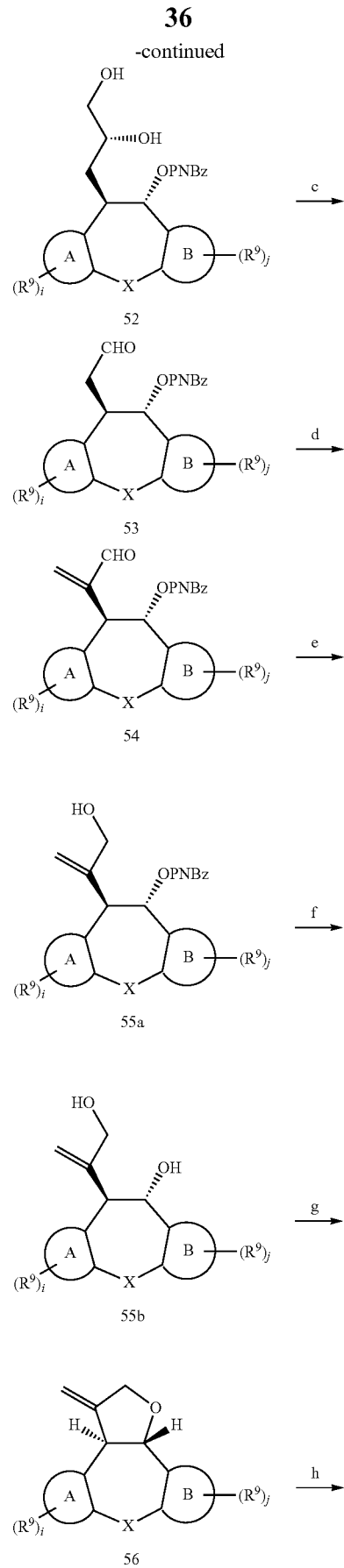

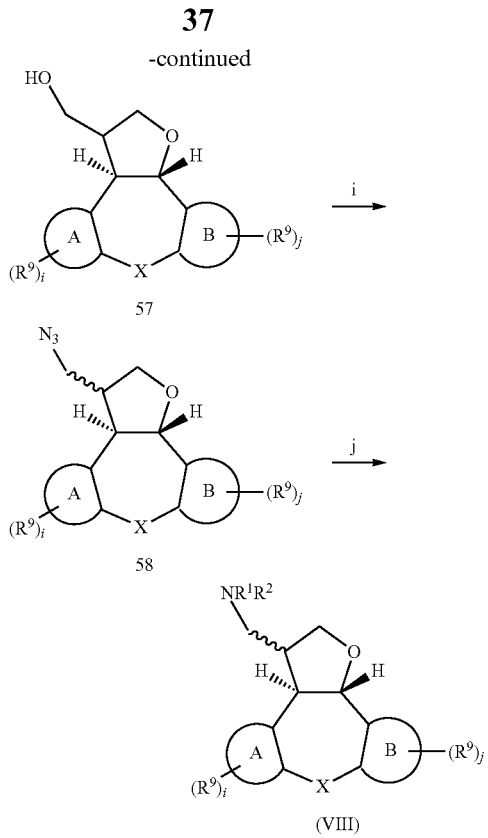

Step a): protection of the alcohol function of an intermediate compound 4 with DIAD/P(Ph)₃ and 4-nitrobenzoic acid (PN-BzOH) in a reaction-inert solvent such as THF, for example at about −15° C. to room temperature, for a suitable time, e.g. about 15 hours;

Step b): treatment of an intermediate compound 51 with hydrochloric acid in THF (e.g. as a 1:1 mixture using 1 N hydrochloric acid), for example at room temperature for about 5 hours;

Step c): treatment of an intermediate compound 52 with NaIO₄ at pH 7 using a phosphate buffer, in a reaction-inert solvent such as THF, for example at about 0° C. to room temperature for about 4 hours;

Step d): treatment of an intermediate compound 53 with CH₂(NMe₂)₂ and AcOH in a reaction-inert solvent such as THF, for example at room temperature for about 3 hours;

Step e): reduction of an intermediate compound 54 with a reducing agent such as sodium borohydride, in a reaction-inert solvent such as methanol, EtOH or i-PrOH, for example at room temperature for about 4 hours;

Step f): treatment of an intermediate 55a with sodium methoxide in a reaction-inert solvent such as methanol, for example at room temperature for about 4 hours;

Step g): treatment of an intermediate compound 55b with DIAD/tributylphosphine in a reaction-inert solvent such as toluene, for example at room temperature for about 3 hours;

Step h): (i) hydroboration of an intermediate compound 56 with sodium borohydride and BF₃-Et₂O, in a reaction-inert solvent such as THF, for example at room temperature for about 24 hours; and (ii) treatment with H₂O₂, aqueous sodium hydroxide, in a reaction-inert solvent such as THF, for example at room temperature for about 4 hours;

Step i): treatment of an intermediate compound 57 with DIAD/P(Ph)₃, DPPA, in a reaction-inert solvent such as THF, for example at about −15° C. to room temperature for about 15 hours;

Step j): (i) subjecting an intermediate compound 58 to a Staudinger reaction, or hydrogenation with a palladium-carbon catalyst (1 atm), in a reaction-inert solvent such as MeOH, for example at room temperature for about 1.5 hours; and (ii) reductive amination with an aldehyde or ketone, for example aqueous formaldehyde in AcOH and methanol.

Method J: Preparation of 3-Substituted Tetrahydropyran Derivatives

The following reaction scheme J illustrates the preparation of compounds of formula (I) in which C is a group of formula (c-2), $Y^2$ is O and $R^{11}$ is a group of formula (d-1), represented by formula IX below. The compound can be either cis (Scheme J1) or trans (Scheme J2) with respect to the oxygen.

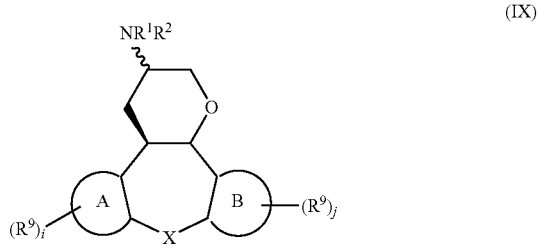

Scheme J1 (cis)

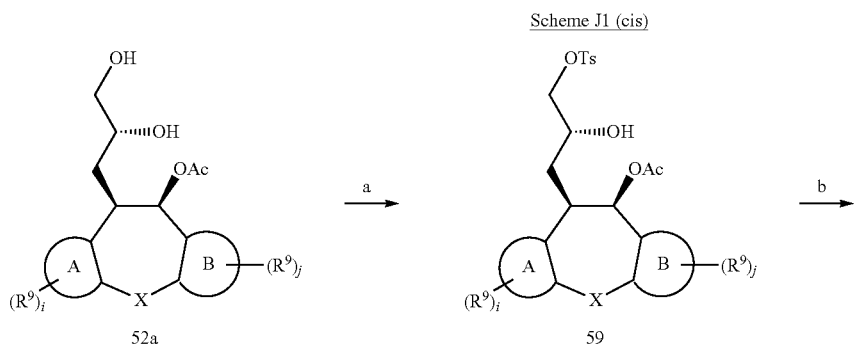

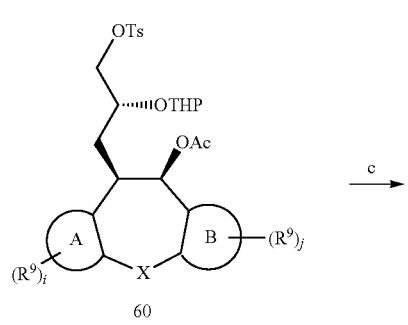
60

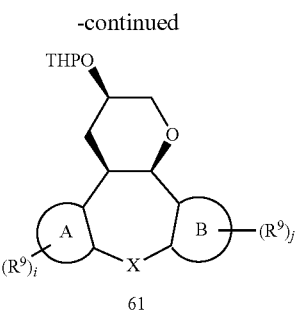
61

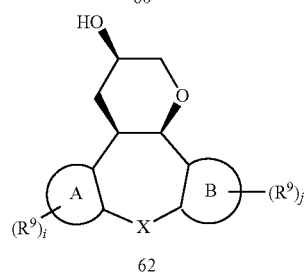
62

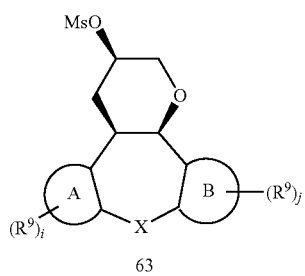
63

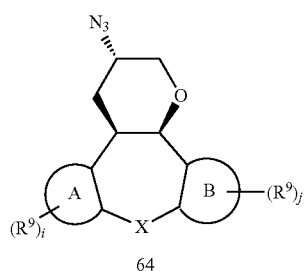
64

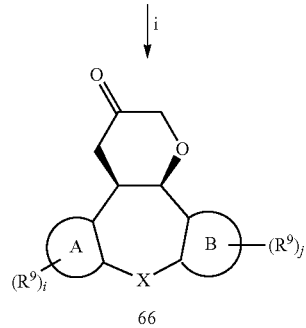
66

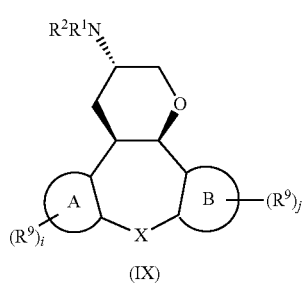
(IX)

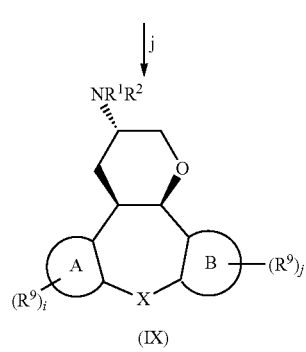
(IX)

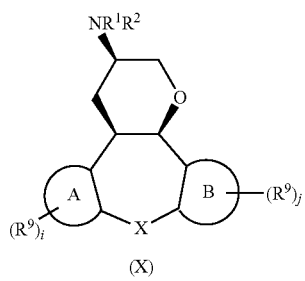
(X)

Step a): monotosylation of an intermediate compound 52a (prepared in an analogous manner to intermediate compound 52) with TsCl, Et$_3$N and Bu$_2$SnO, for example at room temperature for about 16 hours in a reaction-inert solvent such as toluene or CH$_2$Cl$_2$;

Step b): treatment of an intermediate compound 59 with DHP and CSA, in a reaction-inert solvent such as CH$_2$Cl$_2$, for example at room temperature for about 3 hours;

Step c): deacetylation of an intermediate compound 60 with a base such as K$_2$CO$_3$, in a reaction-inert solvent such as MeOH, for example at room temperature for about 3 hours, followed by intramolecular cyclization with NaH, in a reaction-inert solvent such as THF, for example at about 0° C. to room temperature for about 4 hours;

Step d): deprotection of an intermediate compound 61 with Dowex, in a reaction-inert solvent such as MeOH/H$_2$O, for example at room temperature for about 2 days;

Step e): mesylation of an intermediate compound 62 with MsCl, DMAP and Et$_3$N, in a reaction-inert solvent such as CH$_2$Cl$_2$, for example at room temperature for about 4 hours;

Step f): treatment of an intermediate compound 63 with NaN$_3$, in a reaction-inert solvent such as DMF, for example at about 90° C. for about 2 hours;

Step g): hydrogenation of an intermediate compound 64 with a palladium-carbon catalyst (1 atm), in a reaction-inert solvent mixture such as i-PrOH/THF, for example at room temperature for about 3 hours;

Step h): hydrogenation of an intermediate compound 65 with a palladium-carbon catalyst (1atm), in a reaction-inert solvent mixture such as i-PrOH/THF, and reductive amination with an aldehyde or ketone;

Step i): oxidation of an intermediate compound 62 with a PCC catalyst, in a reaction-inert solvent such as CH$_2$Cl$_2$, for example at room temperature for about 24 hours;

Step j): reductive amination of an intermediate compound 66 with an appropriate R$^1$R$^2$NH compound and hydrogenation with a palladium-carbon catalyst (1 Atm) in the presence of a base such as Et$_3$N, in a reaction-inert solvent such as MeOH, for example at room temperature for about 24 hours.

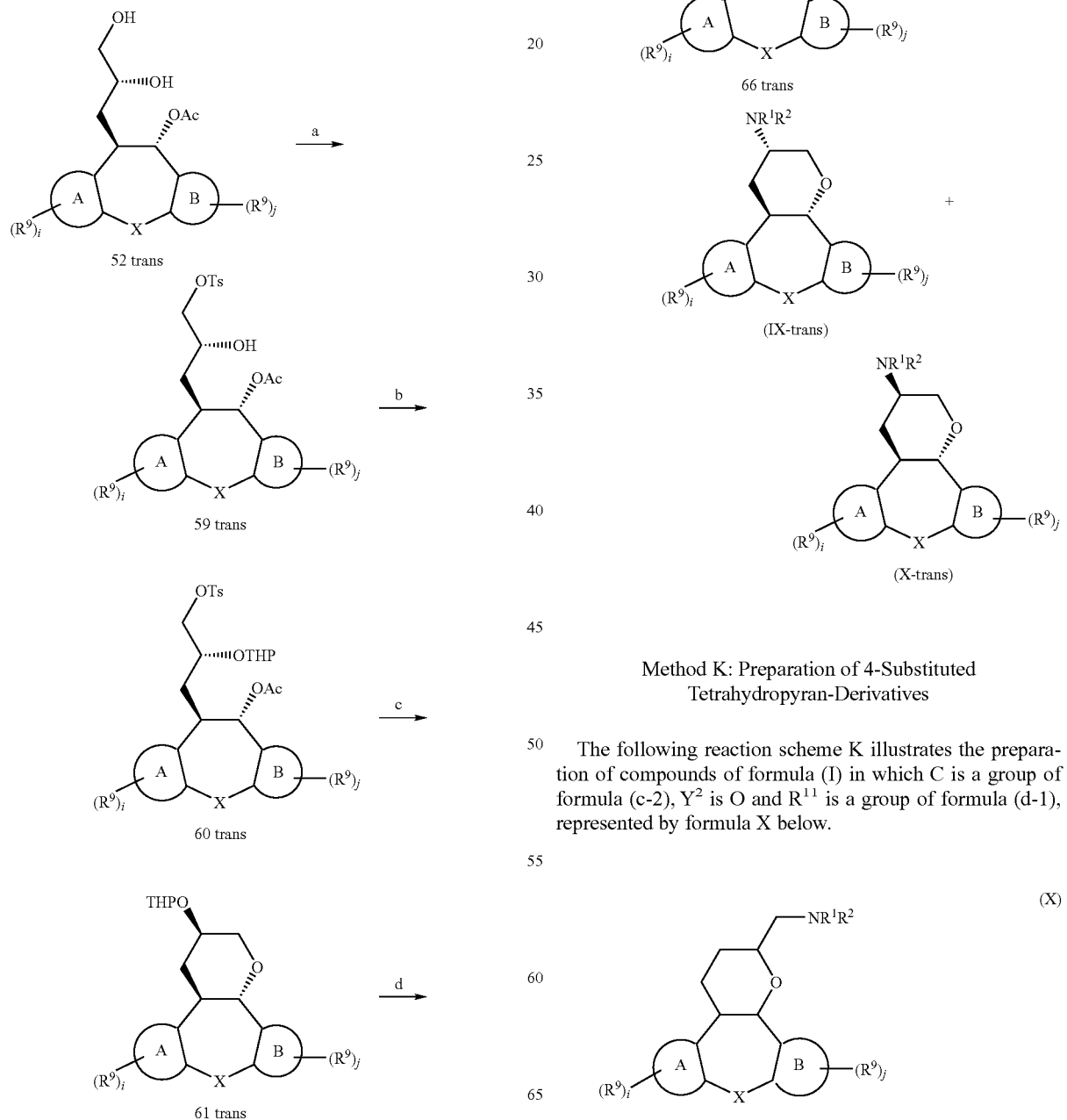

Method K: Preparation of 4-Substituted Tetrahydropyran-Derivatives

The following reaction scheme K illustrates the preparation of compounds of formula (I) in which C is a group of formula (c-2), Y$^2$ is O and R$^{11}$ is a group of formula (d-1), represented by formula X below.

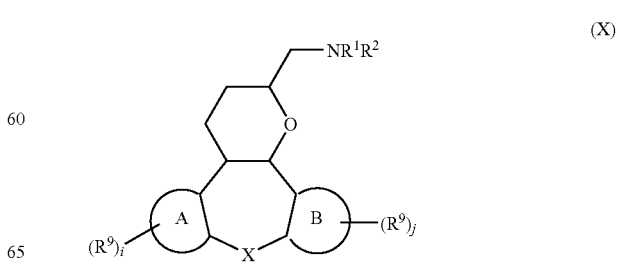

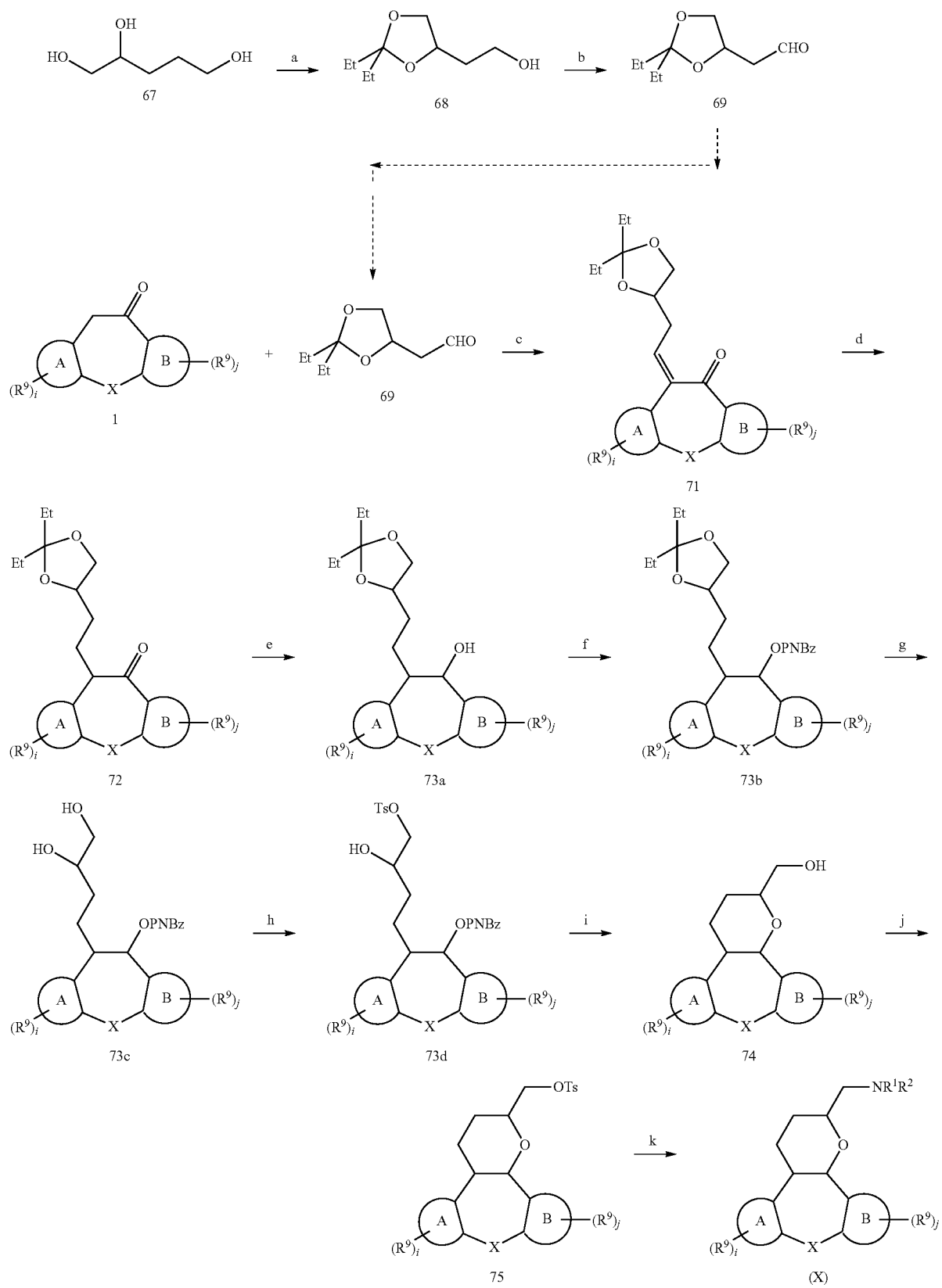

Step a): treatment of an intermediate compound 67 with 3-pentanone and CSA, for example at about 50° C. for about 16 hours;

Step b): treatment of an intermediate compound 68 with PCC in a reaction-inert solvent such as $CH_2Cl_2$, using molecular sieves (4 A), for example at about 0° C. to room temperature for about 75 minutes;

Step c): reaction of an intermediate compound 1 with the intermediate compound 69, with $MgBr_2$, using t-BuOK as a catalyst, in a reaction-inert solvent such as PhMe/THF, for example at room temperature for about 23 hours; this reaction must be carried out in the absence of oxygen, preferably under argon atmosphere;

Step d): hydrogenation of an intermediate compound 71 with hydrogen over a palladium-carbon catalyst (10%) in a reaction-inert solvent such as $Et_3N$, i-PrOH or toluene, or a mixture of them, for example at room temperature for about 15 hours;

Step e): reduction of an intermediate compound 72 with a reducing agent such as sodium borohydride, in a phosphate buffer at pH 7, in a reaction-inert solvent such as i-PrOH, for example at about 0° C. to room temperature for about 1 hour;

Step f): treatment of an intermediate compound 73a with $DIAD/P(Ph)_3$, 4-nitrobenzoic acid (PNBzOH), in a reaction-inert solvent such as THF, for example at about −15° C. to room temperature for about 15 hours;

Step g): treatment of an intermediate compound 73b with hydrochloric acid (1 N) in THF (1:1), for example at room temperature for about 5 hours;

Step h): tosylation of an intermediate compound 73c with TsCl, $Et_3N$, dibutyl(oxo)-stannane ($Bu_2SnO$), in a reaction-inert solvent such as $CH_2Cl_2$, for example at room temperature for about 12 hours;

Step i): cyclization of intermediate compound 73d with sodium methoxide in a reaction-inert solvent such as methanol, for example at room temperature for about 3 hours;

Step j): tosylation of an intermediate compound 74 with TsCl, $Et_3N$ and DMAP, in a reaction-inert solvent such as $CH_2Cl_2$, for example at room temperature for about 16 hours;

Step k): treatment of an intermediate compound 75 with a compound of formula $HNR^1R^2$ in a reaction-inert solvent such as THF, in a steel bomb at about 135° C. for about 15 hours.

Method L: Preparation of tetrahydrothiophene-2-Substituted Derivatives

The following reaction schemes L1-L3 illustrates the preparation of compounds of formula (I) in which C is a group of formula (c-1), $Y^1$ is SO(n) and $R^{11}$ is a group of formula (d-1), represented by formulae XIa-c and XIIa-c below.

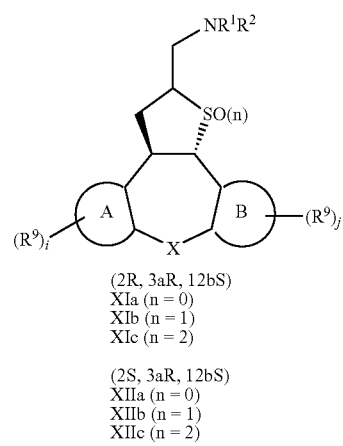

(2R, 3aR, 12bS)
XIa (n = 0)
XIb (n = 1)
XIc (n = 2)

(2S, 3aR, 12bS)
XIIa (n = 0)
XIIb (n = 1)
XIIc (n = 2)

Scheme L1: Synthesis of (2R,3aR,12bS)-tetrahydrothiophene intermediates

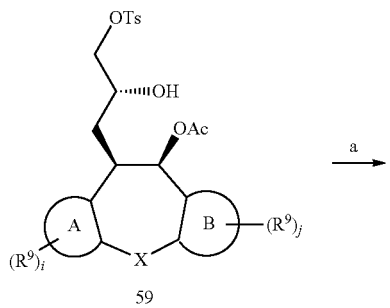

59

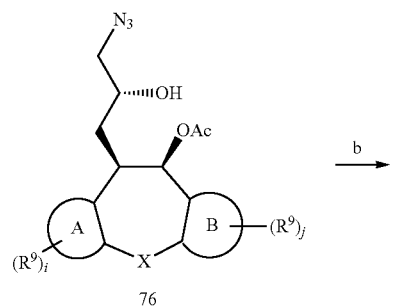

76

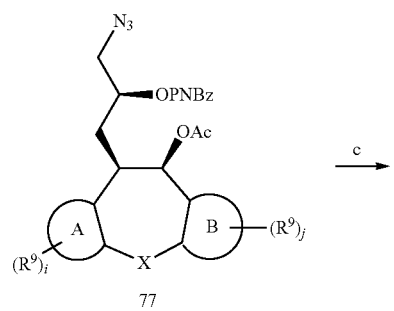

77

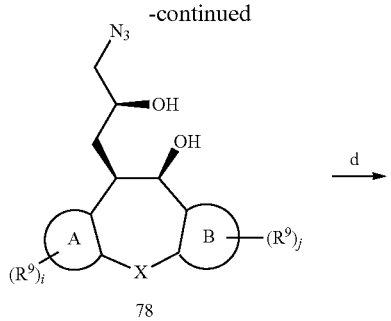
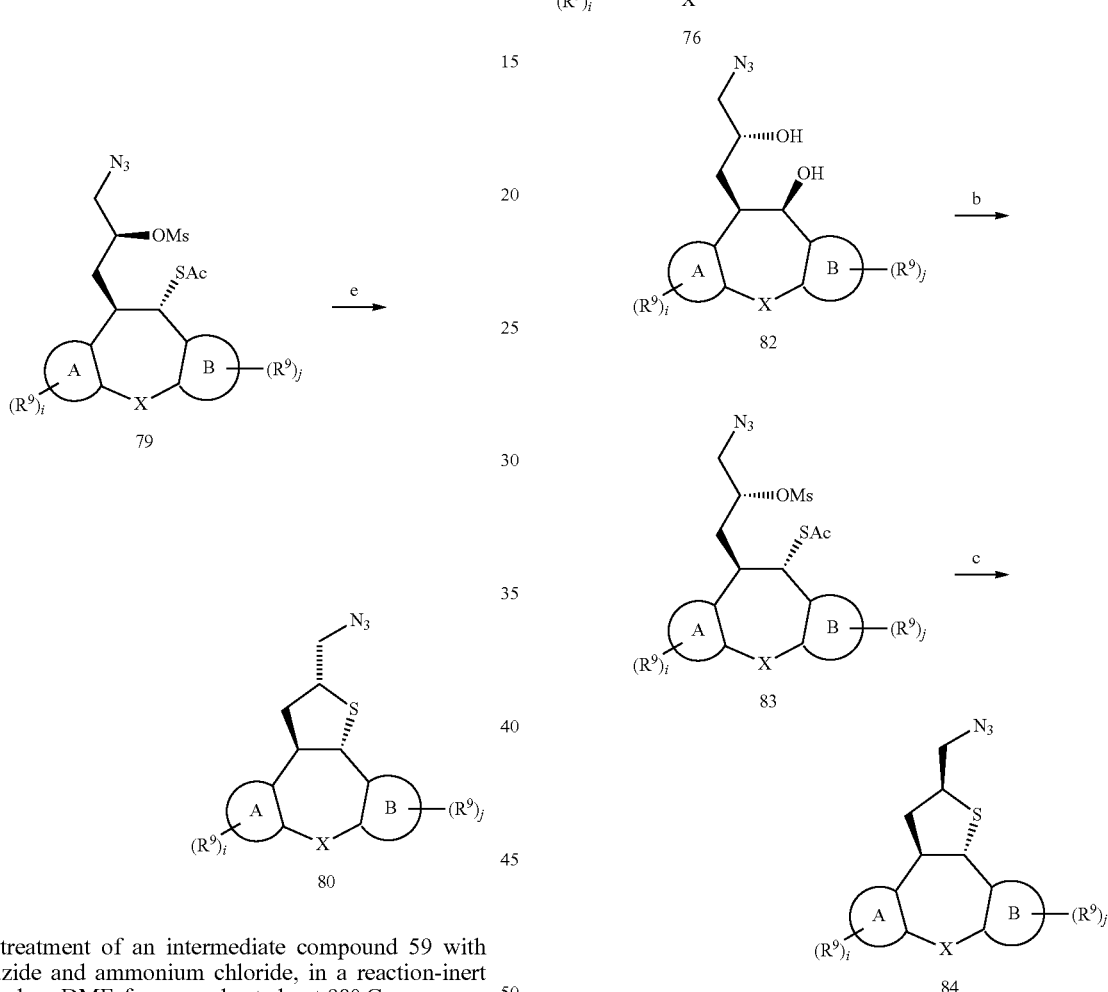

Scheme L2: Synthesis of (2S,3aR,12bS)-tetrahydrothiophene intermediates

Step a): treatment of an intermediate compound 59 with sodium azide and ammonium chloride, in a reaction-inert solvent such as DMF, for example at about 90° C.;

Step b): subjecting an intermediate compound 76 to a Mitsonobu reaction (giving a supplementary inversion at the carbon atom) with DIAD/P(Ph)$_3$ and p-nitrobenzoic acid (PNBzOH), in a reaction-inert solvent such as THF, for example at 0° C. to room temperature for about 2 hours;

Step c): deprotection of an intermediate compound 77 with a base solution such as K$_2$CO$_3$/MeOH, for example at room temperature for about 2 hours;

Step d): mesylation of an intermediate compound 78 with MsCl and DMAP, using a base such as Et$_3$N, in a reaction-inert solvent such as CH$_2$Cl$_2$, for example at 0° C. to room temperature for about 30 minutes, followed by in situ treatment with AcSH at 0° C. to room temperature for about 5 hours;

Step e): deacylation and concomitant cyclization of an intermediate compound 79 with a base solution such as K$_2$CO$_3$/MeOH, for example at room temperature for about 2 hours;

Step a): treatment of an intermediate compound 76 with a base solution such as K$_2$CO$_3$/MeOH, for example at room temperature for about 2 hours;

Step b): (i) treatment of an intermediate compound 82 with (CH$_3$SO$_2$)$_2$O, Et$_3$N, DMAP, in a reaction-inert solvent such as CH$_2$Cl$_2$, for example at about 0° C.; or (ii) treatment of an intermediate compound 82 with MsCl, DMAP and Et$_3$N, in a reaction-inert solvent such as CH$_2$Cl$_2$ at about 0° C., followed by in situ treatment with AcSH at about 0° C. for about 5 hours;

Step c): deacylation and concommitant cyclization of an intermediate compound 83 with a base such as K$_2$CO$_3$/MeOH, for example at room temperature for about 30 minutes.

Scheme L3: Synthesis of (2RS,3aR,12bS)-tetrahydrothiophene derivatives

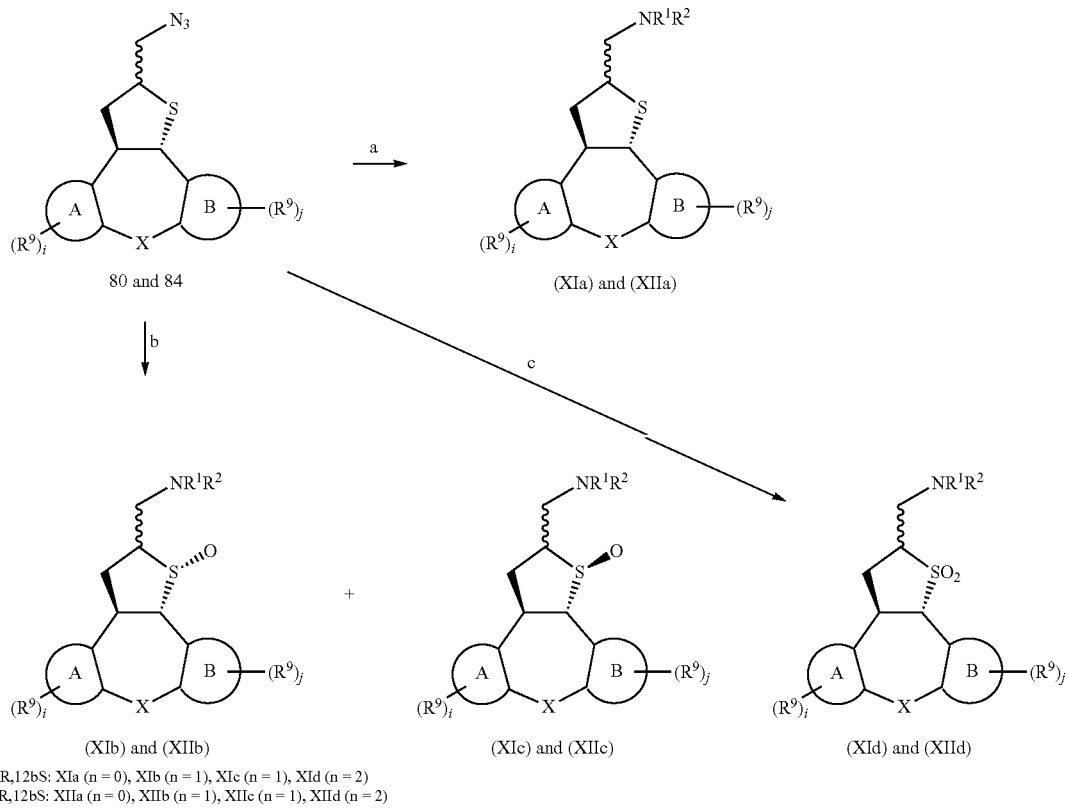

2R,3aR,12bS: XIa (n = 0), XIb (n = 1), XIc (n = 1), XId (n = 2)
2S,3aR,12bS: XIIa (n = 0), XIIb (n = 1), XIIc (n = 1), XIId (n = 2)

Step a): (i) treatment of an intermediate compound 80 or 84 using a Staudinger reaction or hydrogenation with a palladium-carbon catalyst (1 atm) in a reaction-inert solvent such as MeOH, for example at room temperature; and (ii) reductive amination of the resulting intermediate compound with an aldehyde or ketone;

Step b): (i) treatment of an intermediate compound 80 or 84 with an aqueous hydrogen peroxide, in a reaction-inert solvent such as HFIP, for example at room temperature for about 15 minutes; (ii) treatment of the resulting intermediate compound using a Staudinger reaction or hydrogenation with a palladium-carbon catalyst (1 atm) in a reaction-inert solvent such as MeOH, for example at room temperature; (iii) reductive amination of the resulting intermediate compound with an aldehyde or ketone;

Step c): (i) treatment of an intermediate compound 80 or 84 with mCPBA in a reaction-inert solvent such as $CH_2Cl_2$; (ii) treatment of the resulting intermediate compound using a Staudinger reaction or hydrogenating with a palladium-carbon catalyst (1 atm), in a reaction-inert solvent such as MeOH, for example at room temperature; and (iii) reductive amination of the resulting intermediate compound with an aldehyde or ketone.

The compounds of Formula (I) may also be converted into each other following art-known transformation reactions. For instance, a) a compound of Formula (I), wherein $R^1$ and $R^2$ taken together with the nitrogen atom to which they are attached form a radical of Formula (a-2), may be converted into the corresponding primary amine by treatment with hydrazine or aqueous alkali;

b) a compound of Formula (I), wherein $R^1$ or $R^2$ is trifluoromethylcarbonyl, may be converted into the corresponding primary or secondary amine by hydrolysis with aqueous alkali;

c) a compound of Formula (I), wherein $R^1$ or $R^2$ is $C_{1-6}$ alkyl substituted with $C_{1-6}$ alkylcarbonyloxy may be hydrolyzed into a compound of Formula (I) wherein $R^1$ or $R^2$ is $C_{1-6}$ alkyl substituted with hydroxy;

d) a compound of Formula (I), wherein $R^1$ and $R^2$ are both hydrogen may be mono- or di-N-alkylated to the corresponding amine form;

e) a compound of Formula (I), wherein $R^1$ and $R^2$ are both hydrogen, or $R^1$ or $R^2$ is hydrogen, may be N-acylated to the corresponding amide;

f) a compound of Formula (I) containing a $C_{1-6}$alkyloxycarbonyl group may be hydrolyzed to the corresponding carboxylic acid;

g) a compound of Formula (I) in which $R^9$ is hydrogen, i.e. i and/or j is zero, can be converted to a corresponding alkyloxycarbonyl compound by treatment with an appropriate acylating agent, e.g. the appropriate alkyloxycarbonyl chloride in the presence of butyllithium in hexane using an organic solvent such as tetrahydrofuran; or h) a compound of Formula (I) in which $R^9$ is alkyloxycarbonyl can be converted to a corresponding hydroxymethyl compound by reduction for example with $LiAlH_4$ for example in an organic solvent such as tetrahydrofuran.

The procedures described above can be modified by the use of conventional procedures which will be known to those skilled in the art to provide analogous processes for the preparation of compounds of formula (I).

The starting materials mentioned hereinabove are either commercially available or may be made following art-known procedures. For instance, intermediates 1 may be prepared in accordance with the techniques described in patent specifications WO 03/048146 and WO03/048147 referred to above or by techniques analogous thereto.

Pure stereochemically isomeric forms of the compounds of Formula (I) may be obtained by the application of art-known procedures. Diastereomers may be separated by physical methods such as selective crystallization and chromatographic techniques, e.g. counter-current distribution, liquid chromatography and the like.

The compounds of Formula (I) as prepared in the hereinabove described processes are generally racemic mixtures of enantiomers which can be separated from one another following art-known resolution procedures. The racemic compounds of Formula (I) which are sufficiently basic or acidic may be converted into the corresponding diastereomeric salt forms by reaction with a suitable chiral acid respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The following examples are intended to illustrate and not to limit the scope of the present invention.

EXPERIMENTAL PART

A. Preparation of the Intermediate Compounds

Example A1

(11R)-11-{[(4R)-2,2-dimethyl-1,3-dioxolan-4-yl]methyl}-8-fluoro-5,11-dihydro-10H-dibenzo[a,d]cyclohepten-10-one (Intermediate 2)

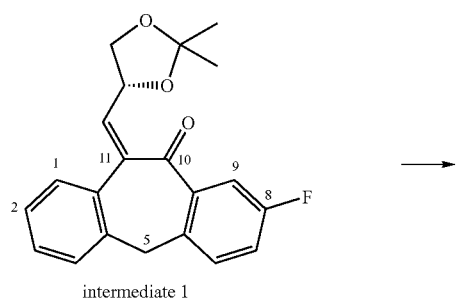

intermediate 1

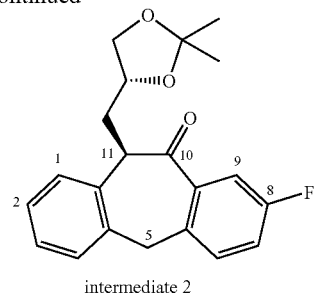

intermediate 2

A solution of α,β-unsaturated ketone intermediate 1 (1.00 g, 2.96 mmol) and Et$_3$N (0.63 mL, 4.50 mmol) in i-PrOH (30 mL) was hydrogenated with 10% Pd/C at atmospheric pressure for 6 hour. Then the mixture was filtered through a pad of celite and the solids were washed with CH$_2$Cl$_2$ (4×20 mL). After evaporation, i-PrOH (5 mL) and Et$_3$N (1.20 mL) was added and the reaction mixture was stirred at 40° C. for 1 hour. The reaction mixture was cooled to room temperature and allowed to crystallize. The crystals were filtered off and dried under vacuum to afford pure ketone intermediate 2 as a white crystalline powder (0.86 g, 86%); mp: 144-146° C.

Mass spectrum: CI m/z (assignment, relative intensity) 341 (MH$^+$, 2%), 283 (MH$^+$-acetone, 100%); EI: m/z (assignment, relative intensity) 340 (M$^+$·, 1%), 282 (M$^+$·-acetone, 79%), 226 (M$^+$·-sidechain+H, 100%); High resolution EI, Calculated C$_{21}$H$_{21}$FO$_3$ (M$^+$·): 340.1475, Found: 340.1479 (1%).

Example A2

(10R,11R)-11-{[(4R)-2,2-dimethyl-1,3-dioxolan-4-yl]methyl}-8-fluoro-10,11-dihydro-5H-dibenzo[a,d]cyclohepten-10-ol (Intermediate 3)

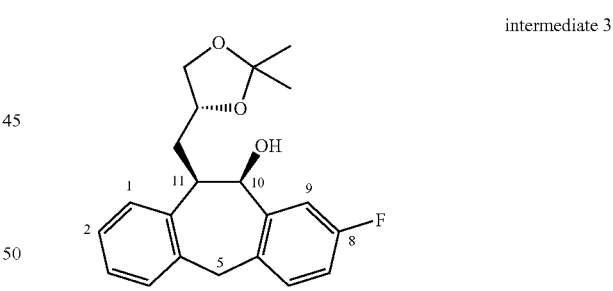

intermediate 3

To an ice-cooled solution of ketone intermediate 2 (0.42 g, 1.23 mmol) in i-PrOH (15 mL) was added phosphate buffer solution (pH=7, 5 mL) and then portionwise NaBH$_4$ (0.23 g, 6.16 mmol). The reaction mixture was stirred at room temperature for 1 hour. Then 10 mL NH$_4$Cl (sat. aq. solution) was added, the mixture was extracted with CH$_2$Cl$_2$ (3×15 mL) and the organic phases were dried with MgSO$_4$. After removal of the solvent, the residue was purified on a silica gel column by using ether/hexane (40:60), yielding intermediate 3 as a colorless oil (0.42 g, 99%).

Mass spectrum: CI m/z (assignment, relative intensity) 325 (MH$^+$—H$_2$O, 53%), 267 (MH$^+$—H$_2$O-acetone, 100%), 249 (MH$^+$-2H$_2$O-acetone, 97%); EI: m/z (assignment, relative intensity) 342 (M$^+$·, 3%), 324 (M$^+$·—H$_2$O, 48%), 266 (M$^+$·

—H₂O-acetone, 35%), 209 (100%); High resolution EI Calculated C₂₁H₂₃FO₃ (M⁺·): 342.1631, Found: 342.1627 (5%).

Example A3

(4R)-4-{[(10R,11S)-11-azido-2-fluoro-10,11-dihydro-5H-dibenzo[a,d]cyclohepten-10-yl]methyl}-2,2-dimethyl-1,3-dioxolane (Intermediate 4)

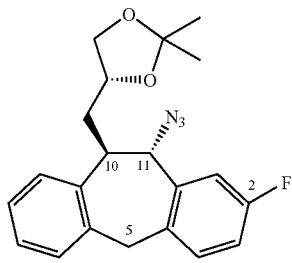

intermediate 4

To a cooled (−30° C.) solution of DIAD (2.43 mL, 33.47 mmol) in THF (10 mL) were added intermediate alcohol 3 (2.30 g, 6.73 mmol) in THF (18 mL) and Ph₃P (3.71 g, 14.07 mmol). After 20 minutes, diphenyl phosphoryl azide (DPPA) (3.62 mL, 16.83 mmol) was added and the reaction mixture was allowed to warm up to room temperature. After stirring overnight, the solvent was removed in vacuo to give a red oil. The crude material was purified by column chromatography using ether/hexane (10/90) to give an unseparated mixture of intermediate 4, as an oil, and Ph₃PO (3.46 g).

Mass spectrum: CI m/z (assignment, relative intensity) 368 (MH⁺, 1%), 325 (MH⁺—HN₃, 9%), 304 (13%), 276 (MH⁺—HN₃-acetone, 100%), 248 (20%).

Example A4

(2R)-3-[(10R,11S)-11-azido-2-fluoro-10,11-dihydro-5H-dibenzo[a,d]cyclohepten-10-yl]-1,2-propanediol (Intermediate 5)

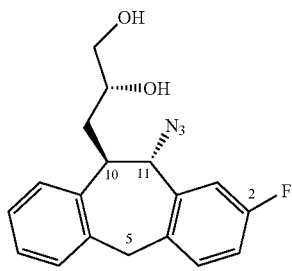

intermediate 5

To solution of azide intermediate 4 (3.68 g, 10.02 mmol) in THF (30 mL) was added 1N HCl (30 mL) and the mixture was stirred at room temperature for 8 hours. Add K₂CO₃ (sat. aq. sol.) at 0° C., extract 3 times with CH₂Cl₂ and dry with MgSO₄. The residue obtained upon evaporation was purified by column chromatography on silica gel using Et₂O/heptane (30/70) to give an oily intermediate 5 (3.19 g, 91% for 2 steps from 3).

Mass spectrum: CI m/z (assignment, relative intensity) 328 (MH⁺, 2%), 310 (MH⁺—H₂O, 2%), 300 (MH⁺—N₂, 5%), 285 (MH⁺—HN₃, 11%), 267 (MH⁺—HN₃—H₂O, 100%), 249 (MH⁺—HN₃-2H₂O, 33%), 225 (MH⁺—HN₃—CH₂OHCHO, 20%).

Example A5

(2R)-3-[(10R,11S)-11-azido-2-fluoro-10,11-dihydro-5H-dibenzo[a,d]cyclohepten-10-yl]-2-hydroxypropyl 4-methylbenzenesulfonate (Intermediate 6)

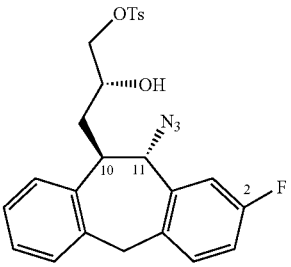

intermediate 6

To solution of diol intermediate 5 (1.11 g, 3.39 mmol) in dry toluene (10 mL) was added Bu₂SnO (97.6 mg, 0.39 mmol), Et₃N (1.07 mL, 7.74 mmol) and TsCl (0.739 g, 3.87 mmol). The mixture was stirred at room temperature overnight. Add NH₄Cl (sat. aq. sol.), extract 3 times with CH₂Cl₂ and dry with MgSO₄. The residue was purified by column chromatography on silica gel using EtOAc/heptane (20/80) to give intermediate 6 as an oil (1.55 g, 95%).

Mass spectrum: —CI m/z (assignment, relative intensity) 454 (MH⁺—N₂, 1%), 421 (MH⁺—HN₃—H₂O, 1%), 282 (MH⁺-TsOH—HN₃, 20%), 264 (MH⁺-TsOH—HN₃—H₂O, 15%), 173 (TsOH₂⁺, 100%).

Example A6

(2R)-1-azido-3-[(10R,11S)-11-azido-2-fluoro-10,11-dihydro-5H-dibenzo[a,d]cyclohepten-10-yl]-2-propanol (Intermediate 7)

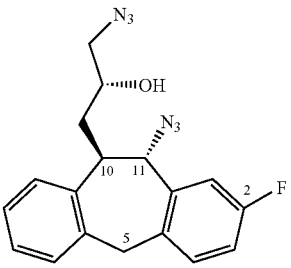

intermediate 7

A solution of tosylate intermediate 6 (2.00 g, 4.15 mmol) in DMF (30 mL) was treated with sodium azide (810.8 mg, 12.47 mmol) and the mixture was stirred at 90° C. in the dark for 2 hours. The reaction mixture was diluted with water and extracted with CH₂Cl₂. The combined extracts were washed with brine. Following concentration of the dried organic phases the residue was purified by column chromatography on silica gel using heptane/EtOAc (80/20) affording diazide intermediate 7 (1.22 g, 88%) as an oil.

Mass spectrum: —CI m/z (assignment, relative intensity) 325 (MH⁺—N₂, 2%), 310 (MH⁺—HN₃, 3%), 297 (MH⁺—N₂—N₂, 1%), 282 (MH⁺—HN₃—N₂, 52%), 268 (MH⁺—HN₃—HN₃, 3%).

Example A7

(1R)-2-azido-1-{[(10R,11S)-11-azido-2-fluoro-10,11-dihydro-5H-dibenzo[a,d]cyclohepten-10-yl]methyl}ethyl methanesulfonate (Intermediate 8)

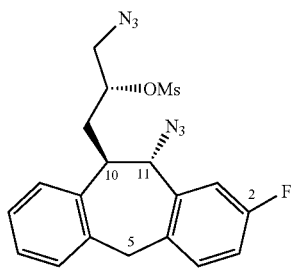

intermediate 8

To solution of diazide intermediate 7 (65 mg, 0.18 mmol) in CH₂Cl₂ (10 mL) was added DMAP (18.5 mg, 0.09 mmol), Et₃N (0.13 mL, 0.63 mmol) and MsCl (44.5 µL, 0.40 mmol). After stirring at room temperature for 10 minutes, 10 mL NH₄Cl (sat. aq. solution) was added. Extract with CH₂Cl₂ (3×10 mL) and dry with MgSO₄. Column purification on silica gel using EtOAc/heptane (20:80) yielded intermediate 8 as an oil (78.2 mg, 98%).

Mass spectrum: —CI m/z (assignment, relative intensity) 403 (MH⁺—N₂, 3%), 360 (MH⁺—N₂—HN₃, 43%), 307 (MH⁺-MeSO₃H—N₂, 50%), 264 (MH⁺-MeSO₃H—HN₃—N₂, 58%), 250 (MH⁺-MeSO₃H—HN₃, —N₃, 21%), 197 (100%).

Example A8

[(2S,3aR,12bS)-11-fluoro-1,2,3,3a,8,12b-hexahydrodibenzo[3,4:6,7]cyclohepta[1,2-b]pyrrol-2-yl]methanamine (Intermediate 9)

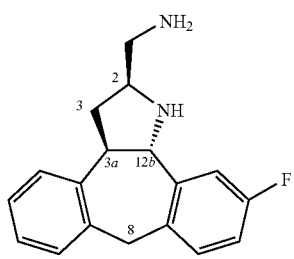

intermediate 9

A solution of diazide intermediate 8 (98.2 mg, 0.23 mmol) in MeOH (10 mL) was hydrogenated at atmospheric pressure with 10% Pd/C for 1 night. Then the mixture was filtered through a pad of celite and the solids were washed 4 times with CH₂Cl₂. After evaporation of the filtrate, the crude product was purified by column chromatography on silica gel using CHCl₃/MeOH/NH₄OH (90/9/1). This afforded intermediate 9 as an oil (36.4 mg, 56%).

Example A9

(1S)-2-azido-1-{[(10R,11S)-11-azido-2-fluoro-10,11-dihydro-5H-dibenzo[a,d]cyclohepten-10-yl]methyl}ethyl 4-nitrobenzoate (Intermediate 10)

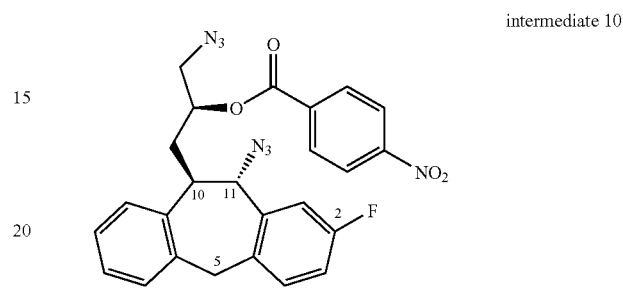

intermediate 10

To a cooled (0° C.) solution of DIAD (4.2 mL, 21.18 mmol) in THF (50 mL) was added Ph₃P (5.55 g, 21.18 mmol). Stir at 0° C. for 30 minutes (precipitation of white solid). Then, a mixture of alcohol intermediate 7 (3.727 g, 10.59 mmol) and 4-nitrobenzoic acid (3.54 g, 21.18 mmol) in THF (50 mL) was added. The reaction mixture was allowed to warm up to room temperature and after stirring for 2 hours, MeOH was added and the stirring continued for an additional 30 minutes. After removal of the solvent, the crude material was purified by column chromatography using EtOAc/heptane (20/80) to give the ester intermediate 10 as an oil (4.85 g, 91%).

Mass spectrum: —CI m/z (assignment, relative intensity) 431 (MH⁺—N₂—HN₃, 36%), 307 (MH⁺—N₂-p-NO₂PHCO₂H, 2%), 264 (MH⁺-p-NO₂PHCO₂H—HN₃—N₂, 58%), 197 (100%), 182 (72%).

Example A10

(2S)-1-azido-3-[(10R,11S)-11-azido-2-fluoro-10,11-dihydro-5H-dibenzo[a,d]cyclohepten-10-yl]-2-propanol (Intermediate 11)

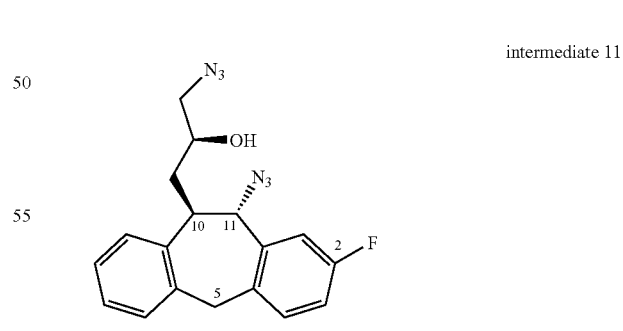

intermediate 11

A solution of the above diazide intermediate 10 (78.0 mg, 0.15 mmol) in MeOH (2 mL) was treated with K₂CO₃ (76.9 mg, 0.47 mmol) and the mixture was stirred for 1 hour. Add NH₄Cl (sat. aq. sol.), extract 3 times with CH₂Cl₂ and dry with MgSO₄. The residue was purified by column chromatography on silica gel using EtOAc/heptane (20/80) to give alcohol intermediate 11 as an oil (42.6 mg, 78%).

Mass spectrum: —CI m/z (assignment, relative intensity) 325 (MH$^+$—N$_2$, 2%), 310 (MH$^+$—HN$_3$, 3%), 297 (MH$^+$—N$_2$—N$_2$, 1%), 282 (MH$^+$—HN$_3$—N$_2$, 52%), 268 (MH$^+$—HN$_3$—N$_3$, 3%).

Example A11

(1S)-2-azido-1-{[(10R,11S)-11-azido-2-fluoro-10,11-dihydro-5H-dibenzo[a,d]cyclohepten-10-yl]methyl}ethyl methanesulfonate (Intermediate 12)

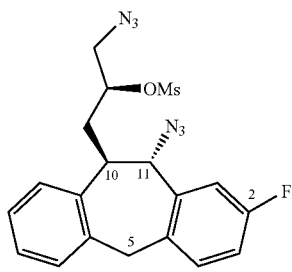

intermediate 12

To a solution of diazide intermediate 11 (42.6 mg, 0.12 mmol) in CH$_2$Cl$_2$ (5 mL) was added DMAP (12.7 mg, 0.06 mmol), Et$_3$N (0.047 mL, 0.42 mmol) and MsCl (33.9 μL, 0.30 mmol). Stir at room temperature for 10 minutes. Add 10 mL NH$_4$Cl (sat. aq. solution), extract with CH$_2$Cl$_2$ (3×10 mL) and dry with MgSO$_4$; upon evaporation of the solvent intermediate 12 was obtained as an oil (53.0 mg, 100%).

Mass spectrum: —CI m/z (assignment, relative intensity) 403 (MH$^+$—N$_2$, 3%), 360 (MH$^+$—N$_2$—HN$_3$, 43%), 307 (MH$^+$-MeSO$_3$H—N$_2$, 50%), 264 (MH$^+$-MeSO$_3$H—HN$_3$—N$_2$, 58%), 250 (MH$^+$-MeSO$_3$H—HN$_3$—N$_3$, 21%), 197 (100%).

Example A12

[(2R,3aR,12bS)-11-fluoro-1,2,3,3a,8,12b-hexahydrodibenzo[3,4:6,7]cyclohepta[1,2-b]pyrrol-2-yl]methanamine (Intermediate 13)

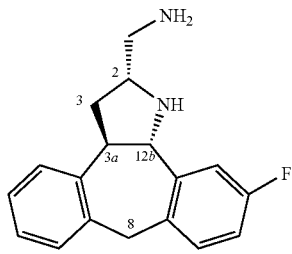

intermediate 13

A solution of diazide intermediate 12 (501.0 mg, 1.16 mmol) in MeOH (10 mL) was hydrogenated under 1 atmospheric pressure with 10% palladium-on-charcoal under vigorous stirring at room temperature for 1 night. Then the mixture was filtered through a pad of celite and the solids were washed 4 times with CH$_2$Cl$_2$. After evaporation, the crude product was purified by column chromatography on silica gel using CHCl$_3$/MeOH/NH$_4$OH (90/9/1). This yielded intermediate 13 as an oil (270.0 mg, 82%).

Example A13

Benzyl[(2S,3aR,12bS)-11-fluoro-1,2,3,3a,8,12b-hexahydrodibenzo[3,4:6,7]cyclohepta[1,2-b]pyrrol-2-yl]methylcarbamate (Intermediate 14)

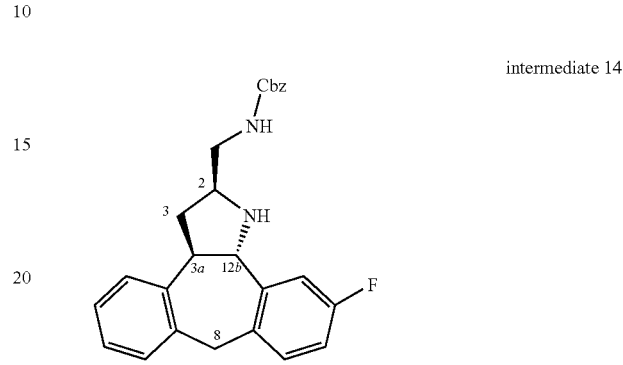

intermediate 14

To a solution of diamine intermediate 9 (220.0 mg, 0.78 mmol) in CH$_2$Cl$_2$ (5 mL) at −20° C. was added Et$_3$N (0.109 mL, 0.78 mmol) and benzyl chloroformate (0.112 mL, 0.78 mmol). The mixture was then stirred for 1 hour. Add 10 mL of NH$_4$Cl (sat. aq. solution), extract with CH$_2$Cl$_2$ (3×10 mL) and dry with MgSO$_4$. The residue was purified by column chromatography on silica gel using EtOAc/heptane (20/80) to give a mono-Cbz intermediate 14 (128.9 mg, 40%) and di-Cbz derivative (84.5 mg).

Mass spectrum: —CI m/z (assignment, relative intensity) 417 (MH$^+$, 100%), 397 (MH$^+$—HF, 8%), 311 (MH$^+$-PhCHO, 7%), 309 (MH$^+$—PHCH$_2$OH, 32%), 283 (16%), 252 (MH$^+$-PhCH$_2$OCONHCH$_3$, 24%).

Example A14

Benzyl[(2S,3aR,12bS)-1-(bromoacetyl)-11-fluoro-1,2,3,3a,8,12b-hexahydro dibenzo[3,4:6,7]cyclohepta[1,2-b]pyrrol-2-yl]methylcarbamate (Intermediate 15)

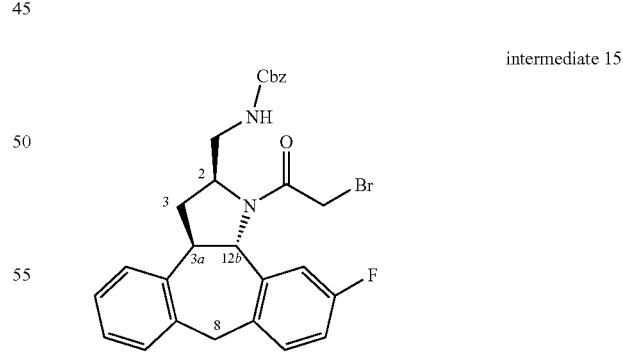

intermediate 15

To a solution of monoCbz intermediate 14 (32.5 mg, 0.078 mmol) in EtOAc (3 mL) was added 1 mL of NaOH (sat. aq. solution) and bromoacetyl bromide (6.8 μL, 0.078 mmol). The two phases were stirred vigorously for 1 night. Add 10 mL of NH$_4$Cl (sat. aq. solution), extract with CH$_2$Cl$_2$ (3×10 mL) and dry with MgSO$_4$. Column purification on silica gel using EtOAc/heptane (20/80) gave intermediate 15 as an oil (31.4 mg, 62%).

Mass spectrum: —CI m/z (assignment, relative intensity) 457 (MH⁺—HBr, 3%), 413 (MH⁺—HBr—CO₂, 1%), 365 (MH⁺—HBr-PhCH₃ 1%), 351 (MH⁺-PhCHO—HBr, 2%), 323 (MH⁺—HBr-PhCHO—CO, 5%), 119 (8%), 91 (100%).

Example A15

Benzyl(5aS,14bR,15aS)-7-fluoro-4-oxo-1,3,4,5a,10,14b, 15,15a-octahydro-2H-dibenzo[3',4':6',7']cyclohepta[1',2':4, 5]pyrrolo[1,2-a]pyrazine-2-carboxylate (Intermediate 16)

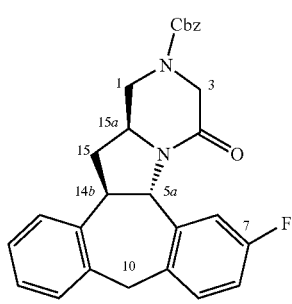

intermediate 16

To a solution of the above carbamate intermediate 15 (91.7 mg, 0.17 mmol) in DMF (5 mL) was added K₂CO₃ (103.0 mg, 0.75 mmol) and the mixture was stirred at room temperature for 36 hours. Add 10 mL of NH₄Cl (sat. aq. solution), extract with CH₂Cl₂ (3×10 mL) and dry with MgSO₄. Column purification on silica gel using EtOAc/heptane (30/70) gave polycyclic intermediate 16 (86.2 mg, 92%) as an oil.

Mass spectrum: —CI m/z (assignment, relative intensity) 457 (MH⁺, 1%), 323 (MH⁺—PhCHO—CO, 5%), 279 (MH⁺—Cbz-CH₂CO, 1%), 91 (10%).

Example A16

N-{[(2R,3aR,12bS)-11-fluoro-1,2,3,3a,8,12b-hexahydrodibenzo[3,4:6,7]cyclohepta[1,2-b]pyrrol-2-yl]methyl}(triphenyl)methanamine (Intermediate 17)

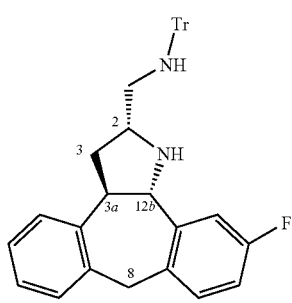

intermediate 17

To an ice cooled solution of diamine 13 (41.6 mg, 0.15 mmol) in CH₂Cl₂ (5 mL) was added Et₃N (42.5 μL, 0.3 mmol), DMAP (9.4 mg, 0.07 mmol) and trityl chloride (46.1 mg, 0.16 mmol). The mixture was then stirred at 0° C. for 2 hours. Add 10 mL of NH₄Cl (sat. aq. solution), extract with CH₂Cl₂ (3×10 mL) and dry with MgSO₄. Column purification on silica gel using EtOAc/heptane (20/80) gave a crystalline intermediate 17 (52.6 mg, 68%); mp: 58-60° C.

Mass spectrum: -APCI m/z (assignment, relative intensity) 525 (MH⁺, 38%), 390 (4%), 283 (MH⁺-(Tr-H), 15%), 252 (MH⁺—CH₃NHTr, 27%), 243 (Tr⁺, 100%), 228 (7%), 165 (29%).

Example A17

N-{[(2R,3aR,12bS)-1-(bromoacetyl)-11-fluoro-1,2, 3,3a,8,12b-hexahydrodibenzo[3,4:6,7]cyclohepta[1, 2-b]pyrrol-2-yl]methyl}(triphenyl)methanamine (Intermediate 18)

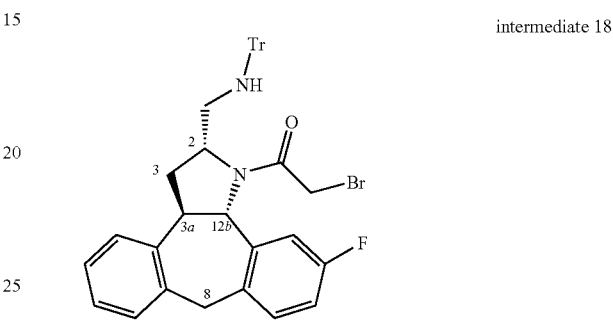

intermediate 18

The diamine intermediate 17 (26.7 mg, 0.05 mmol) was added to a two-phase system consisting of 2 mL CH₂Cl₂ and 0.5 mL Na₂CO₃ (aq. sat. solution), and the mixture was stirred for 10 minutes. After adding bromoacetyl bromide (6.8 μL, 0.08 mmol) the two phases were stirred vigorously for 3 hours. Extract with CH₂Cl₂ (3×10 mL) and dry with MgSO₄. Column purification on silica gel using EtOAc/heptane (20/80) gave intermediate 18 as an oil (27.9 mg, 85%) characterised as a mixture of two conformers.

Mass spectrum: -APCI m/z (assignment, relative intensity) 645 (MH⁺, 39%), 601 (3%), 403 (MH⁺-(Tr-H), 7%), 321 (MH⁺-TrH—HBr, 21%), 243 (Tr⁺, 100%), 228 (3%), 165 (15%).

Example A18

N-{[(2R,3aR,12bS)-11-fluoro-1-(methoxyacetyl)-1, 2,3,3a,8,12b-hexahydrodibenzo-[3,4:6,7]cyclohepta [1,2-b]pyrrol-2-yl]methyl}(triphenyl)methanamine (Intermediate 19)

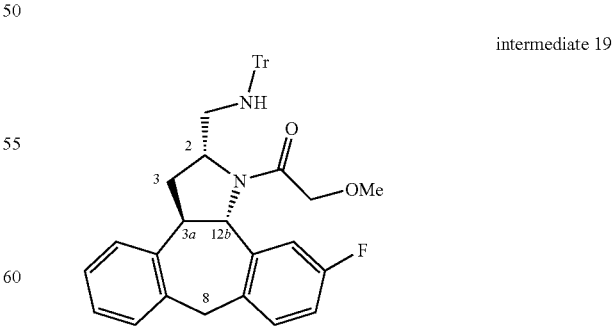

intermediate 19

To a solution of intermediate 18 (530 mg, 0.82 mmol) in MeOH (15 mL) was added MeSO₃H (3 mL) and the mixture was stirred at 60° C. for 30 minutes. After complete evaporation of the solvent, the residue was dissolved in CH₂Cl₂/

$K_2CO_3$ (sat. aq. solution) (15/15 mL) and the organic layer was separated. The aqueous layer was extracted with $CH_2Cl_2$ (3×10 mL) and the combined organic layers were then dried with $MgSO_4$. Column purification on silica gel using EtOAc/heptane (20/80) gave intermediate 19 as an oil (231.3 mg, 47%), characterised as a mixture of two conformers.

Mass spectrum: -APCI m/z (assignment, relative intensity) 598 ($MH^+$, 1%), 519 (2%), 355 ($MH^+$-Tr, 13%), 283 ($MH^+$-Tr-CO=CHOMe, 2%), 271 (10%), 243 ($Tr^+$, 100%), 167 (21%).

Example A19

[(2R,3aR,12bS)-1-(bromoacetyl)-11-fluoro-1,2,3,3a,8,12b-hexahydrodibenzo[3,4:6,7]cyclohepta[1,2-b]pyrrol-2-yl]methylformamide (Intermediate 20)

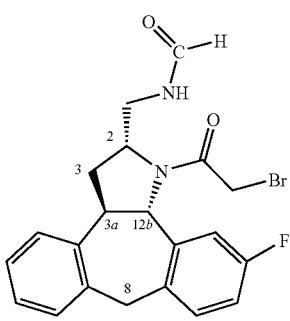

intermediate 20

The N-Tr protected amine intermediate 18 (100 mg, 0.15 mmol) was dissolved in 98% formic acid (2 mL) and the mixture was stirred at room temperature for 24 hours. After removal of excess of formic acid in vacuo, the residue was dissolved in $CHCl_3$ (2 mL) and EEDQ (47 mg, 0.19 mmol) was added. The solution was stirred at room temperature for 5 hours. Following evaporation of the solvent, the residue was purified by column chromatography on silica gel using $CH_2Cl_2$/MeOH (98/2) as eluent. The N—CHO protected amine intermediate 20 (54.7 mg, 82%) was obtained as an oil.

Mass spectrum: —CI m/z (assignment, relative intensity) 431, 433 ($MH^+$, 42%), 353 ($MH^+$—HBr, 100%), 294 ($MH^+$—HBr—$CH_3NHCHO$, 9%), 249 (4%), 158 (2%), 130 (7%).

Example A20

(5aS,14bR,15aR)-7-fluoro-4-oxo-1,3,4,5a,10,14b,15,15a-octahydro-2H-dibenzo[3',4':6',7']cyclohepta[1',2':4,5]pyrrolo[1,2-a]pyrazine-2-carbaldehyde (Intermediate 21)

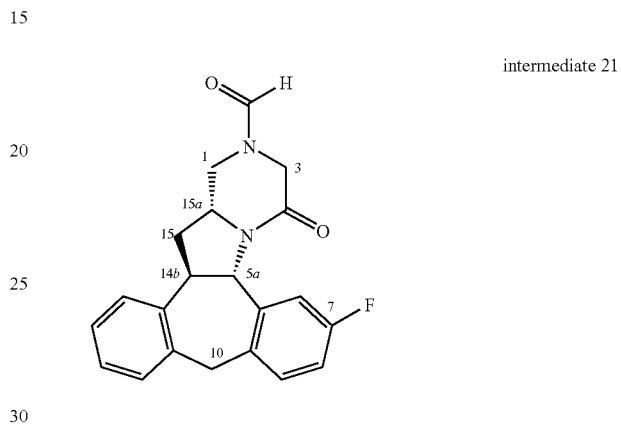

intermediate 21

To a solution of N-formyl protected amine intermediate 20 (91 mg, 0.21 mmol) in dry THF (10 mL) was added a solution of t-BuOK (30.3 mg, 0.24 mmol) in THF (2 mL). The reaction mixture was stirred at room temperature for 30 minutes. Water (10 mL) was then added and the mixture extracted with $CH_2Cl_2$ (10 mL). Column purification on silica gel using $CH_2Cl_2$/MeOH (97/3) gave the cyclic intermediate 21 (47.4 mg, 64%) as an oil.

Mass spectrum: —CI m/z (assignment, relative intensity) 351 ($MH^+$, 100%), 331 ($MH^+$—HF, 5%), 323 ($MH^+$—CO, 6%), 319 (8%), 219 (2%), 130 (4%).

Example A21

(10R,11R)-11-{[(4R)-2,2-dimethyl-1,3-dioxolan-4-yl]methyl}-8-fluoro-10,11-dihydro-5H-dibenzo[a,d]cyclohepten-10-yl acetate (Intermediate 22)

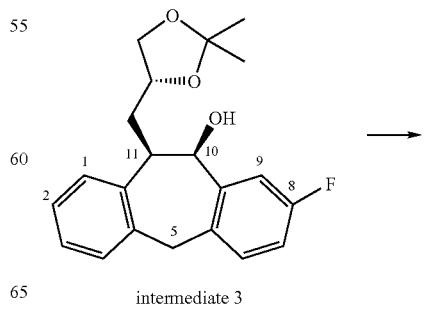

intermediate 3

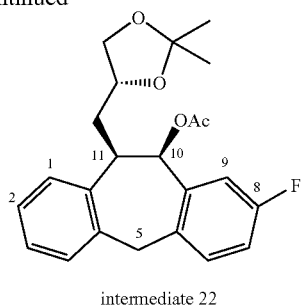

intermediate 22

To a solution of the alcohol intermediate 3 (0.42 g, 1.23 mmol) in CH$_2$Cl$_2$ (30 mL) was added Et$_3$N (0.43 mL, 3.07 mmol), DMAP (0.15 g, 1.23 mmol) and AcOH anhydride (0.29 mL, 3.07 mmol). Stir at room temperature for 1 hour, add NH$_4$Cl (sat. aq. solution, 20 mL), extract with CH$_2$Cl$_2$ (3×15 mL) and dry with MgSO$_4$. Column purification on silica gel using ether/hexane (30:70) gave a white crystalline intermediate 22 (0.45 g, 95%); mp: 147-149° C.

Mass spectrum: —CI m/z (assignment, relative intensity) 385 (MH$^+$, 1%), 325 (MH$^+$-AcOH, 100%), 267 (MH$^+$-AcOH-acetone, 43%), 249 (MH$^+$-AcOH-acetone-H$_2$O, 47%); -EI: m/z (assignment, relative intensity) 324 (M$^{+\cdot}$-AcOH, 46%), 266 (M$^{+\cdot}$-AcOH-acetone, 20%), 209 (M$^{+\cdot}$-AcOH-sidechain, 100%); High resolution EI Calculated C$_{22}$H$_{21}$FO$_2$ (M$^{+\cdot}$-AcOH): 324.1526, Found: 324.1521 (M$^{+\cdot}$, 72%).

Example A22

(10R,11R)-11-[(2R)-2,3-dihydroxypropyl]-8-fluoro-10,11-dihydro-5H-dibenzo-[a,d]cyclohepten-10-yl acetate (Intermediate 23)

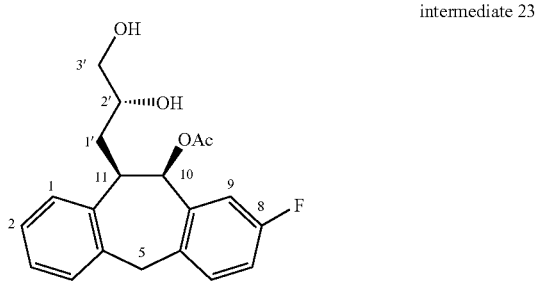 [SMILES: CC(=O)O[C@H]1c2cc(F)ccc2Cc2ccccc2[C@H]1C[C@@H](O)CO]

intermediate 23

To a solution of the acetal intermediate 22 (0.45 g, 1.17 mmol) in THF (10 mL) was added 1N HCl (10 mL). After stirring at room temperature for 8 hours, 10 mL Na$_2$CO$_3$ (sat. aq. solution) was added at 0° C. Extract with CH$_2$Cl$_2$ (3×10 mL) and dry with MgSO$_4$. Column purification on silica gel using EtOAc/hexane (70:30) gave diol intermediate 23 as a colorless oil (0.39 g, 96%).

Mass spectrum: —CI m/z (assignment, relative intensity) 345 (MH$^+$, 1%), 327 (MH$^+$—H$_2$O, 3%), 309 (MH$^+$-2H$_2$O, 3%), 285 (MH$^+$-AcOH, 17%), 267 (MH$^+$-AcOH—H$_2$O, 100%), 249 (MH$^+$-AcOH 2H$_2$O, 3%); EI: m/z (assignment, relative intensity) 326 (M$^{+\cdot}$—H$_2$O, 10%), 284 (M$^{+\cdot}$-AcOH, 13%), 209 (M$^{+\cdot}$-AcOH-sidechain, 100%)); High resolution EI Calculated C$_{20}$H$_{19}$FO$_3$(M$^{+\cdot}$—H$_2$O): 326.1318, Found: 326.1316 (31%).

Example A23

(10R,11R)-11-[(2S)-2,3-diazidopropyl]-8-fluoro-10,11-dihydro-5H-dibenzo[a,d]cyclohepten-10-yl acetate (Intermediate 24)

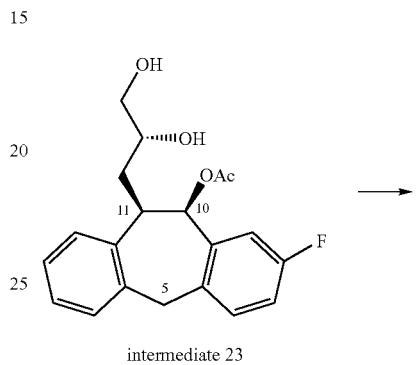

intermediate 24

To the acetate diol intermediate 23 (0.59 g, 1.72 mmol) in CH$_2$Cl$_2$ (15 mL) was added Et$_3$N (0.96 mL, 6.86 mmol), DMAP (209 mg, 1.72 mmol) and MeSO$_2$Cl (0.53 mL, 6.86 mmol) at 0° C. Stir at room temperature for 1 hour. Work it up by adding NH$_4$Cl (sat. aq. sol.), extract 3 times with CH$_2$Cl$_2$ and dry with MgSO$_4$. Column purification on silica gel using EtOAc/heptane (50/50) afforded dimesyl compound as an oil (0.84 g, 98%). To this compound (182.5 mg, 0.36 mmol) in DMF (10 mL) was added NaN$_3$ (95 mg, 1.46 mmol). The reaction mixture was heated at 80° C. for 3 hours. After cooling, add NH$_4$Cl (sat. aq. sol.), extract 3 times with CH$_2$Cl$_2$ and dry with MgSO$_4$. After evaporation the residue was purified on silica gel using EtOAc/heptane (20/80) to give intermediate 24 as an oily product (122.3 mg, 85%).

Example A24

(4S)-4-{[(10R,11R)-2-fluoro-11-hydroxy-10,11-dihydro-5H-dibenzo[a,d]-cyclohepten-10-yl]methyl}-2-imidazolidinone (Intermediate 25)

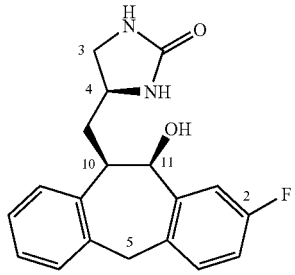

intermediate 25

Diazide intermediate 24 was converted via diazido alcohol intermediate 24a into a diamine which was further converted into intermediate 25. To a solution of diazide 24 (120.1 mg, 0.30 mmol) in MeOH (10 mL) was added $K_2CO_3$ (126.4 mg, 0.91 mmol). The reaction mixture was stirred at room temperature for 1 hour. Add $NH_4Cl$ (sat. aq. sol.), extract 3 times with $CH_2Cl_2$. Column purification on silica gel using $Et_2O$/heptane (40/60) gave the diazido alcohol intermediate 24a as an oily product (77.5 mg, 72%). This compound (75 mg, 0.21 mmol) in MeOH (5 mL) was hydrogenated at 1 atmospheric pressure with 10% palladium-on-charcoal under vigorous stirring at room temperature for 1 night. Then the mixture was filtered through a pad of celite and the solids were washed 4 times with $CH_2Cl_2$. After evaporation of the solvent, the crude product was dissolved in 5 mL of $CH_3CN$ and $Et_3N$ (34 μL, 0.24 mmol) was added. The reaction mixture was heated under argon at 70° C. After 1 hour, a solution of diphenyl carbonate (23 mg, 0.11 mmol) in $CH_3CN$ was added dropwise and the mixture was stirred at 70° C. for 1 day. After evaporation, the crude product was purified by column chromatography on silica gel using $CHCl_3$/MeOH (90/10) to give the imidazolidinone intermediate 25 as an oil (34.4 mg, 48%).

Example A25

(11E)-11-{[(4R)-2,2-dimethyl-1,3-dioxolan-4-yl]methylene}-8-fluorodibenzo[b,f]oxepin-10(11H)-one (Intermediate 27)

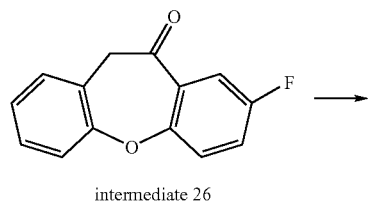

intermediate 26

-continued

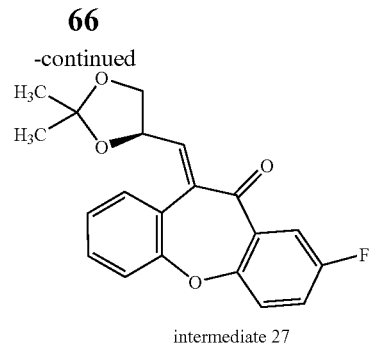

intermediate 27

To a suspension of intermediate 26 (0.228 g, 1 mmol) and $MgBr_2$ (0.202 g, 1.1 mmol) in dry toluene (5 mL), (S)-glyceraldehyde acetonide (4 mmol, 1.5 M solution in THF) and tBuOK (22.4 mg, 0.2 mmol) was added and stirred for 3 hours at room temperature. A saturated aq. $NH_4Cl$ solution (5 mL) was added, the organic layer was separated and kept over anhydrous $MgSO_4$. The solvent was removed under reduced pressure followed by the separation of α,β-unsaturated product by flash chromatography using EtOAc:heptane (1:9) as an eluant to obtain intermediate 27 as a yellow liquid in a ratio of 85/15 E and Z isomer (85%, 0.289 g).

HRMS: Calculated 340.1111; found 340.1122

Example A26 a) (10R,11R)-11-{[(4R)-2,2-dimethyl-1,3-dioxolan-4-yl]methyl}-8-fluoro-10,11-dihydrodibenzo[b,f]oxepin-10-ol (Intermediate 29)

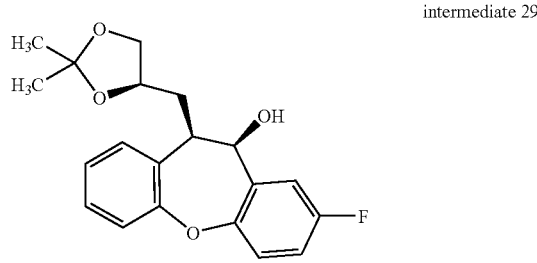 [SMILES: CC1(C)OC[C@@H](C[C@@H]2c3ccccc3Oc3ccc(F)cc3[C@@H]2O)O1]

intermediate 29

To a solution of intermediate 27 (0.340 g, 1 mmol) in i-PrOH (5 mL) was added $Et_3N$ (0.21 mL, 1.5 mmol) and the reaction mixture was hydrogenated under atmospheric pressure using 10% Pd/C (40 mg) as a catalyst. After completion of the reaction (4 hours) the reaction mixture was passed through a small pad of celite and further washed with $CH_2Cl_2$ (2×5 mL) followed by the evaporation of the solvent to obtain crude ketone intermediate 28.

intermediate 28

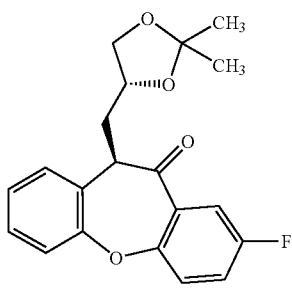

b) The crude intermediate 28 thus obtained was dissolved in i-PrOH (10 mL) and aqueous phosphate buffer solution (3 mL, pH 7) was added to it. The temperature was lowered to 0° C. and NaBH$_4$ (0.152 g, 4 mmol) was added to it in several lots and then allowed to stir further for 15 minutes at the same temperature. Aq. NH$_4$Cl solution (5 mL) was added and the reaction mixture was extracted using Et$_2$O (3×5 mL). After drying over anhydrous MgSO$_4$ the solvent was removed under reduced pressure and the two diastereomeric alcohols (1:1) with slightly different polarity were separated by flash chromatography using EtOAc:heptane (20:80) as an eluant to obtain the more polar cis-alcohol intermediate 29 as a white solid (mp: 59-61° C.; 49%, 0.16 g).

HRMS: Calculated 344.1424; found 344.1435

Example A27

(10S,11R)-11-{[(4R)-2,2-dimethyl-1,3-dioxolan-4-yl]methyl}-8-fluoro-10,11-dihydrodibenzo[b,f]oxepin-10-yl azide (Intermediate 30)

intermediate 30

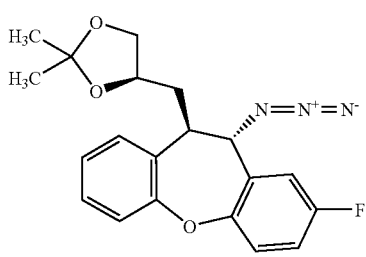

To a solution of P(Ph)$_3$ (0.524 g, 2 mmol) in dry THF (5 mL) at −15° C., a solution of DIAD (0.424 g, 2.1 mmol) in THF (2 mL) was added and the resulting complex was stirred for 20 minutes followed by the addition of intermediate 29 (0.329 g, 1 mmol) dissolved in THF (2 mL) and a solution of DPPA (0.330 g, 1.2 mmol) in THF (1 mL). The reaction mixture was warmed to room temperature and stirred for 18 hours. After addition of MeOH the reaction mixture was dried under vacuum followed by separation of the azide using flash chromatography employing EtOAc:heptane (1:9) as an eluant to obtain intermediate 30 as a colourless liquid (91%, 0.335 g)

HRMS: Calculated 369.1489; found 369.1483. .

Example A28

(2R)-3-[(10R,11S)-11-azido-2-fluoro-10,11-dihydrodibenzo[b,f]oxepin-10-yl]-1,2-propanediol (Intermediate 31)

intermediate 31

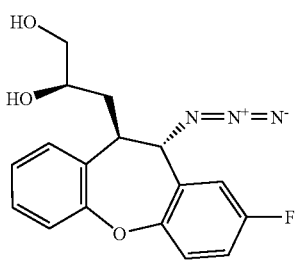

To a solution of intermediate 30 (0.369 g, 1 mmol) in THF (5 mL) 1M aq. HCl solution (1 mL) was added and stirred for 18 hours. THF was removed under reduced pressure and the diol was extracted using Et$_2$O (3×10 mL). The organic layer was treated with aq. NaHCO$_3$ (5 mL) followed by a brine wash (5 mL). After drying over anhydrous MgSO$_4$ the solvent was removed under vacuum to obtain intermediate 31 as a thick viscous liquid (95%, 0.313 g).

HRMS: Calculated 329.1176; found 329.1184.

Example A29

(2R)-1-[(10R,11S)-11-azido-2-fluoro-10,11-dihydrodibenzo[b,f]oxepin-10-yl]-3-(trityloxy)-2-propanol (Intermediate 32)

intermediate 32

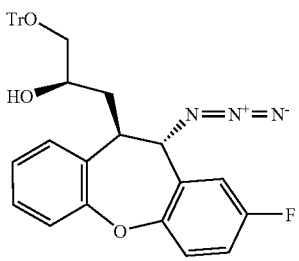

To a solution of intermediate 31 (0.329 g, 1 mmol) in CH$_2$Cl$_2$ (10 mL) Et$_3$N (0.28 mL, 2 mmol), DMAP (0.1 mmol, 12.2 mg) and TrCl (0.307 g, 1.1 mmol) were added and stirred for 24 hours. The solvent was removed under reduced pressure and the crude reaction mixture was subjected to flash column chromatography using EtOAc:heptane (1:9) as an eluant to obtain intermediate 32 as a white solid (mp: 58-59° C.; 80%, 0.456 g)

HRMS: Calculated 571.2271; found 571.2286. .

Example A30

(1R)-2-[(10R,11S)-11-azido-2-fluoro-10,11-dihydrodibenzo[b,f]oxepin-10-yl]-1-[(trityloxy)methyl] ethyl methanesulfonate (Intermediate 33)

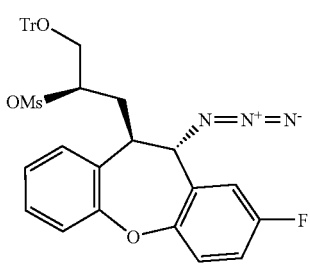

intermediate 33

To a solution of intermediate 32 (0.571 g, 1 mmol) in CH$_2$Cl$_2$ at −10° C., Et$_3$N (0.28 mL, 2 mmol), DMAP (12.2 mg, 0.1 mmol) and MsCl (0.126 g, 1.1 mmol) were added. The reaction mixture was warmed up to room temperature and stirred for 4 hours. Water (3 mL) was added and the organic layer was separated and dried over anhydrous MgSO$_4$ followed by the purification by flash chromatography using EtOAc:heptane (1:9) as an eluant to obtain intermediate 33 as a white solid (mp: 55-56° C.; 85%, 0.515 g).

HRMS: Calculated 649.2047; found 649.2064

Example A31

(1R)-2-[(10R,11S)-11-azido-2-fluoro-10,11-dihydrodibenzo[b,f]oxepin-10-yl]-1-(hydroxymethyl) ethyl methanesulfonate (Intermediate 34)

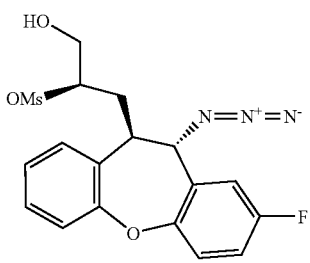

intermediate 34

To a solution of intermediate 33 (0.649 g, 1 mmol) in MeOH (5 mL), amberlyst-15 (0.1 g) was added and the reaction mixture was stirred at 40° C. for 3 hours, then filtered to remove the catalyst. The solvent was removed under reduced pressure and the product purified by flash chromatography using EtOAc:heptane (2:8) as an eluant to obtain intermediate 34 as a thick viscous liquid (90%, 0.366 g).

HRMS: Calculated 407.0951; found 407.0975.

Example A32

(10R,11S)-11-azido-2-fluoro-10-[(2S)-oxiranylmethyl]-10,11-dihydrodibenzo[b,f]-oxepine (Intermediate 35)

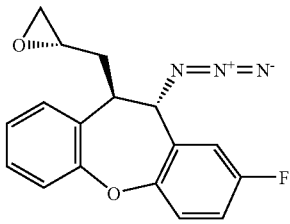

intermediate 35

A mixture of intermediate 34 (0.407 g, 1 mmol) and K$_2$CO$_3$ (0.276 g, 2 mmol) was stirred in i-PrOH (10 mL) for 8 hours, filtered to remove K$_2$CO$_3$ and the solvent was removed under reduced pressure. The product was purified by flash chromatography using EtOAc:heptane (2:8) as an eluant to obtain intermediate 35 as a colourless liquid (78%, 0.242 g).

HRMS: Calculated 311.1070; found 311.1089.

Example A33

[(2R,3aR,12bS)-11-fluoro-2,3,3a,12b-tetrahydro-1H-dibenzo[2,3:6,7]oxepino[4,5-b]pyrrol-2-yl]methanol (Intermediate 36)

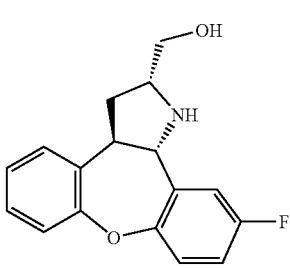

intermediate 36

To a solution of intermediate 35 (0.311 g, 1 mmol) in i-PrOH (10 mL), Et$_3$N (0.140 mL, 1 mmol) was added. The mixture was hydrogenated under atmospheric pressure using 10% Pd/C (50 mg) as a catalyst. After completion of the reaction (3 hours), it was passed through a small pad of celite and the catalyst was washed with CH$_2$Cl$_2$ (2×5 mL). The combined organic layers were evaporated under reduced pressure and purified by flash chromatography using EtOAC: heptane (1:1) as an eluant to obtain intermediate 36 as a white solid (mp: 108-109° C.; 83%, 0.236 g).

HRMS: Calculated 285.1165; found 285.1172.

Example A34

Methyl(2R,3aR,12bS)-11-fluoro-2-(hydroxymethyl)-2,3,3a,12b-tetrahydro-1H-dibenzo[2,3:6,7]oxepino[4,5-b]pyrrole-1-carboxylate (Intermediate 37)

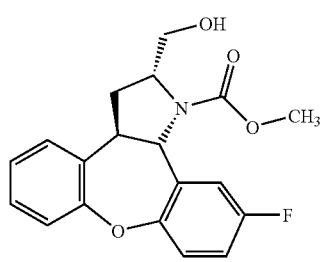

intermediate 37

To a solution of intermediate 36 (0.14 g, 0.5 mmol) in CH$_2$Cl$_2$ (4 mL) at 0° C. a saturated solution (aq) of NaHCO$_3$ (2 mL) was added. After the addition of methylchloroformate (1.5 eq), the reaction mixture was stirred vigorously at 0° C. for 20 minutes, warmed up to room temperature and allowed to stir further for 0.5 hour. The organic layer was separated, dried over MgSO$_4$ and purified by flash chromatography using EtOAc:heptane (4:6) as an eluant to obtain intermediate 37 as a thick viscous liquid (83%, 0.14 g).

HRMS: Calculated 343.1220; found 343.1218.

Example A35

Methyl(2R,3aR,12bS)-2-(aminomethyl)-11-fluoro-2,3,3a,12b-tetrahydro-1H-dibenzo[2,3:6,7]oxepino[4,5-b]pyrrole-1-carboxylate (Intermediate 38)

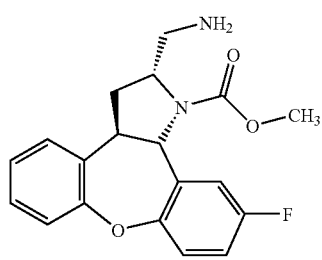

intermediate 38

To a solution of P(Ph)$_3$ (0.26 g, 1 mmol) in dry THF (4 mL) at −15° C. a solution of DIAD (0.22 g, 1.1 mmol) in THF (1 mL) was added and the resulting complex was stirred for 20 minutes. After the addition of intermediate 37 (0.17 g, 0.5 mmol) dissolved in THF (1 mL) and DPPA (0.14 g, 0.5 mmol) in THF (1 mL), the reaction was warmed to up room temperature and stirred for 18 hours. An excess of P(Ph)$_3$ (5 eq) and water (0.5 mL) was added to the reaction mixture and then heated at 40° C. for 3 hours to reduce the azide to amine functionality. Silica was added to the reaction mixture and the solvent was removed under reduced pressure followed by purification of the product by flash chromatography using CH$_2$Cl$_2$:MeOH (9:1) as an eluant to obtain intermediate 38 as a thick viscous liquid (80%, 0.14 g).

HRMS: Calculated 342.1380; found 342.1376.

Example A36

{(2R,3aR,12bS)-11-fluoro-1-[(2-nitrophenyl)sulfonyl]-2,3,3a,12b-tetrahydro-1H-dibenzo[2,3:6,7]oxepino[4,5-b]pyrrol-2-yl}methyl 2-nitrobenzenesulfonate (Intermediate 39)

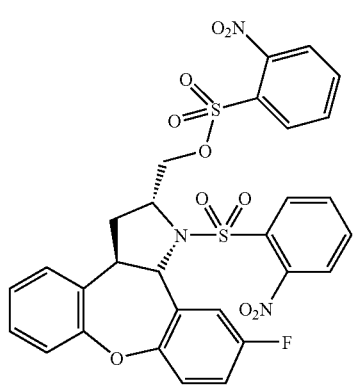

intermediate 39

To a solution of intermediate 36 (0.5 mmol, 0.14 g), Et$_3$N (5 eq) and DMAP (20 mol %) in CH$_2$Cl$_2$ at −20° C., o-nitrobenzenesulphonyl chloride (3 eq) was added. Reaction mixture was warmed up to room temperature and left for overnight stirring. Aqueous NaHCO$_3$ (2 mL) was added to the reaction mixture and the organic layer was separated and dried over MgSO$_4$. Following chromatography (SiO$_2$) using EtOAc:heptane (1:1) as an eluant yielded intermediate 39 as a yellow crystalline solid (mp: 88-90° C., 71%, 0.23 g).

Example A37 a) (10R,11R)-8-fluoro-11-((2R)-2-hydroxy-3-{[(4-methylphenyl)sulfonyl]oxy}propyl)-10,11-dihydro-5H-dibenzo[a,d]cyclohepten-10-yl acetate (Intermediate 23a)

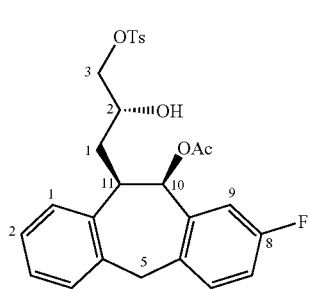

intermediate 23a

To a solution of acetate diol intermediate 23 (0.12 g, 0.355 mmol) in dry toluene (10 mL) was added n-Bu$_2$SnO (9 mg, 0.036 mmol), Et$_3$N (0.13 mL, 0.888 mmol) and TsCl (0.10 g, 0.533 mmol). Stir at room temperature for 24 hours, add NH$_4$Cl (sat. aq. solution, 10 mL), extract with CH$_2$Cl$_2$ (3×10 mL) and dry with MgSO$_4$. Column purification on silica gel using EtOAc/hexane (30:70) yielded intermediate 23a as a colorless oil (0.15 g, 84%).

Mass spectrum: CI m/z (assignment, relative intensity) 481 (MH$^+$—H$_2$O, 1%), 439 (MH$^+$-AcOH, 4%), 421 (MH$^+$-AcOH—H$_2$O, 1%), 267 (MH$^+$-AcOH-TsOH, 18%), 249 (MH$^+$-AcOH-TsOH—H$_2$O, 100%); EI: m/z (assignment, relative intensity) 480 (M$^{+\cdot}$—H$_2$O, 1%), 438 (M$^{+\cdot}$-AcOH, 36%), 266 (M$^{+\cdot}$-AcOH-TsOH, 15%), 248 (M$^{+\cdot}$-AcOH-TsOH—H$_2$O, 18%); High resolution EI Calculated C$_{25}$H$_{23}$FO$_4$S (M$^{+\cdot}$-AcOH): 438.1301, Found: 438.1300 (51%).

b) (10R,11R)-11-[(2R)-3-azido-2-hydroxypropyl]-8-fluoro-10,11-dihydro-5H-dibenzo$^2$[a,d]cyclohepten-10-yl acetate (Intermediate 40)

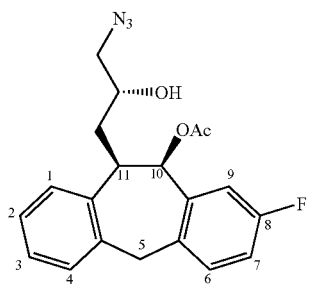

intermediate 40

To a solution of tosylate intermediate 23a (1.30 g, 2.61 mmol) in DMF (25 mL) was added NaN$_3$ (0.51 g, 7.83 mmol). The reaction mixture was heated at 100° C. for 1 night. After cooling, add NH$_4$Cl (sat. aq. sol.), extract 3 times with CH$_2$Cl$_2$ and dry with MgSO$_4$. After evaporation the residue was purified on silica gel using EtOAc/heptane (20/80) to give intermediate 40 as an oily product (0.79 g, 82%).

Example A38

(10R,11R)-11-[(2R)-3-azido-2-hydroxypropyl]-8-fluoro-10,11-dihydro-5H-dibenzo[a,d]cyclohepten-10-ol (Intermediate 41)

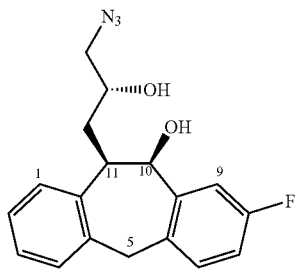

intermediate 41

A solution of acetate intermediate 40 (454.9 mg, 1.23 mmol) in MeOH (10 mL) was treated with K$_2$CO$_3$ (340.1 mg, 2.46 mmol) and the mixture was stirred at room temperature for 1 hour. Add NH$_4$Cl (sat. aq. sol.), extract 3 times with CH$_2$Cl$_2$ and dry with MgSO$_4$. The solution was filtered and evaporated and the residue was purified by column chromatography on silica gel using EtOAc/heptane (30/70) to give diol intermediate 41 (370.9 mg, 92%).

Example A39

S-((10S,11R)-11-{(2R)-3-azido-2-[(methylsulfonyl)oxy]propyl}-8-fluoro-10,11-dihydro-5H-dibenzo[a,d]cyclohepten-10-yl)ethanethioate (Intermediate 42)

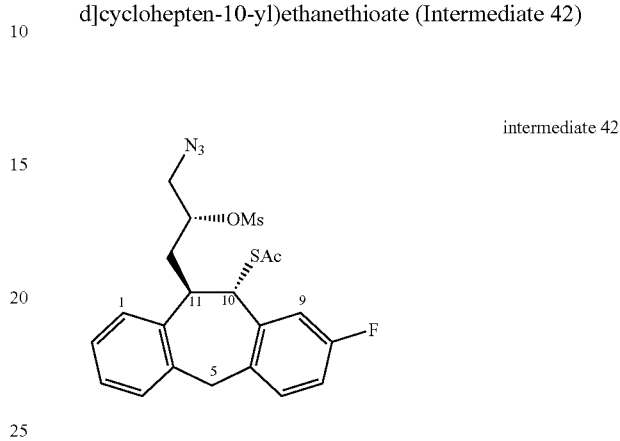

intermediate 42

To intermediate 41 (670 mg, 2.05 mmol) in CH$_2$Cl$_2$ (25 mL) was added Et$_3$N (2.30 mL, 16.4 mmol), DMAP (0.13 mg, 1.02 mmol) and (CH$_3$SO$_2$)$_2$O (1.07 g, 6.15 mmol) at 0° C. Stir at room temperature for 1 hour, cool to 0° C. again, add AcSH (0.44 ml, 6.15 mmol) and stir at room temperature for 4 hours. Work up by adding NH$_4$Cl (sat. aq. sol.). Extract 3 times with CH$_2$Cl$_2$. Column chromatography on silica gel using CH$_2$Cl$_2$ (100%) afforded intermediate 42 as an oil (0.68 g, 72%).

Example A40

(2S,3aR,12bS)-2-(azidomethyl)-11-fluoro-3,3a,8,12b-tetrahydro-2H-dibenzo[3,4:6,7]cyclohepta[1,2-b]thiophene (Intermediate 43)

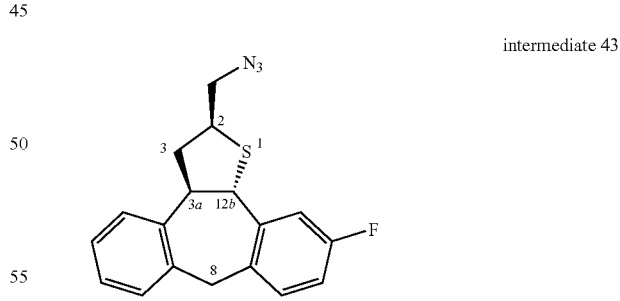

intermediate 43

To the above intermediate 42 (0.15 g, 0.33 mmol) in MeOH (5 mL) was added K$_2$CO$_3$ (92 mg, 0.67 mmol). After stirring at room temperature for 1 night, the mixture was worked up by adding NH$_4$Cl (sat. aq. sol.). Extract 3 times with CH$_2$Cl$_2$ and dry with MgSO$_4$. Column purification on silica gel using CH$_2$Cl$_2$/heptane (40/60) gave intermediate 43 as an oily product (76 mg, 70%).

Mass spectrum: CI m/z (assignment, relative intensity) 326 (MH$^+$, 25%), 298 (MH$^+$—N$_2$, 60%), 283 (MH$^+$—HN$_3$, 100%), 269 (MH$^+$—N$_2$—CH$_2$NH, 12%), 249 (MH$^+$—HN$_3$—H$_2$S, 25%), 235 (MH$^+$—N$_2$—CH$_2$NH—H$_2$S, 21%), 197 (61%).

Example A41

(2S,3aR,12bS)-2-(azidomethyl)-11-fluoro-3,3a,8,12b-tetrahydro-2H-dibenzo[3,4:6,7]cyclohepta[1,2-b]thiophene 1,1-dioxide (Intermediate 44)

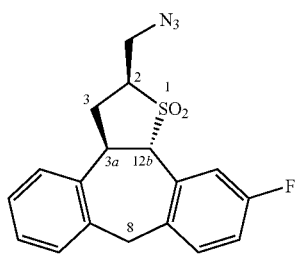

intermediate 44

To a solution of azide intermediate 43 (76.1 mg, 0.23 mmol) in CH$_2$Cl$_2$ (5 mL) was added m-CPBA (m-chloroperbenzoic acid) (173.2 mg, 0.70 mmol). The mixture was stirred at room temperature for 15 min. Add NaHCO$_3$ (sat. aq. solution), extract 3 times with CH$_2$Cl$_2$. Column purification on silica gel using EtOAc/heptane (50/50) gave sulfone intermediate 44 (73.2 mg, 88%) as an oil.

Mass spectrum: —CI m/z (assignment, relative intensity) 358 (MH$^+$, 21%), 340 (MH$^+$—H$_2$O, 9%), 330 (MH$^+$—N$_2$, 9%), 303 (8%), 265 (24%), 264 (MH$^+$—N$_2$—H$_2$SO$_2$, 25%), 237 (MH$^+$—N$_2$—H$_2$SO$_2$—HCN, 11%), 211 (15%), 197 (66%).

Example A42

(10R,11R)-11-[(2S)-3-azido-2-hydroxypropyl]-8-fluoro-10,11-dihydro-5H-dibenzo[a,d]cyclohepten-10-ol (Intermediate 45)

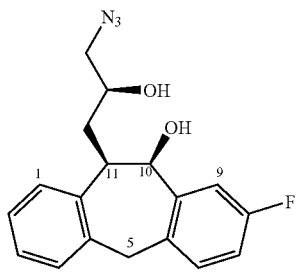

intermediate 45

To a solution of intermediate 40 (0.85 g, 2.32 mmol) in THF (10 mL) was added Ph$_3$P (1.22 g, 4.63 mmol) and DIAD (1.92 ml, 4.63 mmol). Then, a solution of p-nitrobenzoic acid (0.77 g, 4.63 mmol) in THF (10 mL) was added dropwise. The mixture was stirred at room temperature for 2 hours. Work up by adding NH$_4$Cl (sat. aq. sol.), extract 3 times with CH$_2$Cl$_2$. Column purification on silica gel using CH$_2$Cl$_2$/heptane (70/30) gave the p-nitrobenzoate (inverted secondary OH group) as an oil (1.19 g, 99%). To a solution of this compound (2.01 g, 4.05 mmol) in MeOH (50 mL) was added K$_2$CO$_3$ (1.12 g, 8.10 mmol). The reaction mixture was stirred at room temperature for 3 hours. Add NH$_4$Cl (sat. aq. sol.), extract 3 times with CH$_2$Cl$_2$. Column purification on silica gel using EtOAc/heptane (30/70) gave an oily intermediate 45 (0.71 g, 98%).

Example A43

S-((10S,11R)-11-{(2S)-3-azido-2-[(methylsulfonyl)oxy]propyl}-8-fluoro-10,11-dihydro-5H-dibenzo[a,d]cyclohepten-10-yl)ethanethioate (Intermediate 46)

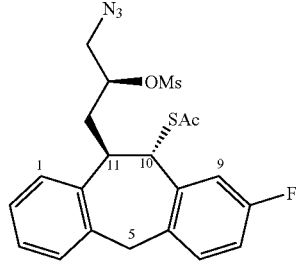

intermediate 46

To a solution of the diol intermediate 45 (1.20 g, 3.66 mmol) in CH$_2$Cl$_2$ (30 mL) was added Et$_3$N (4.10 mL, 29.3 mmol), DMAP (0.22 mg, 1.83 mmol) and (CH$_3$SO$_2$)$_2$O (1.92 g, 11.0 mmol) at 0° C. Stir at room temperature for 1 hour. Cool to 0° C. again and add AcSH (0.52 mL, 7.33 mmol) and stir at room temperature for 5 hours. Work up by adding NH$_4$Cl (sat. aq. sol.), extract 3 times with CH$_2$Cl$_2$ and dry with MgSO$_4$. Column purification on silica gel using EtOAc/heptane (30/70) afforded intermediate 46 as an oil (1.32 g, 78%).

Example A44

(2R,3aR,12bS)-2-(azidomethyl)-11-fluoro-3,3a,8,12b-tetrahydro-2H-dibenzo-[3,4:6,7]cyclohepta[1,2-b]thiophene (Intermediate 47

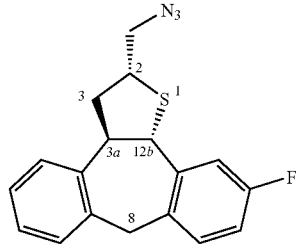

intermediate 47

To a solution of the above intermediate 46 (1.32 g, 2.86 mmol) in MeOH (30 mL) was added K$_2$CO$_3$ (0.79 g, 5.72 mmol). After stirring at room temperature for 2 hours, NH$_4$Cl (sat. aq. sol.) was added. Extract 3 times with CH$_2$Cl$_2$ and dry with MgSO$_4$. Column purification on silica gel using CH$_2$Cl$_2$/heptane (40/60) gave intermediate 47 as an oily product (0.82 g, 89%).

Mass spectrum: —CI m/z (assignment, relative intensity) 326 (MH$^+$, 25%), 298 (MH$^+$—N$_2$, 60%), 283 (MH$^+$—HN$_3$, 100%), 269 (MH+—N₂—CH₂NH, 12%), 269 (MH+—HN₃—H₂S, 25%), 235 (MH+—N₂—CH₂NH—H₂S, 21%), 197 (61%).

Example A45

(2R,3aR,12bS)-2-(azidomethyl)-11-fluoro-3,3a,8,12b-tetrahydro-2H-dibenzo[3,4:6,7]cyclohepta[1,2-b]thiophene 1,1-dioxide (Intermediate 48)

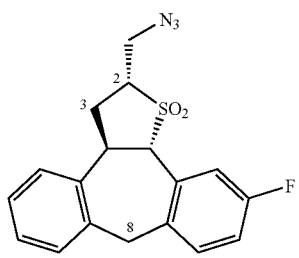

intermediate 48

To a solution of azide intermediate 47 (136.1 mg, 0.41 mmol) in CH₂Cl₂ (10 mL) was added m-chloroperbenzoic acid (310.0 mg, 1.26 mmol). The mixture was stirred at room temperature for 30 minutes. Add NaHCO₃ (sat. aq. solution), extract 3 times with CH₂Cl₂. Column purification on silica gel using EtOAc/heptane (50/50) gave sulfone intermediate 48 (146.5 mg, 98%) as an oil.

Mass spectrum: —CI m/z (assignment, relative intensity) 358 (MH+, 21%), 340 (MH+—H₂O, 9%), 330 (MH+—N₂, 9%), 303 (8%), 265 (24%), 264 (MH+—N₂—H₂SO₂, 25%), 237 (MH+—N₂—H₂SO₂—HCN, 11%), 211 (15%), 197 (66%).

Example A46

(2S,3aR,12bS)-2-(azidomethyl)-11-fluoro-3,3a,8,12b-tetrahydro-2H-dibenzo[3,4:6,7]cyclohepta[1,2-b]thiophene 1-oxides (Intermediates 49, 50)

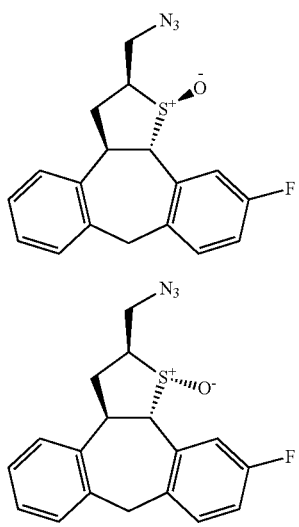

intermediate 49 intermediate 50

To a solution of azide intermediate 43 (0.34 g, 1.05 mmol) in hexafluoroisopropanol (5 mL) was added H₂O₂ (30%, 0.24 mL, 2.10 mmol). The mixture was stirred at room temperature for 30 minutes. Add Na₂CO₃ (sat. aq. solution), extract 3 times with CH₂Cl₂. Column purification on silica gel using Et₂O (100%) afforded intermediates 49 (110 mg) and 50 (130 mg) with a total yield of 78%.

Mass spectrum: —CI m/z (assignment, relative intensity) 342 (MH+, 100%), 314 (MH+—N₂, 49%), 299 (MH+—HN₃, 47%), 264 (17%), 197 (96%).

Example A47

(2R,3aR,12bS)-2-(azidomethyl)-11-fluoro-3,3a,8,12b-tetrahydro-2H-dibenzo[3,4:6,7]cyclohepta[1,2-b]thiophene 1-oxides (Intermediates 51, 52)

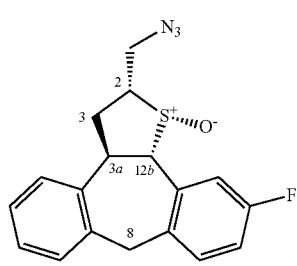

intermediate 51

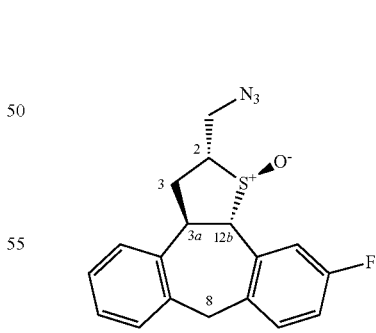

intermediate 52

To a solution of azide intermediate 47 (0.21 g, 0.64 mmol) in hexafluoroisopropanol (3 mL) was added H₂O₂ (30%, 0.15 mL, 1.27 mmol). The mixture was stirred at room temperature for 30 minutes. Add Na₂CO₃ (sat. aq. solution), extract 3 times with CH₂Cl₂. Column purification on silica gel using Et₂O (100%) gave intermediate 51 (120 mg) and 52 (86 mg) with a total yield of 95%.

Mass spectrum: —CI m/z (assignment, relative intensity) 342 (MH+, 100%), 314 (MH+—N2, 49%), 299 (MH+—HN3, 47%), 264 (17%), 197 (96%).

Example A48

(10S*,11R*)-11-allyl-8-fluoro-10,11-dihydro-5H-dibenzo[a,d]cyclohepten-10-yl acetate (Intermediate 56)

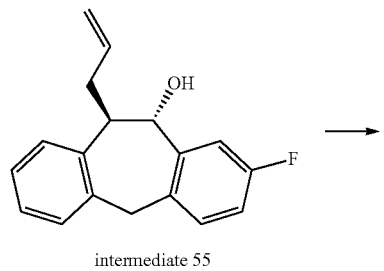

intermediate 55

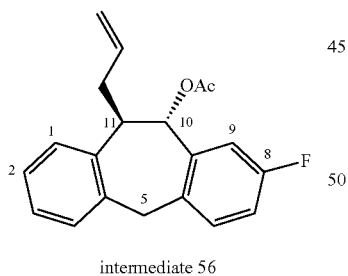

intermediate 56

Dissolve alcohol intermediate 55 (1.72 g, 6.42 mmol) in CH2Cl2 (30 mL). Add Et3N (1.79 mL, 12.8 mmol), DMAP (0.78 g, 6.42 mmol) and AcOH anhydride (1.21 mL, 12.8 mmol). Stir at room temperature for 1 hour and add sat. aq. NH4Cl (15 mL). Extract 3 times with CH2Cl2 (3×20 mL) and dry with MgSO4. Column purification on silica gel using CH2Cl2/hexane (60:40) yielded intermediate 56 as an oil (1.77 g, 89%).

Mass spectrum: —CI m/z (assignment, relative intensity) 311 (MH+, 5%), 251 (MH+—AcOH, 100%); EI: m/z (assignment, relative intensity) 250 (M+·-AcOH, 16%), 209 (M+·-AcOH—CH2CH2=CH2, 100%); High resolution EI Calculated C18H15F (M+·—AcOH): 250.1158, Found: 250.1162 (26%).

Example A49 a) (2R)-1-[(10R,11S)-11-azido-2-fluoro-10,11-dihydro-5H-dibenzo[a,d]cyclohepten-10-yl]-3-(trityloxy)-2-propanol (Intermediate 57)

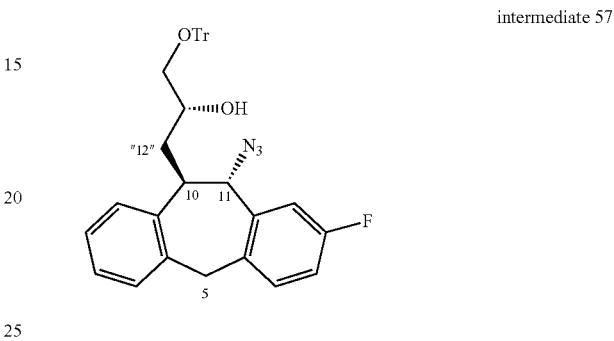

intermediate 57

A mixture of the diol intermediate 5 (6.022 g, 18.40 mmol), Et3N (5.586 g, 55.2 mmol), 4-dimethylaminopyridine (138 mg, 1.13 mmol), trityl bromide (9.444 g, 27.6 mmol) in CH2Cl2 (180 mL) was stirred at room temperature under nitrogen atmosphere for 2 hours, then quenched with saturated aqueous NH4Cl (50 mL). The organic phase was separated, aqueous layer extracted with CH2Cl2 (2×50 mL), combined organics washed with water (3×40 mL), brine (40 mL), dried (MgSO4) and evaporated in vacuo. Purification by flash chromatography (Kieselgel 60, 230-400 mesh, EtOAc-heptane, 5/95 to 10/90) gave intermediate 57 (8.595 g, 15.09 mmol, 82%) as a brown semisolid.

b) (1R)-2-[(10R,11S)-11-Azido-2-fluoro-10,11-dihydro-5H-dibenzo[[a,d]cyclohepten-10-yl]-1-[(trityloxy)methyl]ethylmethanesulfonate (Intermediate 58)

intermediate 58

A mixture of the alcohol intermediate 57 (8.500 g, 14.92 mmol), Et3N (4.529 g, 44.76 mmol) and DMAP (84 mg, 0.689 mmol) in CH2Cl2 (200 mL) was cooled down to −78° C. under nitrogen atmosphere. MsCl (2.264 g, 22.38 mmol) was added in one portion, resulting solution slowly warmed up to room temperature (ca. 40 min) and quenched with saturated aqueous NH4Cl (50 mL). The organic phase was separated, aqueous layer extracted with CH2Cl2 (3×45 mL), combined organics washed with water (3×45 mL) and brine c) (1R)-2-[(10R,11S)-11-azido-2-fluoro-10,11-dihydro-5H-dibenzo[a,d]cyclohepten-10-yl]-1-(hydroxymethyl)ethyl methanesulfonate (Intermediate 59)

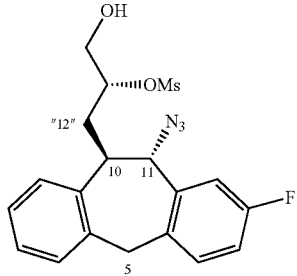

intermediate 59

Crude intermediate 58 (unknown amount, assumed 14.92 mmol), was dissolved in MeOH (200 mL), dry Amberlyst-15 (15 g) added and the mixture was stirred at 45° C. for 4 hours; progress of reaction followed by TLC (Kieselgel on glass; EtOAc-heptane 30/70). The resin was filtered off and washed with MeOH (2×40 mL), methanolic solution concentrated in vacuo to 100 mL, and intermediate 59 used immediately for the next step.

d) (10S,11R)-8-fluoro-11-[(2S)-oxiranylmethyl]-10,11-dihydro-5H-dibenzo[a,d]-cyclohepten-10-yl azide (Intermediate 60)

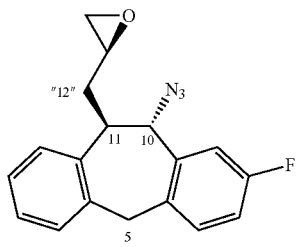

intermediate 60

Methanolic solution of intermediate 59, obtained as above, was treated with anhydrous $K_2CO_3$ (4.146 g, 30 mmol) and stirred at room temperature for 3 hours. After treatment with water (100 mL), MeOH was removed in vacuo, product extracted with $Et_2O$ (3×75 mL). The combined organics were washed with water (3×75 mL) and brine (40 mL), dried ($MgSO_4$) and evaporated in vacuo. Chromatographic purification (Kielselgel 60, 70-230 mesh, EtOAc-heptane 10/90) gave intermediate 60 (3.185 g, 10.29 mmol, 69% from intermediate 57) as a colorless oil.

HRMS: Calcd. for $C_{18}H_{16}FN_3O$: 309.1277; Found: 309.1279.

e) [(2R,3aR,12bS)-11-fluoro-1,2,3,3a,8,12b-hexahydrodibenzo[3,4:6,7]cyclohepta-[1,2-b]pyr-rol-2-yl]methanol (Intermediate 61)

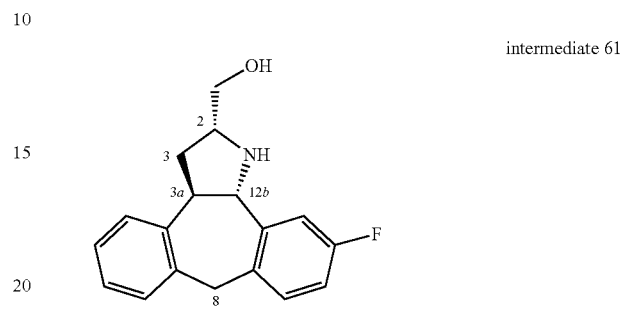

intermediate 61

Epoxide intermediate 60 (3.108 g, 10.04 mmol) was dissolved in MeOH (50 mL) $Et_3N$ (1.012 g, 10 mmol) and 10% Pd—C (150 mg) added, and resulting mixture hydrogenated under atmospheric pressure for 5 hours. Catalyst was removed by filtration through short pad of Kieselguhr, MeOH and $Et_3N$ removed in vacuo, and residue purified by column chromatography (Kieselgel 60, 70-230 mesh, EtOH—$CH_2Cl_2$ 5/95) to yield intermediate 61 (2.333 g, 8.23 mmol, 82%) as a yellowish oil, slowly solidifying on standing.

HRMS: Calcd. for $C_{18}H_{18}FNO$: 283.1372; Found: 283.1380.

f) Methyl(2R,3aR,12bS)-11-Fluoro-2-(hydroxymethyl)-3,3a,8,12b-tetrahydrodibenzo-[3,4:6,7]cyclohepta[1,2-b]pyrrole-1(2H)-carboxylate (Intermediate 62)

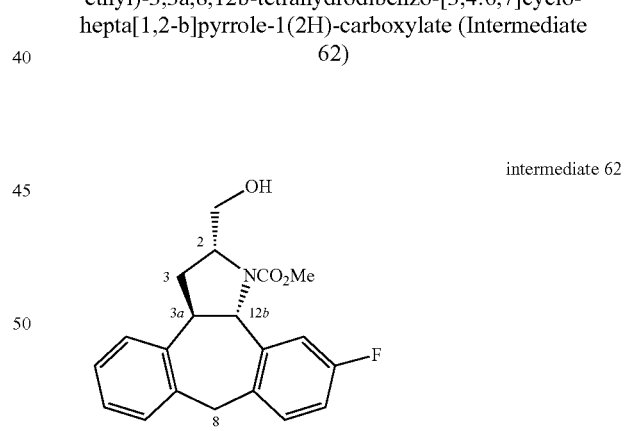

intermediate 62

Pyrrolidine intermediate 61 (567 mg, 2.00 mmol) was dissolved at 0° C. in a mixture of $CH_2Cl_2$ (20 mL) and saturated aqueous $NaHCO_3$ (20 mL), then methyl chloroformate (0.23 mL, 281 mg, 2.98 mmol) was added, ice bath removed, and resulting mixture stirred for 5 hours. The organic layer was separated, aqueous phase extracted with $CH_2Cl_2$ (40 mL) then the combined organics washed with water (2×40 mL), brine (20 mL), dried ($MgSO_4$) and evaporated. The residue was purified by column chromatography on silica ($CH_2Cl_2$-EtOH, 95/5) to give carbamate intermediate 62 (669 mg, 1.96 mmol, 98%) as tan oil, solidifying on standing.

g) (2R,3aR,12bS)-11-Fluoro-2-(hydroxymethyl)-3,3a,8,12b-tetrahydrodibenzo-[3,4:6,7]cyclo-hepta[1,2-b]pyrrole-1(2H)-carbaldehyde (Intermediate 62a)

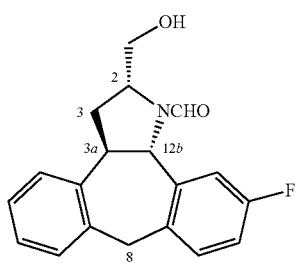
intermediate 62a

A mixture of intermediate 61 (283 mg, 1 mmol), ethyl formate (741 mg, 10 mmol) and acetonitrile (10 mL) was refluxed for 18 hours, then evaporated in vacuo. The residue was purified by chromatography (Kieselgel 60, 70-230 mesh, EtOH—CH$_2$Cl$_2$ 5/95) to yield 62a (283 mg, 0.91 mmol, 91%) as a tan solid.

Product is mixture of 2 rotamers (3:2 ratio).

CI-MS (CH$_4$) 312 (MH$^+$, 100%); 292 (MH$^+$—HF, 13%).

Example A50

(2R,3aR,12bS)-11-Fluoro-3,3a,8,12b-tetrahydrod-ibenzo[3,4:6,7]cyclohepta[1,2-b]pyrrole-1,2(2H)-dicarbaldehyde (Intermediate 63)

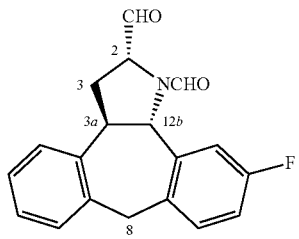
intermediate 63

Pyridinium chlorochromate (104 mg, 0.48 mmol) was added to the solution of alcohol intermediate 62a (100 mg, 0.32 mmol) in CH$_2$Cl$_2$ (10 mL), and the resulting slurry was stirred under nitrogen atmosphere for 3 hours. After addition of Et$_2$O (20 mL), the mixture was filtered through silica, the tar residue in flask washed with Et$_2$O (40 mL), filtered again, evaporated to dryness in vacuo. Crude aldehyde intermediate 63 (77 mg, 0.25 mmol, 78%) was obtained as reddish oil, containing trace of chromium. Product was used immediately without purification.

CI-MS (CH$_4$) 310 (100%, MH$^+$), 290 (11%, MH$^+$—HF); 282 (7%, MH$^+$—CO).

Example A51

(2aS,11bR,12aR)-4-Fluoro-1,2a,7,11b,12,12a-hexahydroazireno[1,2-a]dibenzo[3,4:6,7]cyclo-hepta[1,2-d]pyrrole (Intermediate 64)

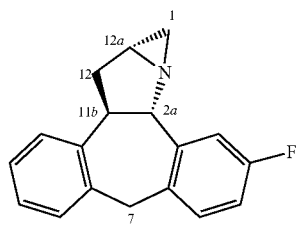
intermediate 64

Poly(triphenylphosphine) (0.33 g, ca. 1 mmol of Ph$_3$P) was swollen under argon atmosphere in dry CH$_2$Cl$_2$ (10 mL), then diisopropyl azodicarboxylate (222 mg, 1.1 mmol) in THF (3 mL) was added through septum at 0° C. The suspension was stirred for 30 minutes at 0° C., followed by addition of intermediate 61 (104 mg, 0.366 mmol) in THF (4 mL). The cooling bath was removed and reaction mixture was stirred at room temperature for 12 hours, then water (0.1 mL) was added, resin filtered off and washed with THF (15 mL), combined organics evaporated and purified by column chromatography (Kieselgel 60, 230-400 mesh, CH$_2$Cl$_2$-EtOH 100/0 to 96/4) to give intermediate 64 (63 mg, 0.238 mmol, 65%) as yellowish oil.

HRMS Calcd. for C$_{18}$H$_{16}$FN: 265.1267; Found: 265.1270.

Example A52 a) {(2R,3aR,12bS)-11-Fluoro-1-[(2-nitrophenyl)sulfonyl]-1,2,3,3a,8,12b-hexahydrodibenzo-[3,4:6,7]cyclohepta[1,2-b]pyrrol-2-yl}methyl 2-nitrobenzene-sulfonate (Intermediate 65)

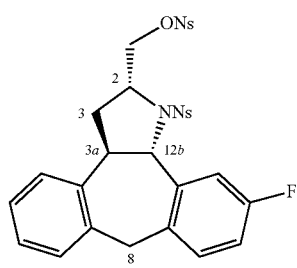
intermediate 65

A solution of pyrrolidine intermediate 61 (567 mg, 2.00 mmol), Et$_3$N (1.012 mmol, 10.00 mmol), dimethylaminipyridine (40 mg, 0.33 mmol) in CH$_2$Cl$_2$ (30 mL) was treated with 2-nitrobenzenesulfonyl chloride (1.330 g, 6.00 mmol), and resulting mixture was stirred at room temperature for 3 hours, then quenched with saturated aqueous NH$_4$Cl (30 mL). After extraction with CH$_2$Cl$_2$ (3×30 mL) the combined organics were washed with 1N HCl (15 mL), saturated aqueous K$_2$CO$_3$ (40 mL), water (3×40 mL), brine, dried (MgSO$_4$), evaporated and purified by column chromatography on silica (heptane-EtOAc, 95/5→85/15) to give intermediate 65 (1.203 g, 1.84 mmol, 92%) as yellow crystals, rapidly decomposing on standing.

¹, l NMR (300 MHz, CDCl₃) δ8.26-7.50 (m, 8H, Ar—H, 2-nosyl moieties); 7.20-7.03 (m, 6H, Ar—H, dibenzosuberone part); 6.81 (td, J=8.3, 2.7 Hz, 1H, Ar—H); 5.40 (d, J=11.0 Hz, 1H, CH-12b); 4.69 (d, J=16.7 Hz, 1H, CH₂-8); 4.60 (m, 2H, CH₂ONs); 4.40 (m, 1H, CH-2); 3.73 d, J=16.7 Hz, 1H, CH₂'-8); 3.55-3.40 (m, 1H, CH-3a); 2.80 (dd, J=13.0, 6.2 Hz, CH₂-3); 2.33-2.18 (m, 1H, CH₂'-3). b) 2-[4-({2R,3aR,12bS)-11-Fluoro-1-[(2-nitrophenyl)sulfonyl]-1,2,3,3a,8,12b-hexahydro-dibenzo[3,4:6,7]cyclohepta[1,2-b]pyrrol-2-yl}methyl)-1-piperazinyl]-ethanol (Intermediate 66a) and 2-[({(2R,3aR,12bS)-11-Fluoro-1-[(2-nitrophenyl)-sulfonyl]-1,2,3,3a,8,12b-hexahydrodibenzo-[3,4:6,7]cyclohepta[1,2-b]pyrrol-2-yl}methyl)(methyl)amino]ethanol (Intermediate 66b)

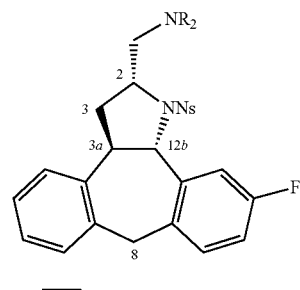

intermediate 66a

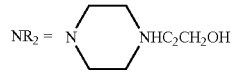

intermediate 66b

A mixture of bisnosyl intermediate 65 (0.35 g, 0.54 mmol) and appropriate amine (3 mmol) in dioxane (10 mL) was refluxed for 4 hours, cooled down to ambient temperature, diluted with water (100 mL), precipitated product filtered off, washed with water (100 mL), dissolved in EtOAc, solution washed with brine, dried (K₂CO₃), evaporated, and used for next step without purification.

Example A53 a) 2-[(4S)-2,2-Diethyl-1,3-dioxolan-4-yl]ethanol (Intermediate 67b)

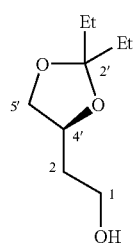

intermediate 67b

To a solution of (S)-1,2,4-butanetriol intermediate 67a (6.76 g, 63.68 mmol) in freshly distilled pentan-3-one (320 mL) was added p-toluenesulfonic acid (p-TSA) (6.06 g, 31.84 mmol). The reaction mixture was stirred at 53° C. for 16 hours, then Et₃N (10 mL) was added and the reaction mixture stirred at ambient temperature for 10 minutes. The reaction mixture was concentrated under reduced pressure. Gradient flash chromatography (CH₂Cl₂/MeOH, 100:0 to 97:3 to 95:5) afforded the protected alcohol intermediate 67b (9.84 g, 89%) as a colorless oil.

b) [(4S)-2,2-Diethyl-1,3-dioxolan-4-yl]acetaldehyde (Intermediate 67c)

intermediate 67c

To a solution of 2(S)-2-(2,2-diethyl-[1,3]dioxolan-4-yl)-ethanol intermediate 67b (4.00 g, 22.96 mmol) and 4 A molecular sieves (11.50 g) in CH₂Cl₂ (200 mL) stirred at 0° C. for 5 minutes was added pyridinium chlorochromate (PCC) (9.90 g, 45.92 mmol). The reaction mixture was allowed to warm to ambient temperature and stirred for 1 hour. The crude reaction mixture was filtered through a plug of silica, washed with Et₂O (50 mL) and concentrated under reduced pressure to afford the aldehyde intermediate 67c (3.56 g, 90%) as a colorless oil.

c) 11-{2-[(4S)-2,2-diethyl-1,3-dioxolan-4-yl]ethylidene}-8-fluoro-5,11-dihydro-10H-dibenzo-[a,d]cyclohepten-10-one (Intermediate 67d)

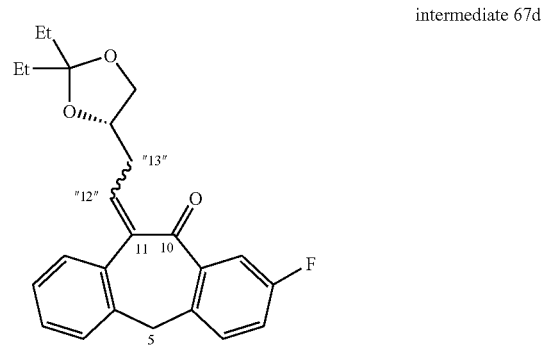 [SMILES: CCC1(CC)OC[C@H](CC=C2C(=O)c3cc(F)ccc3Cc3ccccc32)O1]

intermediate 67d

MgBr₂ (0.733 g, 3.98 mmol) was added to 8-fluoro-5,11-dihydro-10H-dibenzo[a,d]-cyclohepten-10-one (0.75 g, 3.32 mmol) in toluene (15 mL) and the reaction mixture stirred at room temperature for 30 minutes. Aldehyde intermediate 67c (2.05 g, 11.92 mmol) in THF (10 mL) was added and in one time t-BuOK (0.074 g, 0.66 mmol). The reaction mixture was stirred for 22 hours at ambient temperature, then saturated aqueous NH₄Cl (15 mL) was added. The product was extracted three times with Et₂O (3×30 mL), combined organics washed with water (2×35 mL), brine (25 mL) dried over MgSO₄. After evaporation of the toluene, the residue was purified on silica gel column using Et₂O/heptane (10/90) to obtain intermediate 67d (1.079 g, 86%) as a yellowish oil.

HRMS (EI) Calcd. for $C_{24}H_{25}FO_3$: 380.1800; Found: 380.1785.

d) (11R)-11-{2-[(4S)-2,2-diethyl-1,3-dioxolan-4-yl]ethyl}-8-fluoro-5,11-dihydro-10H-dibenzo-[a,d]cyclohepten-10-one (Intermediate 67e)

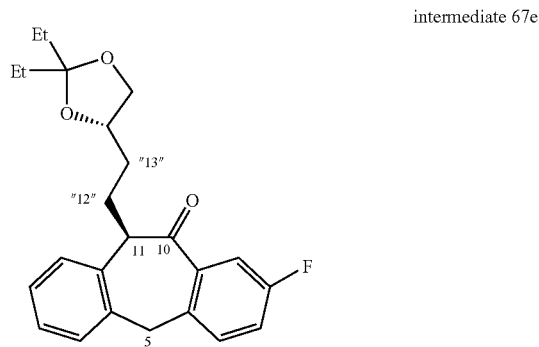 [SMILES: CCC1(CC)OC[C@H](CC[C@H]2C(=O)c3cc(F)ccc3Cc3ccccc32)O1]

intermediate 67e

10% Pd—C (200 mg) and $Et_3N$ (0.135 ml, 0.97 mmol) were added to intermediate 67d (0.246 g, 0.647 mmol) in i-PrOH (25 mL) and toluene (15 mL) and subjected to hydrogenation overnight at room temperature. The reaction mixture was dissolved in $CH_2Cl_2$, filtered through celite and solvent evaporated. The residue was purified on a silica gel column using $Et_2O$/heptane (30/70) to give intermediate 67e (151 mg, 61%) as a yellowish oil.

HRMS $C_{24}H_{27}FO_3$: 382.1944; Found: 382.1951.

e) (10R,11R)-11-{2-[(4S)-2,2-diethyl-1,3-dioxolan-4-yl]ethyl}-8-fluoro-10,11-dihydro-5H-di-benzo[a,d]cyclohepten-10-ol (Intermediate 67f)

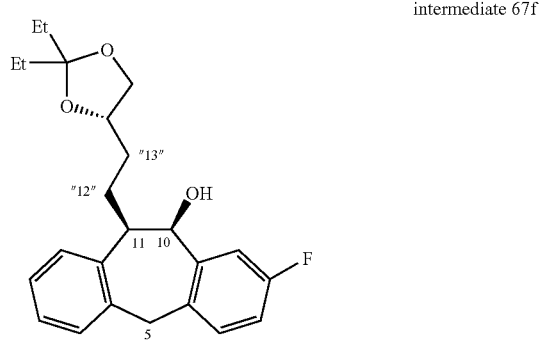 [SMILES: CCC1(CC)OC[C@H](CC[C@@H]2c3ccccc3Cc3ccc(F)cc3[C@@H]2O)O1]

intermediate 67f

Sodium borohydride (1.78 g, 46.84 mmol) was added to intermediate 35 (2.0 g, 5.88 mmol) dissolved in i-PrOH (80 mL)/pH 7 phosphate buffer (30 ml) at 0° C. After 1 hour of reaction at room temperature, $NH_4Cl$ (sat. aq. solution) was added and the mixture was extracted three times with $CH_2Cl_2$. The organic phase was dried over $MgSO_4$ and the solvent evaporated. The product was purified on silica gel using $Et_2O$/heptane (30/70) which gave intermediate 67f (1.96 g, 97%) as colorless oil.

HRMS Calcd. for $C_{11}H_{23}FO_3$: 342.1631; Found: 342.1627.

f) (4S)-4-{2-[(10R,11S)-11-azido-2-fluoro-10,11-dihydro-5H-dibenzo[a,d]cyclohepten-10-yl]-ethyl}-2,2-diethyl-1,3-dioxolane (Intermediate 67g)

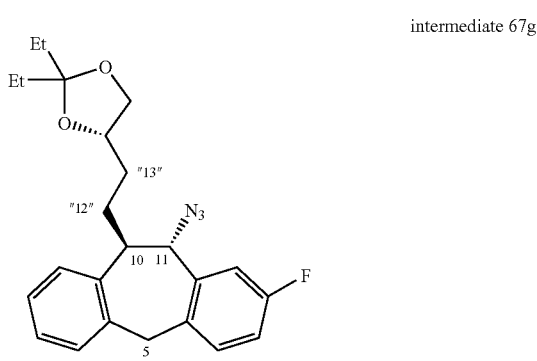 [SMILES: CCC1(CC)OC[C@H](CC[C@@H]2c3ccccc3Cc3ccc(F)cc3[C@H]2N=[N+]=[N-])O1]

intermediate 67g

Intermediate 67g was obtained in the same way as described for intermediate 30.

g) (2S)-4-[(10R,11S)-11-azido-2-fluoro-10,11-dihydro-5H-dibenzo[a,d]cyclohepten-10-yl]-1,2-butanediol (Intermediate 67h)

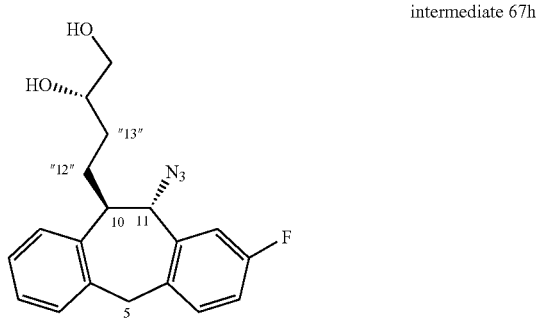 [SMILES: [N-]=[N+]=N[C@@H]1c2cc(F)ccc2Cc2ccccc2[C@H]1CC[C@H](O)CO]

intermediate 67h

Intermediate 67h was obtained in the same way as described for intermediate 31.

h) (2S)-4-[(10R,11S)-11-azido-2-fluoro-10,11-dihydro-5H-dibenzo[a,d]-cyclohepten-10-yl]-2-{[(4-methylphenyl)sulfonyl]oxy}butyl 4-methylbenzenesulfonate (Intermediate 67i)

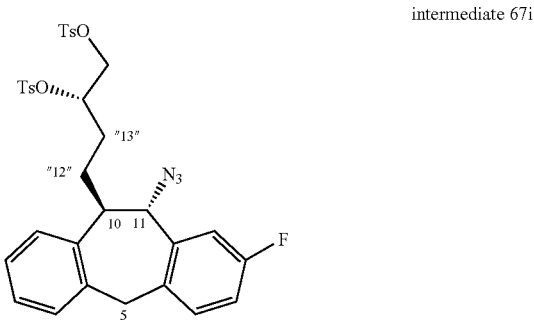

intermediate 67i

A mixture of (2S)-4-[(10R,11S)-11-azido-2-fluoro-10,11-dihydro-5H-dibenzo[a,d]-cyclohepten-10-yl]-1,2-butanediol intermediate 67h (225 mg, 0.66 mmol), Et₃N (506 mg, 5.0 mmol), dimethylaminopyridine (12 mg, 0.1 mmol) and TsCl (503 mg, 2.64 mmol) in CH₂Cl₂ (25 mL) was stirred at room temperature under nitrogen atmosphere for 15 hours. After quenching with saturated aqueous ammonium chloride (15 mL), the organic phase was separated, and the aqueous layer extracted with CH₂Cl₂ (3×20 mL). The combined organics were washed with water (3×30 mL), brine (25 mL), dried over magnesium sulfate and evaporated in vacuo. The residue was purified by column chromatography (Kieselgel 60, 70-230 mesh, heptane-ethyl acetate 90/10) to afford intermediate 67i (352 mg, 0.54 mmol, 82%) as colorless semisolid.

i) [(2R,4aR,13bS)-2-Fluoro-2,3,4,4a,9,13b-hexahydro-1H-dibenzo[3,4:6,7]-cyclohepta[1,2-b]pyridin-2-yl]methyl 4-methylbenzenesulfonate (Intermediate 67k)

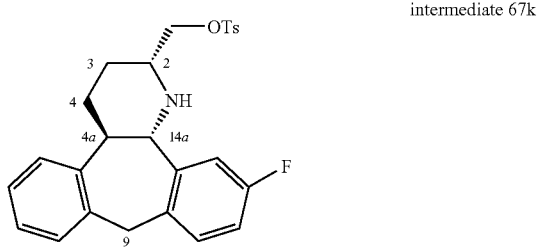 [SMILES: Cc1ccc(S(=O)(=O)OC[C@H]2CC[C@@H]3c4ccccc4Cc4ccc(F)cc4[C@H]3N2)cc1]

intermediate 67k

Bistosylate intermediate 67i (340 mg, 0.52 mmol) was dissolved in MeOH (15 mL) Et₃N (1.012 g, 10 mmol) and 10% Pd—C (150 mg) added, and resulting mixture hydrogenated under atmospheric pressure for 5 hours. Catalyst was removed by filtration through short pad of Kieselguhr, anhydrous K₂CO₃ (138 mg, 1 mmol) added and resulting slurry stirred at room temperature for 5 hours. After filtration of solids, MeOH and Et₃N were removed in vacuo, and residue purified by flash chromatography (Kieselgel 60, 230-400 mesh, EtOH—CH₂Cl₂ 5/95 to 12/88) to yield intermediate 67k (153 mg, 0.338 mmol, 65%) as yellowish oil.

CI-MS (CH₄) 452 (MH⁺, 1%); 280 (MH⁺-TsOH, 100%).

Example A54 a) (10S,11R)-11-{2-[(4S)-2,2-diethyl-1,3-dioxolan-4-yl]ethyl}-8-fluoro-10,11-dihydro-5H-dibenzo[a,d]cyclohepten-10-yl 4-nitrobenzoate (Intermediate 610)

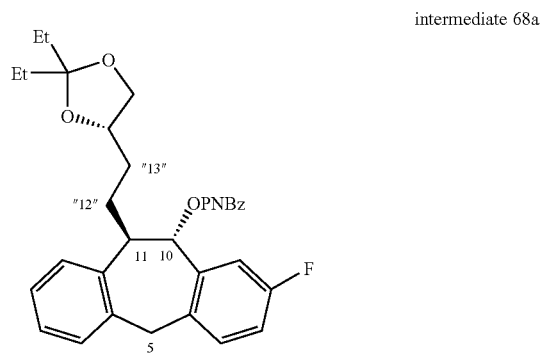

intermediate 68a

A solution of triphenylphosphine (910 mg, 3.5 mmol) in dry THF (25 mL) was placed in a two-necked 100 mL flask, equipped with septum, argon inlet and magnetic stirrer. After cooling down to −15° C. neat diisopropyl azodicarboxylate (708 mg, 3.5 mmol) was added through a septum with intensive stirring. Resulting yellow suspension was stirred at above temperature for 30 minutes, then a solution of 4-nitrobenzoic acid (585 mg, 3.50 mmol) and alcohol intermediate 67f (673 mg, 1.75 mmol) in THF (25 mL) was added within 10 minutes. The resulting yellow suspension was allowed to warm up to room temperature and stirred then for 12 hours. Water (0.3 mL) was added, followed by silica gel (Kieselgel 60, 70-230 mesh, 4 g), THF removed in vacuo, and silica powder submitted to the flash chromatography (Kieselgel 60, 230-400 mesh, EtOAc-heptane, 5/95 to 15/85) to give nitrobenzoate intermediate 610 (795 mg, 1.49 mmol, 85%) as an orange semisolid.

b) (10S,11R)-11-[(3S)-3,4-dihydroxybutyl]-8-fluoro-10,11-dihydro-5H-dibenzo-[a,d]cyclo-hepten-10-yl 4-nitrobenzoate (Intermediate 68b)

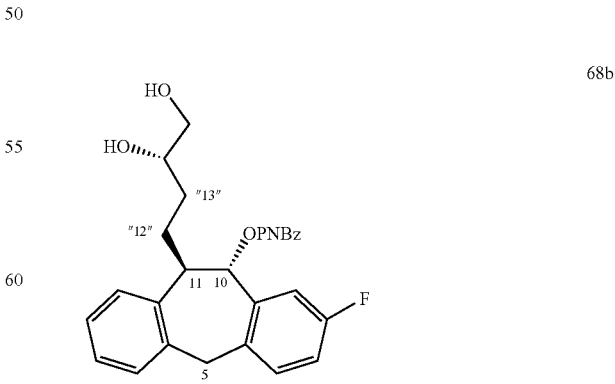

68b

Hydrolysis of dioxolane intermediate 610 (795 mg, 1.49 mmol) was carried out in the same was as described in Example A28 to give diol intermediate 68b (695 mg, 1.49 mmol, 100%) as orange semisolid. Product was used without purification.

c) (10S,11R)-8-fluoro-11-((3S)-3-hydroxy-4-{[(4-methylphenyl)sulfonyl]oxy}-butyl)-10,11-dihydro-5H-dibenzo[a,d]cyclohepten-10-yl 4-nitrobenzoate (Intermediate 68c)

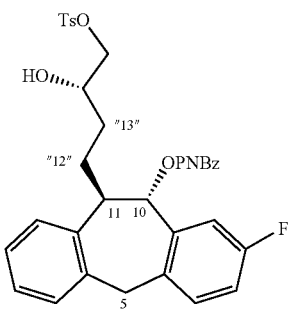

intermediate 68c

A mixture of the diol intermediate 68b (695 mg, 1.49 mmol), Et$_3$N (607 mg, 6 mmol), dibutyl(oxo)stannane (141 mg, 0.566 mmol), and TsCl (431 mg, 2.26 mmol) in CH$_2$Cl$_2$ (20 mL) was stirred at room temperature under N$_2$ for 12 hours. After quenching with saturated aqueous NH$_4$Cl (15 mL) the organic phase was separated and the aqueous solution extracted with CH$_2$Cl$_2$ (3×30 mL). The combined organics were washed with water (3×20 mL), filtered through 5 cm layer of MgSO$_4$, and evaporated in vacuo to furnish crude intermediate 68c (601 mg, 0.97 mmol, 65%) as a yellowish semisolid mass, which was converted without further purification.

d) [(2R,4aR,13bS)-12-fluoro-2,3,4,4a,9,13b-hexahydrodibenzo[3,4:6,7]cyclohepta-[1,2-b]pyran-2-yl]methanol (Intermediate 68d)

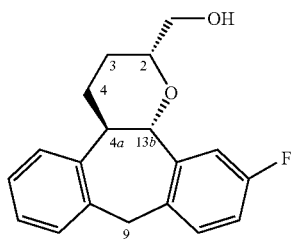

intermediate 68d

A mixture of tosylate intermediate 68c (601 mg, 0.97 mmol), sodium methoxide (162 mg, 3.0 mmol) and MeOH (10 mL) was stirred at room temperature for 3 hours. After treatment with water (100 mL) product was extracted with diethyl ether (3×30 mL). The combined organics were washed with water (3×40 mL) and brine (40 mL), dried (MgSO$_4$) and evaporated in vacuo. Chromatographic purification (Kielselgel 60, 70-230 mesh, EtOAc-heptane 10/90 to 25/75) gave intermediate 68d (211 mg, 0.71 mmol, 73%) as a colorless oil.
HRMS Calcd. for C$_{19}$H$_{19}$FO$_2$: 298.1369; Found 298.1350.

d) [(2R,4aR,13bS)-12-fluoro-2,3,4,4a,9,13b-hexahydrodibenzo[3,4:6,7]cyclohepta-[1,2-b]pyran-2-yl]methyl 4-methylbenzenesulfonate (Intermediate 68e)

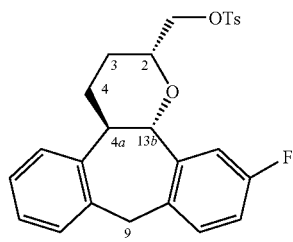

intermediate 68e

A mixture of the alcohol intermediate 68d (211 mg, 0.708 mmol), Et$_3$N (209 µL, 287 mg, 2.83 mmol), DMAP (86.5 mg, 0.708 mmol), and TsCl (270 mg, 1.42 mmol) in CH$_2$Cl$_2$ (10 mL) was stirred at room temperature under N$_2$ for 16 hours. After quenching with saturated aqueous NH$_4$Cl (10 mL) the organic phase was separated and the aqueous solution extracted with CH$_2$Cl$_2$ (3×15 mL). The combined organics were washed with water (3×15 mL), dried (MgSO$_4$), and evaporated in vacuo to give crude intermediate 68e (282 mg, 0.62 mmol, 88%) as a yellowish oil, which was used without further purification.

Example A55 a) (10S,11R)-11-{[(4R)-2,2-dimethyl-1,3-dioxolan-4-yl]methyl}-8-fluoro-10,11-dihydro-5H-dibenzo[a,d]cyclohepten-10-yl 4-nitrobenzoate (Intermediate 69a)

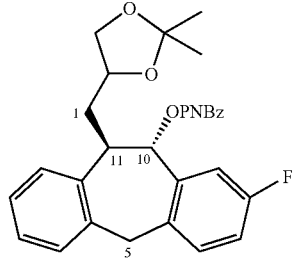

intermediate 69a

A solution of triphenylphosphine (1049 mg, 4.0 mmol) in dry THF (20 mL) was placed in a two-necked 100 mL flask, equipped with septum, argon inlet and magnetic stirrer. After cooling down to −15° C. neat diisopropyl azodicarboxylate (809 mg, 4.0 mmol) was added through a septum with intensive stirring. Resulting yellow suspension was stirred at above temperature for 30 minutes, then a solution of 4-nitrobenzoic acid (4.0 mmol) and 11-(2,2-dimethyl-[1,3]dioxolan-4-ylmethyl)-8-fluoro-10,11-dihydro-5H-dibenzo[a,d]cyclohepten-10-ol (Intermediate 3) (685. mg, 2.0 mmol) in THF (25 mL) was added within 10 minutes. The resulting yellow suspension was allowed to warm up to room temperature and stirred then for 12 hours. Water (0.3 mL) was added, followed by silica gel (Kieselgel 60, 70-230 mesh, 4 g), THF removed in vacuo, and silica powder submitted to the flash chromatography (Kieselgel 60, 230-400 mesh, EtOAc-heptane, 5/95 to 10/90) to give nitrobenzoate intermediate 69a (875 mg, 1.78 mmol, 89%) as an orange semisolid.

b) (10S,11R)-11-[(2R)-2,3-dihydroxypropyl]-8-fluoro-10,11-dihydro-5H-dibenzo[a,d]cyclo-hepten-10-yl 4-nitrobenzoate (Intermediate 69b)

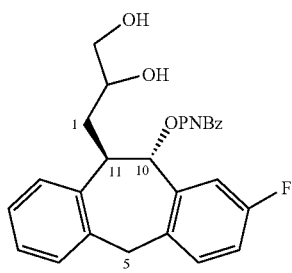

intermediate 69b

Intermediate 69b has been obtained from acetal intermediate 69a (860 mg, 1.75 mmol) in the same way as described for intermediate 5. Column chromatography (Kieselgel 60, 70-230 mesh, EtOAc-heptane, 35/65 to 50/50) afforded diol intermediate 69b (774 mg, 1.715 mmol, 98%) as a yellow semi-solid.

c) (10S,11R)-8-fluoro-11-(2-oxoethyl)-10,11-dihydro-5H-dibenzo[a,d]cyclohepten-10-yl 4-nitrobenzoate (Intermediate 69c)

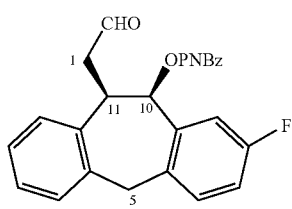

intermediate 69c

Diol intermediate 69b (774 mg, 1.715 mmol) was dissolved at 0° C. in a mixture of THF (25 mL) and pH 7 phosphate buffer (5 mL), then sodium periodate (642 mg, 3 mmol) was added in one portion at 0° C., cooling bath removed, and resulting mixture was stirred at room temperature for 4 hours. Water (50 mL) was added, product extracted with diethyl ether (3×30 mL). The combined organics were washed with saturated aqueous sodium metabisulfite (50 mL), water (2×50 mL), brine (30 mL), dried over magnesium sulfate and evaporated in vacuo to give aldehyde intermediate 69c (680 mg, 1.66 mmol, 97%) as a yellow foam. Product was used immediately without purification.

d) (10S,11S)-8-fluoro-11-(1-formylvinyl)-10,11-dihydro-5H-dibenzo[a,d]cyclohepten-10-yl 4-nitrobenzoate (Intermediate 69d)

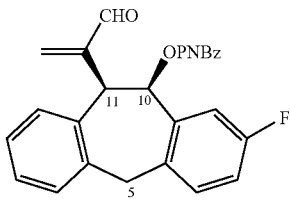

intermediate 69d

A mixture of aldehyde intermediate 69c (680 mg, 1.66 mmol), AcOH (240 mg, 4.0 mmol), bis(dimethylamino)methane (719 mg, 7.0 mmol) and THF (30 mL) was stirred at room temperature for 3 hours. Water (50 mL) was added, product extracted with diethyl ether (3×30 mL). The combined organics ware washed with saturated aqueous sodium bicarbonate (25 mL), water (2×50 mL), brine (30 mL), dried over magnesium sulfate and evaporated in vacuo to give unstaturated aldehyde intermediate 69d (680 mg, 1.58 mmol, 95%) as a yellow oil.

e) (10S,11S)-8-fluoro-11-[-1-(hydroxymethyl)vinyl]-10,11-dihydro-5H-dibenzo[a,d]cyclo-hepten-10-yl 4-nitrobenzoate (Intermediate 69e)

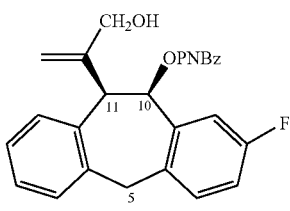

intermediate 69e

Sodium borohydride (190 mg, 5.00 mmol) was added at room temperature within 10 minutes to the solution of aldehyde intermediate 69d (680 mg, 1.58 mmol) in MeOH (30 mL). The reaction mixture was stirred at room temperature for 4 hours, quenched with saturated aqueous ammonium chloride (20 mL) and extracted with Et₂O (3×30 mL). The combined organics ware washed with water (2×50 mL), brine (30 mL), dried over magnesium sulfate and evaporated in vacuo to give alcohol intermediate 69e (582 mg, 1.34 mmol, 85%) as an orange oil.

f) (10S,11S)-8-fluoro-11-[1-(hydroxymethyl)vinyl]-10,11-dihydro-5H-dibenzo[a,d]cyclo-hepten-10-ol (Intermediate 69f)

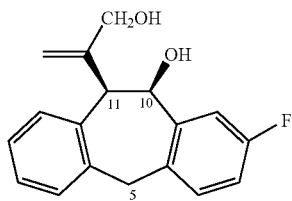

intermediate 69f

A mixture of nitrobenzoate intermediate 69e (582 mg, 1.34 mmol), sodium methoxide (162 mg, 3.0 mmol) and MeOH was stirred at room temperature for 4 hours. Water (70 mL) was added, product extracted with EtOAc (3×30 mL). The combined organics were washed with water (2×50 mL), brine (30 mL), dried over magnesium sulfate and evaporated in vacuo. The residue was purified by flash chromatography (Kieselgel 60, 230-400 mesh, EtOAc-heptane, 35/65 to 60/40) to give diol intermediate 69f (286 mg, 1.005 mmol, 75%) as colorless oil.

g) (3aS,12bS)-11-fluoro-3-methylene-3,3a,8,12b-tetrahydro-2H-dibenzo[3,4:6,7]cyclohepta-[1,2-b]furan (Intermediate 69g)

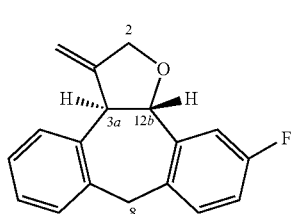

intermediate 69g

Tributylphosphine (405 mg, 2.0 mmol) was dissolved in toluene (25 mL) under argon atmosphere. Diisopropyl azodicarboxylate (405 mg, 2.0 mmol) in toluene (3 mL) was added dropwise, followed by solution of diol intermediate 69f (270 mg, 0.95 mmol). The resulting mixture was stirred at room temperature for 3 hours, then reaction was quenched water (1 mL). Silica gel (Kieselgel 60, 70-230 mesh, 1.3 g) was added, toluene removed in vacuo, and silica powder submitted to the flash chromatography (Kieselgel 60, 230-400 mesh, EtOAc-heptane, 5/95 to 12/88) to give THF derivative intermediate 69g (205 mg, 0.77 mmol, 81%) as colorless foam.

h) [(3aR,12bS)-11-fluoro-3,3a,8,12b-tetrahydro-2H-dibenzo[3,4:6,7]cyclohepta-[1,2-b]furan-3-yl]methanol (Intermediate 69h)

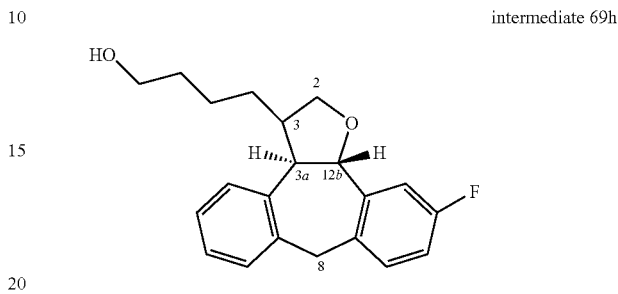

intermediate 69h

Boron trifluoride etherate (0.43 mL, 3.54 mmol) in THF (1 mL) was added at room temperature under argon atmosphere to the solution of THF intermediate 69g (188 mg, 0.66 mmol), sodium borohydride (496 mg, 2.64 mmol) in dry THF (2 mL). The resulting solution was stirred under argon for 24 hours, excess of borohydrided decomposed carefully with water (3.8 mL), MeOH (1.5 mL) added, followed by 3M NaOH (3.8 mL) and 30% hydrogen peroxide (0.55 mL). Reaction mixture was allowed to stir for 4 hours at room temperature, then the product was extracted with Et₂O (3×30 mL). The combined organics ware washed with water (2×50 mL), brine (30 mL), dried over magnesium sulfate and evaporated in vacuo. The residue was purified by flash chromatography (Kieselgel 60, 230-400 mesh, EtOAc-heptane, 5/95 to 20/80) to give THF derivative intermediate 69h (139 mg, 0.49 mmol, 74%) as colorless oil.

i) (3aR,12bS)-3-(azidomethyl)-11-fluoro-3,3a,8,12b-tetrahydro-2H-dibenzo[3,4:6,7]cyclo-hepta[1,2-b]furan (Intermediate 69i)

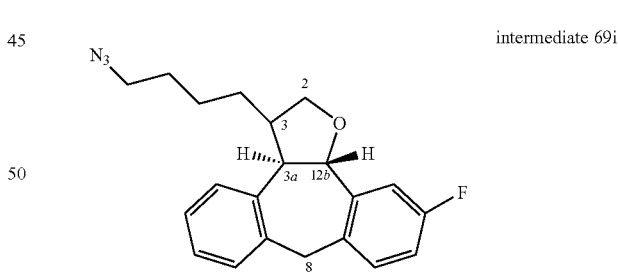

intermediate 69i

Poly(triphenylphosphine) (0.33 g, ca. 1 mmol of Ph₃P) was swollen at room temperature under argon atmosphere in dry THF (10 mL), then diisopropyl azodicarboxylate (222 mg, 1.1 mmol) in THF (3 mL) was added through septum at −15° C. The suspension was stirred for 30 minutes at −15° C., then alcohol intermediate 69h (139 mg, 0.49 mmol) in dry THF (2.5 mL) was added in one portion, followed by dropwise addition of diphenylphosphoryl azide (160 mg, 0.58 mmol) in THF (3 mL). Resulting suspension was stirred under argon for 12 hours. After quenching with water (0.3 mL), resin was filtered off and solvent removed in vacuo. The residue was purified by flash chromatography (Kieselgel 60, 230-400 mesh, EtOAc-heptane, 15/85) to give azide intermediate 69i (136 mg, 0.44 mmol, 90%) as colorless foam.

Example A56 a) (2R)-3-[(10R,11R)-2-fluoro-11-hydroxy-10,11-dihydro-5H-dibenzo[a,d]-cyclohepten-10-yl]-1,2-propanediol (Intermediate 70a)

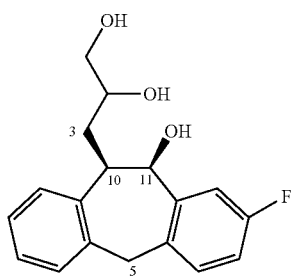

intermediate 70a

Triol intermediate 70a was obtained from intermediate 3 (514 mg, 1.50 mmol) in the same way as described in Example A5. Crude intermediate 70a (449 mg, 1.485 mmol, 99%) was obtained as colorless oil and used without purification.

b) (3aR,12bR)-11-fluoro-3,3a,8,12b-tetrahydro-2H-dibenzo[3,4:6,7]cyclohepta[1,2-b]furan-2-ol (Intermediate 70b)

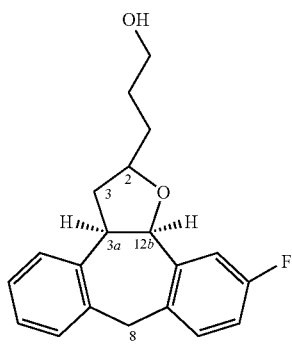

intermediate 70b

Intermediate 70b was obtained from triol intermediate 70a (449 mg, 1.485 mmol) in the same way as described for compound 44. Flash chromatography (Kieselgel 60, 230-400 mesh, EtOAc-heptane, 10/90 to 33/67) afforded intermediate 70c (357 mg, 1.32 mmol, 89%) as tan solid.

d) (3aR,12bR)-3-[(dimethylamino)methyl]-11-fluoro-3,3a,8,12b-tetrahydro-2H-dibenzo-[3,4:6,7]cyclohepta[1,2-b]furan-2-ol (Intermediate 70c)

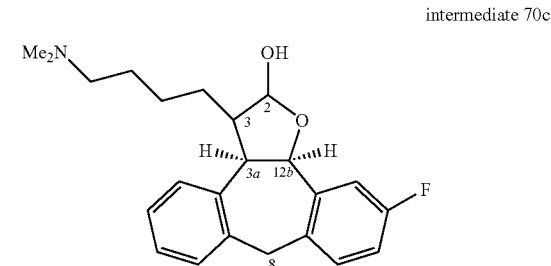

intermediate 70c

Reaction of intermediate 70c (335 mg, 1.24 mmol) was carried out in the same way as described for compound 45. Complex, unseparable mixture of products has been formed and used for the next step without purification.

d) (10R,11R)-11-[2-(dimethylamino)-1-(hydroxymethyl)ethyl]-8-fluoro-10,11-dihydro-5H-dibenzo[a,d]cyclohepten-10-ol (Intermediate 70d)

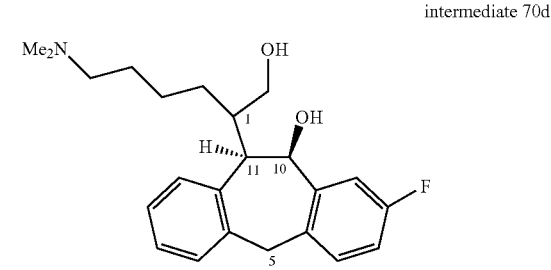 [SMILES: CN(C)CCCCC(CO)[C@@H]1c2ccccc2Cc2ccc(F)cc2[C@@H]1O]

intermediate 70d

Reaction of the mixture containing intermediate 70c was carried out in the same way as described for compound 46. Purification by RP-HPLC (Waters Xterra® $C_{18}$, 19×50 mm, MeOH-water 50/50, then pure MeOH, 4 mL/min) afforded intermediate 70d (135 mg, 0.41 mmol, 33% from intermediate 70b) as yellow oil.

Example A57 a) [(10R,11S)-11-azido-2-fluoro-10,11-dihydro-5H-dibenzo[a,d]cyclohepten-10-yl]-acetaldehyde (Intermediate 71a)

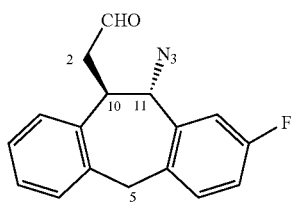

intermediate 71a

Reaction of diol intermediate 5 (0.99 g, 3.02 mmol) was carried out in the same way as described for compound 44. Purification by column chromatography (Kieselgel 60, 230-400 mesh, diethyl ether-heptane, 50/50) gave aldehyde intermediate 71a (778 mg, 2.63 mmol, 87%) as colorless oil.

b) 2-[(10S,11S)-11-azido-2-fluoro-10,11-dihydro-5H-dibenzo[a,d]cyclohepten-10-yl]acryl-aldehyde (Intermediate 71b)

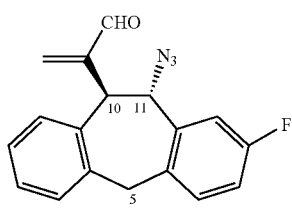

intermediate 71b

Reaction of intermediate 71a (618 mg, 2.09 mmol) was carried out in the same way as described for compound 45. Crude aldehyde intermediate 71b (605 mg, 1.97 mmol, 94%) was obtained as colorless oil and was used without further purification.

c) (3aS,12bS)-11-fluoro-3-methylene-1,2,3,3a,8,12b-hexahydrodibenzo[3,4:6,7]-cyclohepta-[1,2-b]pyrrole (Intermediate 71c)

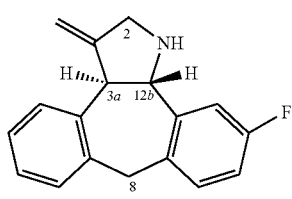

intermediate 71c

Poly(triphenylphosphine) (1.40 g, ca 4.2 mmol of Ph$_3$P) was swollen at room temperature under argon atmosphere in THF (30 mL), then aldehyde intermediate 71b (405 mg, 1.32 mmol) in THF (10 mL) and water (0.19 g) were added. The resulting mixture was stirred under argon at 50° C. for 1 hour. After this time resin was filtered off, THF remove in vacuo. The residue was dissolved in MeOH (10 mL), AcOH (1 mL) and sodium cyanoborohydride (200 mg, 3.2 mmol) added and resulting mixture stirred at room temperature for 2 hours, then quenched with concentrated HCl (1 mL), treated with saturated aqueous NaHCO$_3$ (15 mL) and basified with 1N sodium hydroxide (3 mL). Product was extracted with CH$_2$Cl$_2$ (3×50 mL), combined organics washed with water (2×30 mL), brine (30 mL), dried (MgSO$_4$) and evaporated in vacuo to afford pyrrolidine intermediate 71c (258 mg, 0.97 mmol, 74%) as yellow foam. Intermediate 71c was used without further purification.

d) Methyl(3aS,12bS)-11-fluoro-3-methylene-3,3a,8,12b-tetrahydrodibenzo-[3,4:6,7]cyclo-hepta[1,2-b]pyrrole-1(2H)-carboxylate (Intermediate 71d)

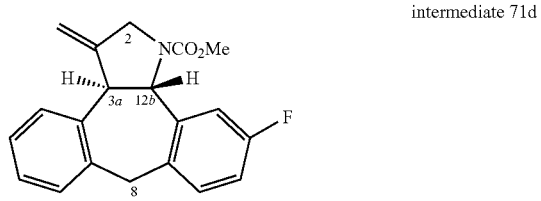

intermediate 71d

Reaction of intermediate 71c (258 mg, 0.97 mmol) was carried out in the same way as described for compound 9. Flash chromatography (Kieselgel 60, 230-400 mesh, heptane-EtOAc 50/50 to 0/100) afforded intermediate 71d (282 mg, 0.87 mmol, 90%) as yellow oil.

e) Methyl(3aR,12bS)-11-fluoro-3-(hydroxymethyl)-3,3a,8,12b-tetrahydrodibenzo-[3,4:6,7]-cyclohepta[1,2-b]pyrrole-1(2H)-carboxylate (Intermediate 71e)

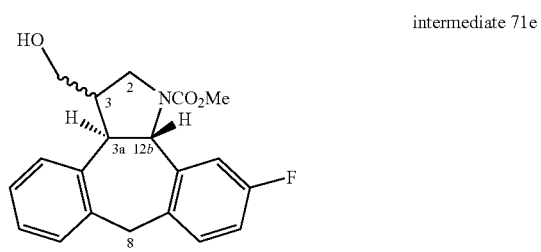

intermediate 71e

Reaction of 71d (255 mg, 0.79 mmol) was carried out obtained in the same way as described for compound 49.

Flash chromatography (Kieselgel 60, 230-400 mesh, EtOH—CH$_2$Cl$_2$ 1/99 to 3/97) afforded 71e (215 mg, 0.63 mmol, 80%) as colorless oil.

f) Methyl(3aR,12bS)-3-(azidomethyl)-11-fluoro-3,3a,8,12b-tetrahydrodibenzo-[3,4:6,7]-cyclohepta[1,2-b]pyrrole-1(2H)-carboxylate (Intermediate 71f)

intermediate 71f

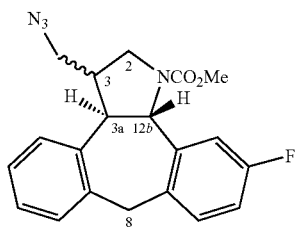

Reaction of intermediate 71f (215 mg, 0.63 mmol) was carried out obtained in the same way as described for compound 50. Flash chromatography (Kieselgel 60, 230-400 mesh, ethyl acetate) afforded intermediate 71f (194 mg, 0.53 mmol, 84%) as colorless oil.

B. Preparation of the Final Compounds

The compounds prepared hereinunder all are mixtures of isomeric forms, unless otherwise specified.

Example B1

(4aS,13bR,14aS)-6-fluoro-2-methyl-1,2,3,4a,9,13b,14,14a-octahydrodibenzo-[3',4':6',7']cyclohepta[1',2':4,5]pyrrolo[1,2-c]imidazole (Final Compound 1)

final compound 1

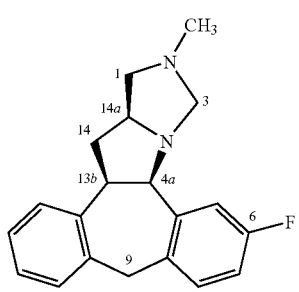

To a solution of diamine intermediate 9 (130 mg, 0.3 mmol) in MeOH (5 mL) was added Et$_3$N (126.5 mL, 0.91 mmol) and the mixture was hydrogenated at 1 atmospheric pressure with 10% palladium-on-charcoal under vigorous stirring at room temperature. After 1 hour, formaldehyde (112.8 mL, 1.5 mmol) was added and the mixture was hydrogenated for an additional hour. The suspension was then filtered through a pad of celite and the solids were washed 4 times with CH$_2$Cl$_2$. After evaporation, the crude product was purified by column chromatography on silica gel using CHCl$_3$/MeOH (95/5). This yielded final compound 1 as an oil (50.5 mg, 54%).

Mass spectrum: —CI m/z (assignment, relative intensity) 309 (MH$^+$, 100%), 289 (MH$^+$—HF, 26%); EI: m/z (assignment, relative intensity) 308 (M$^+$, 68%), 279 (M$^+$. —CH$_2$NH, 4%), 265 (M$^+$. —CH$_3$NCH$_2$, 100%), 197 (23%); High resolution EI Calculated C$_{20}$H$_{21}$FN2 (M$^+$·): 308.1689, Found: 308.1684 (35%).

Example B2

[(2S,3aR,12bS)-11-fluoro-1,2,3,3a,8,12b-hexahydrodibenzo[3,4:6,7]cyclohepta[1,2-b]pyrrol-2-yl]N,N-dimethylmethanamine (Final Compound 2)

final compound 2

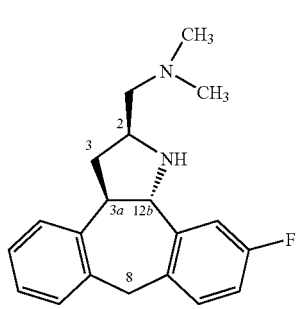

Dissolve the above compound 1 (0.114 g, 0.37 mmol) in MeOH (10 mL) and add TFA (0.071 mL, 0.93 mmol), NaCNBH$_3$ (0.058 g, 0.93 mmol) and stir at room temperature for 1 hour. Add 10 mL K$_2$CO$_3$ (sat. aq. solution), extract with CH$_2$Cl$_2$ (3×10 mL) and dry with MgSO$_4$. Column purification on silica gel using CH$_2$Cl$_2$/MeOH (10%) gave final compound 2 as an oil (0.067 g, 59%).

Mass spectrum: —CI m/z (assignment, relative intensity) 311 (MH$^+$, 100%), 291 (MH$^+$—HF, 25%), 282 (MH$^+$—CH$_2$NH), 266 (MH$^+$—HN(CH$_3$)$_2$, 13%), 252 (8%); EI: m/z (assignment, relative intensity) 310 (M$^+$, 26%), 266 (M$^+$·—(CH$_3$)$_2$N, 76%), 252 (M$^+$·—(CH$_3$)$_2$NCH$_2$, 70%), 235 (100%), 209 (61%); High resolution EI Calculated C$_{20}$H$_{23}$FN2 (M$^+$·): 310.1845, Found: 310.1820 (5%).

Example B3

(4aS,13bR,14aS)-6-fluoro-1,4a,9,13b,14,14a-hexahydrodibenzo[3',4':6',7']cyclohepta[1',2':4,5]pyrrolo[1,2-c]imidazole-3(2H)-thione (Final Compound 3)

final compound 3

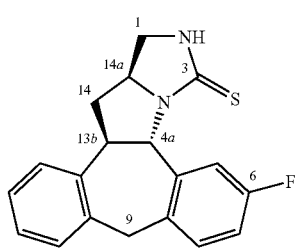

To solution of the diamine intermediate 9 (238.6 mg, 0.85 mmol) in DMF (3 mL) was added carbon disulfide (0.076 mL, 1.28 mmol). Stir at 60° C. for 20 minutes. After evaporation of the solvent, the residue was purified by column chromatography on silica gel using EtOAc/heptane (50/50) to give compound 3 as a semisolid final compound (124.6 mg, 45%).

Mass spectrum: —CI m/z (assignment, relative intensity) 325 (MH⁺, 100%), 252 (1%), 224 (2%).

Example B4

(5aS,14bR,15aS)-7-fluoro-2-methyl-1,2,3,5a,10,14b,15,15a-octahydro-4H-dibenzo[3',4':6',7']cyclohepta[1',2':4,5]pyrrolo[1,2-a]pyrazin-4-one (Final Compound 4)

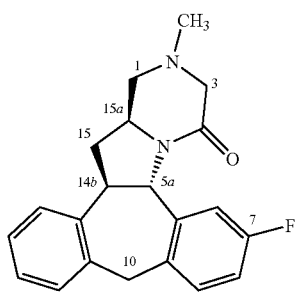

final compound 4

A solution of the above carbamate intermediate 16 (86.2 mg, 0.19 mmol) in MeOH (3 mL) was hydrogenated at 1 atmospheric pressure with 10% palladium-on-charcoal under vigorous stirring at room temperature. After reaction for 1 hour, formaldehyde (70.7 µL, 0.94 mmol) was added and the mixture was hydrogenated for an additional hour. The suspension was filtered through a pad of celite and the solids were washed 4 times with $CH_2Cl_2$. After evaporation of the solvent, the crude product was purified by column chromatography on silica gel using $CHCl_3$ to yield final compound 4 (18.6 mg, 29%).

Mass spectrum: —CI m/z (assignment, relative intensity) 337 (MH⁺, 100%), 317 (MH⁺—HF, 18%), 309 (MH⁺—CO, 9%), 161 (9%), 133 (75%), 93 (72%).

Example B5

[(2R,3aR,12bS)-11-fluoro-1-methyl-1,2,3,3a,8,12b-hexahydrodibenzo[3,4:6,7]-cyclohepta[1,2-b]pyrrol-2-yl]-N,N-dimethylmethanamine (Final Compound 5)

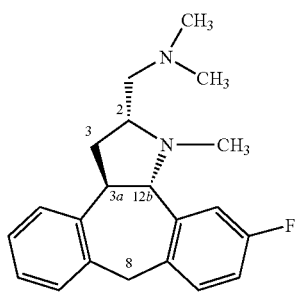

final compound 5

To a solution of diamine intermediate 13 (28.7 mg, 0.05 mmol) in MeOH (2 mL) was added Et₃N (21.4 µL, 0.15 mmol) and formaldehyde (18.8 µL, 0.25 mmol) and the mixture was treated with hydrogen under 1 atmospheric pressure and 10% palladium-on-charcoal under vigorous stirring at room temperature. After reaction for 1 hour, the suspension was filtered through a pad of celite and the solids were washed 4 times with $CH_2Cl_2$. After evaporation, the crude product was purified by column chromatography on silica gel using $CHCl_3$/MeOH (90/10). This afforded final compound 5 as an oil (16.7 mg, 98%).

Mass spectrum: —CI m/z (assignment, relative intensity) 325 (MH⁺, 100%), 323 (25%), 305 (MH⁺—HF, 19%), 280 (MH⁺—HN(CH₃)₂, 12%), 266 (MH⁺—CH₃N(CH₃)₂, 36%).

Example B6

(4aS,13bR,14aR)-6-fluoro-1,4a,9,13b,14,14a-hexahydrodibenzo[3',4':6',7']-cyclohepta[1',2':4,5]pyrrolo[1,2-c]imidazol-3(2H)-one (Final Compound 6)

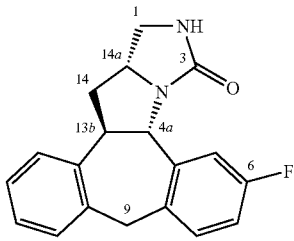

final compound 6

To a solution of diamine intermediate 13 (40.4 mg, 0.14 mmol) in CH₃CN (2 mL) was added Et₃N (50 mL, 0.36 mmol) and the mixture was heated under argon at 70° C. After 1 hour, a solution of diphenyl carbonate (36.6 mg, 0.17 mmol) in CH₃CN was added dropwise and the mixture was stirred at 70° C. for 2 days. After evaporation, the crude product was purified by column chromatography on silica gel using EtOAc/heptane (20/80) to yield urea final compound 6 as an oil (23 mg, 52%).

Mass spectrum: —CI m/z (assignment, relative intensity) 309 (MH⁺, 100%), 308 (12%), 289 (MH⁺—HF, 20%), 279 (3%), 113 (8%).

Example B7

(4aS,13bR,14aR)-6-fluoro-2-methyl-1,4a,9,13b,14,14a-hexahydrodibenzo-[3',4':6',7']cyclohepta[1',2':4,5]pyrrolo[1,2-d]imidazol-3(2H)-one (final compound 7)

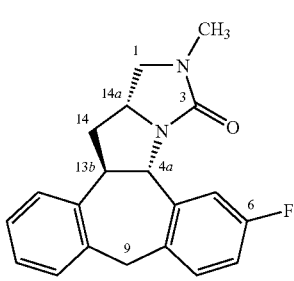

final compound 7

To a solution of urea compound 6 (29 mg, 0.10 mmol) in THF (3 mL) was added NaH (15.9 mg, 0.31 mmol) and the mixture was stirred at room temperature for 20 minutes. Then Me₂SO₄ (25.4 mg, 0.26 mmol) was added and the mixture was stirred for an additional 30 minutes. Add 10 mL of NH₄Cl (sat. aq. solution), extract with CH₂Cl₂ (3×10 mL) and dry with MgSO₄. Column purification on silica gel using EtOAc/heptane (40/60) gave the methylated urea final compound 7 as an oil (19 mg, 63%).

Mass spectrum: —CI m/z (assignment, relative intensity) 323 (MH⁺, 100%), 303 (MH⁺—HF, 26%), 209 (2%), 127 (3%).

Example B8

(4aS,13bR,14aR)-6-fluoro-1,4a,9,13b,14,14a-hexahydrodibenzo[3',4':6',7']-cyclohepta[1',2':4,5]pyrrolo[1,2-c]imidazole-3(2H)-thione (Final Compound 8)

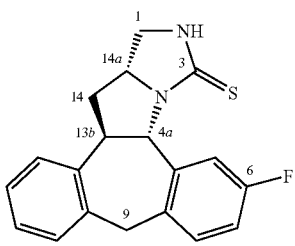

final compound 8

To a solution of the diamine intermediate 13 (54 mg, 0.19 mmol) in DMF (3 mL) was added carbon disulfide (17.3 µL, 0.29 mmol). After stirring at 60° C. for 20 minutes, followed by evaporation of the solvent, column purification on silica gel (eluent: EtOAc/heptane (50/50)) gave a crystalline final compound 8 (27.3 mg, 44%); mp: 150-151° C.

Mass spectrum: —CI m/z (assignment, relative intensity) 325 (MH⁺, 100%), 252 (1%), 224 (2%).

Example B9

(4aS,13bR,14aR)-6-fluoro-3-(methylsulfanyl)-1,4a,9,13b,14,14a-hexahydrodibenzo[3',4':6',7']cyclohepta[1',2':4,5]pyrrolo[1,2-c]imidazole (Final Compound 9)

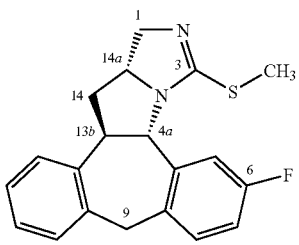

final compound 9

To a solution of final compound 8 (140.6 mg, 0.43 mmol) in MeOH (10 mL) was added methyl iodide (53.5 µL, 0.86 mmol) and Et₃N (129 µl, 0.86 mmol). After stirring at 80° C. for 2 days, solvent and reagents were evaporated. Column purification on silica gel (eluent: EtOAc/heptane (40/60)) gave the S-methylated final compound 9 as an oil (72.7 mg, 49%).

Mass spectrum: —CI m/z (assignment, relative intensity) 339 (MH⁺, 100%), 319 (MH⁺—HF, 4%), 268 (8%), 266 (3%).

Example B10

[(2R,3aR,12bS)-11-fluoro-1-(methoxyacetyl)-1,2,3,3a,8,12b-hexahydrodibenzo-[3,4:6,7]cyclohepta[1,2-b]pyrrol-2-yl]-N,N-dimethylmethanamine (final compound

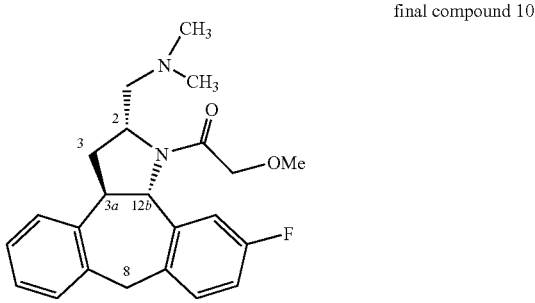 [SMILES: COCC(=O)N1[C@@H](CN(C)C)C[C@@H]2c3ccccc3Cc3ccc(F)cc3[C@H]21]

final compound 10

To a solution of intermediate 19 (265.3 mg, 0.44 mmol) in MeOH (20 mL) was added MeSO₃H (2 mL) and the mixture was stirred at 60° C. for 30 minutes. After evaporation of the solvent, NaHCO₃ (sat. aq. solution) (15 mL) was added and the mixture was extracted with CH₂Cl₂ (3×10 mL). The combined organic layers were dried with MgSO₄. Column purification on silica gel using CH₂Cl₂/MeOH (5%) gave the amino compound (125 mg, 79%). The latter was then dissolved in MeOH (30 mL). Following addition of formaldehyde (80 µL, 1.06 mmol) the mixture was hydrogenated (1 atm.) with 10% palladium-on-charcoal under vigorous stirring at room temperature for 6 hours. The suspension was then filtered through a pad of celite and the solids were washed 4 times with CH₂Cl₂. After evaporation of the solvent, the crude product was purified by column chromatography on silica gel using CHCl₃/MeOH (95/5). Final compound 10 (90.1 mg, 67%) was obtained as an oil (mixture of conformers).

Mass spectrum: -APCI m/z (assignment, relative intensity) 383 (MH⁺, 100%), 369 (4%), 367 (4%), 363 (MH⁺—HF, 5%), 354 (2%), 351 (2%).

Example B11

Methyl({[(2R,3aR,12bS)-11-fluoro-1,2,3,3a,8,12b-hexahydrodibenzo[3,4:6,7]cyclohepta[1,2-b]pyrrol-2-yl]methyl}amino)acetate (Final Compound 11)

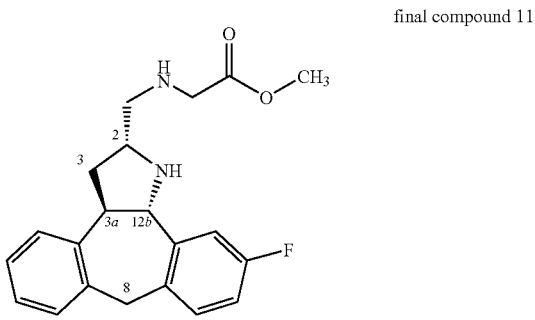 [SMILES: COC(=O)CNC[C@H]1C[C@@H]2c3ccccc3Cc3ccc(F)cc3[C@H]2N1]

final compound 11

Intermediate 21 (53.4 mg, 0.15 mmol) was dissolved in a sat. solution of HCl in MeOH (10 mL) and the mixture was stirred at 60° C. overnight. After removal of solvent, 10 mL of $K_2CO_3$ (sat. aq. solution) was added and the mixture extracted with $CH_2Cl_2$ (3×10 mL). Column purification on silica gel using $CHCl_3$/MeOH (97/3) gave the amino ester compound 11 (20 mg, 37%) as an oil.

Mass spectrum: —CI m/z (assignment, relative intensity) 355 ($MH^+$, 100%), 335 ($MH^+$—HF, 14%), 295 ($MH^+$—$CH_3OH$—CO, 4%), 252 ($MH^+$—$CH_3OH$—$CH_2CO$—$NHCH_2$, 8%), 169 (5%), 141 (46%); EI m/z (assignment, relative intensity) 354 ($M^+$, 3%), 295 ($M^+$—$CH_3OCO$, 4%), 252 ($M^+$—$CH_3OCOCH_2NHCH_2$, 100%), 235 ($M^+$—$CH_3OCOCH_2NHCH_2$—$NH_3$, 68%), 223 (8%), 209 (22%); High resolution EI Calculated $C_{21}H_{23}N_2O_2F$ ($M^{+\cdot}$): 354.1744, Found: 354.1751 (9%).

Example B12

(5aS,14bR,15aR)-7-fluoro-1,2,3,5a,10,14b,15,15a-octahydro-4H-dibenzo[3',4':6',7']cyclohepta[1',2':4,5]pyrrolo[1,2-a]pyrazin-4-one (Final Compound 12)

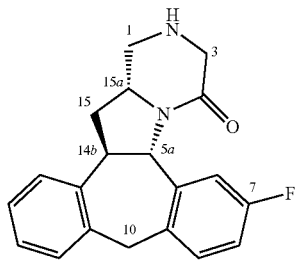

final compound 12

Intermediate 21 (250 mg, 0.71 mmol) was dissolved in 10 mL of HCl in MeOH (sat solution) and the mixture was stirred at room temperature overnight. The reaction was quenched by addition of 10 mL of $K_2CO_3$ (sat. aq. solution). The mixture was then extracted 3 times with 10 mL $CH_2Cl_2$. The combined organic layers were dried over $MgSO_4$ and evaporated. Column purification on silica gel using $CHCl_3$/MeOH (95/5) gave final compound 12 (67.6 mg, 29%) as an oil.

Mass spectrum: —CI m/z (assignment, relative intensity) 323 ($MH^+$, 100%), 303 ($MH^+$—HF, 20%), 295 ($MH^+$—CO, 2%), 252 ($MH^+$—$COCH_2$—$NHCH_2$, 1%), 188 (2%), 160 (5%); EI m/z (assignment, relative intensity) 322 ($M^+$, 100%), 252 ($M^+$—$COCH_2N$=$CH_2$, 40%), 235 (68%), 223 ($M^+$—$COCH_2N$=$CH_2$—$CH_2NH$, 44%), 207 (13%), 209 (88%), 209 (22%); High resolution EI Calculated $C_{20}H_{19}N_2OF$ ($M^{+\cdot}$): 322.1481, Found: 322.1484 (100%).

Example B13

(5aS,14bR,15aR)-7-fluoro-2-methyl-1,2,3,5a,10,14b,15,15a-octahydro-4H-dibenzo-[3',4':6',7']cyclohepta[1',2':4,5]pyrrolo[1,2-a]pyrazin-4-one (Final Compound 13)

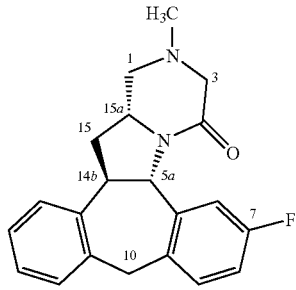

final compound 13

To a solution of final compound 12 (82.3 mg, 0.25 mmol) in MeOH (10 mL) was added formaldehyde (96 μL, 1.22 mmol) and the mixture was hydrogenated (1 atm.) with 10% palladium-on-charcoal under vigorous stirring at room temperature for 1 hour. Then the mixture was filtered through a pad of celite and the solids were washed 4 times with $CH_2Cl_2$. After evaporation, the crude product was purified by column chromatography on silica gel using $CHCl_3$/MeOH (3%) as eluent. Final compound 13 (43.4 mg, 50%) was obtained as a solid; mp: 139-141° C.

Mass spectrum: —CI m/z (assignment, relative intensity) 337 ($MH^+$, 100%), 317 ($MH^+$—HF, 30%), 279 (1%), 251 (1%), 209 (1%); EI m/z (assignment, relative intensity) 336 ($M^+$, 74%), 293 ($M^+$—$COCH_3$, 13%), 265 ($M^+$—CO=$CHNHCH_3$, 9%), 233 (18%), 209 (42%), 196 (26%), 57 (100%); High resolution EI Calculated $C_{21}H_{21}N_2OF$ ($M^{+\cdot}$): 336.1638, Found: 336.1641 (100%).

Example B14

(5aS,14bR,15aR)-7-fluoro-2-methyl-1,3,4,5a,10,14b,15,15a-octahydro-2H-dibenzo-[3',4':6',7']cyclohepta[1',2':4,5]pyrrolo[1,2-a]pyrazine (Final Compound 14)

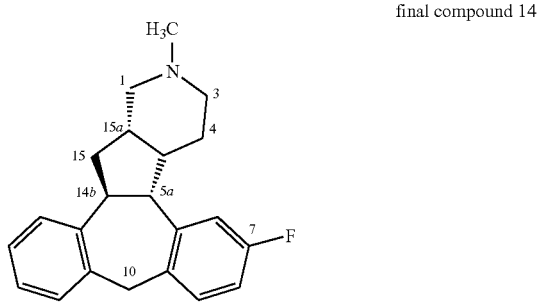

final compound 14

To a solution of final compound 13 (34.3 mg, 0.1 mmol) in THF (10 mL) was added $BH_3.Me_2S$ (100 μL, 0.2 mmol) and the mixture was heated at 85° C. overnight. Following evaporation of the solvent the residue was dissolved in 10 mL of HCl in MeOH (sat. solution) and the mixture was refluxed for 30 minutes. After removal of the solvent 10 mL of $K_2CO_3$ (sat. aq. solution) was added and the solution extracted 4 times with $CH_2Cl_2$. Then, the combined organic layers were evaporated and the crude product was purified by column chromatography on silica gel using $CHCl_3$/MeOH (3%) as eluent. Final compound 14 (15.9 mg, 50%) was obtained as an oil.

Mass spectrum: —CI m/z (assignment, relative intensity) 323 ($MH^+$, 73%), 303 ($MH^+$—HF, 18%), 247 (4%), 219 (3%), 43 (100%); EI m/z (assignment, relative intensity) 322 ($M^+$, 73%), 278 ($M^+$—$N(CH_3)_2$, 44%), 266 ($M^+$—$N(CH_2)_3$, 85%), 264 ($M^+$—$CH_2CH_2NHCH_3$, 94%), 251 ($M^+$—$CH_2CH_2$—$CH_2N(CH_3)$, 100%), 209 (68%), 196 (38%); High resolution EI Calculated $C_{21}H_{23}N_2F$ ($M^{+\cdot}$): 322.1845, Found: 322.1849 (100%).

Example B15

(4aS,13bR,14aS)-6-fluoro-1,4a,9,13b,14,14a-hexahydrodibenzo[3',4':6',7']-cyclohepta[1',2':4,5]pyrrolo[1,2-c]imidazol-3(2H)-one (Final Compound 15)

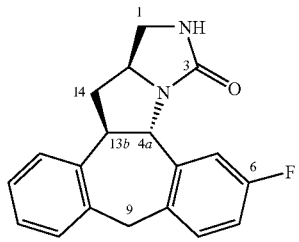

final compound 15

To the above intermediate 25 (13.5 mg, 0.04 mmol) in $CH_2Cl_2$ (1 mL) was added $CH_3SO_3H$ (1.3 μL, 0.02 mmol). After stirring at room temperature for 1 minute, the mixture was worked up by adding $Na_2CO_3$ (sat. aq. sol.). Extract 3 times with $CH_2Cl_2$ and dry with $MgSO_4$. Column purification on silica gel using $CHCl_3$/MeOH (95/05) gave final compound 15 as an oily product (10.5 mg, 82%).

Mass spectrum: —CI m/z (assignment, relative intensity) 309 ($MH^+$, 100%), 289 ($MH^+$—HF, 17%), 257 (1%).

Example B16

(4aS,13bR,14aS)-6-fluoro-2-methyl-1,4a,9,13b,14,14a-hexahydrodibenzo-[3',4':6',7']cyclohepta[1',2':4,5]pyrrolo[1,2-c]imidazol-3(2H)-one (final compound 16)

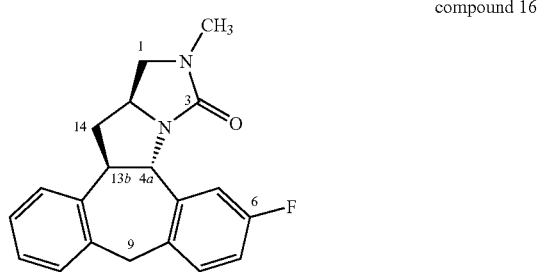 [SMILES: CN1C[C@@H]2C[C@@H]3c4ccccc4Cc4ccc(F)cc4[C@H]3N2C1=O]

compound 16

To a solution of imidazolone final compound 15 (10 mg, 0.03 mmol) in THF (1 mL) was added NaH (5 mg, 0.1 mmol) and the mixture was stirred at room temperature for 20 minutes. Then $Me_2SO_4$ (8 μL, 0.08 mmol) was added and the mixture was stirred for additional 30 min. Add 10 mL of $NH_4Cl$ (sat. aq. solution), extract with $CH_2Cl_2$ (3×10 mL) and dry with $MgSO_4$. Column purification on silica gel using EtOAc/heptane (50/50) gave the N-methylated imidazolonefinal compound 16 (8.4 mg, 80%) as an oil.

Mass spectrum: —CI m/z (assignment, relative intensity) 323 ($MH^+$, 100%), 303 ($MH^+$—HF, 6%), 257 (11%), 252 ($MH^+$—$CH_2N(CH_3)CO$, 9%), 229 (9%).

Example B17

[(2R,3aR,12bS)-11-fluoro-2,3,3a,12b-tetrahydro-1H-dibenzo[2,3:6,7]oxepino[4,5-b]pyrrol-2-yl]-N,N-dimethylmethanamine (Final Compound 17)

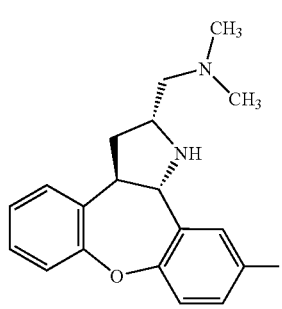

compound 17

To a solution of intermediate 38 (0.17 g, 0.5 mmol), $CH_2O$ (3 eq) and AcOH (3 eq) in MeOH (5 mL) at 0° C., $NaCNBH_3$ (4 eq) was added in several lots. The reaction mixture was warmed to room temperature and stirred for 6 hours. Solid $NaHCO_3$ (0.5 g) was added to the reaction mixture and stirred for 0.5 hour. To remove inorganic complexes the reaction mixture was put on sort filtration column and diluted with $CH_2Cl_2$:MeOH (9.5:0.5). The crude intermediate

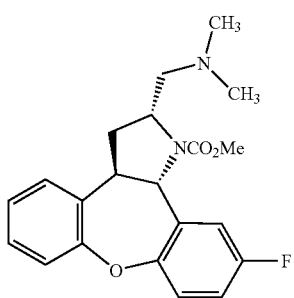

thus obtained was dissolved in i-PrOH (4 mL) and a solution of KOH (56 mg) in water (0.5 mL) was added to it and then refluxed for 3 hours. Silica was added to the reaction mixture and the solvent was removed under reduced pressure followed by purification of compound by flash chromatography using $CH_2Cl_2$:MeOH (9:1) as an eluant to obtain final compound 17 as a thick viscous liquid (60%, 93 mg).

HRMS: Calculated 312.1638; found 312.1633.

Examples B18-20 a) To a solution of intermediate 39 (0.5 mmol, 0.33 g) in dioxane (5 mL) the corresponding amino alcohol (5 eq) was added and then refluxed for 6 hours. The solvent was removed under reduced pressure followed by chromatography (silica gel) using $CH_2Cl_2$:MeOH (9:1) as an eluant to obtain intermediates 39a, 39b and 39c as a thick viscous liquids in 40-50% overall yield.

intermediate 39a

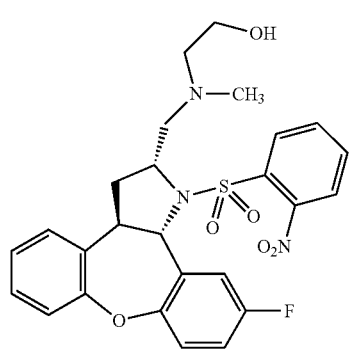

intermediate 39b

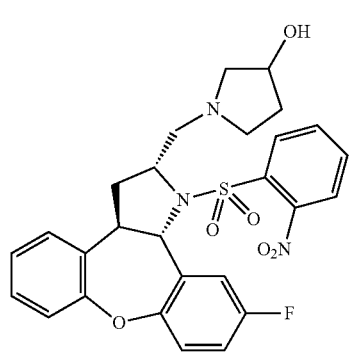

intermediate 39c

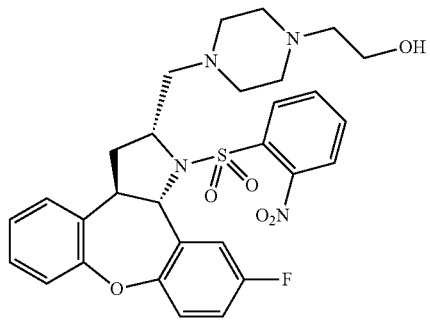

b) A mixture of appropriate nosylamide intermediates 39a, 39b and 39c (ca. 0.4 mmol), thiophenol (110 mg, 1.0 mmol), anhydrous $K_2CO_3$ (138 mg, 1 mmol) and DMF (20 mL) was stirred at 80° C. for 4 hours, cooled to ambient temperature, diluted with water, product extracted with EtOAc (3×50 mL), combined organics washed with water (4×50 mL), brine (35 mL), dried ($K_2CO_3$), evaporated and purified by solid phase extraction on basic alumina (Brockmann II, heptane-ethyl acetate 50/50, then ethyl acetate-MeOH 100/0 to 96/4 to 90/10) to obtain final compounds 18, 19 and 20.

2-[{[(2R,3aR,12bS)-11-fluoro-2,3,3a,12b-tetrahydro-1H-dibenzo[2,3:6,7]oxepino-[4,5-b]pyrrol-2-yl]methyl}(methyl)amino]ethanol (Final Compound 18)

final compound 18

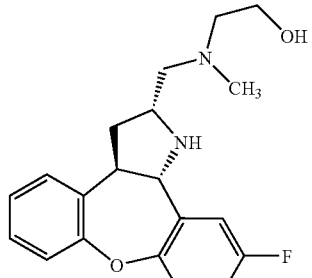

HRMS: Calculated 342.1744; found 342.1750

2-(4-{[(2R,3aR,12bS)-11-fluoro-2,3,3a,12b-tetrahydro-1H-dibenzo[2,3:6,7]-oxepino[4,5-b]pyrrol-2-yl]methyl}-1-piperazinyl)ethanol (Final Compound 19)

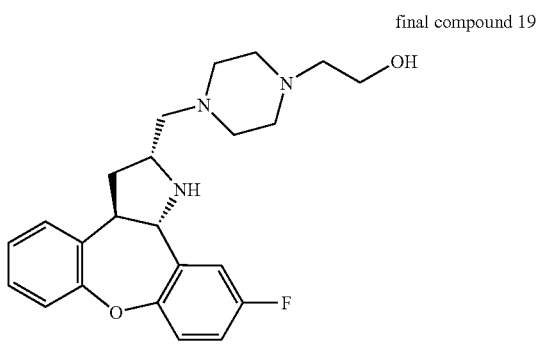 [SMILES: OCCN1CCN(C[C@H]2C[C@@H]3c4ccccc4Oc4ccc(F)cc4[C@H]3N2)CC1]

HRMS: Calculated 397.2166 found 397.2158

1-{[(2R,3aR,12bS)-11-fluoro-2,3,3a,12b-tetrahydro-1H-dibenzo[2,3:6,7]oxepino-[4,5-b]pyrrol-2-yl]methyl}-3-pyrrolidinol (Final Compound 20)

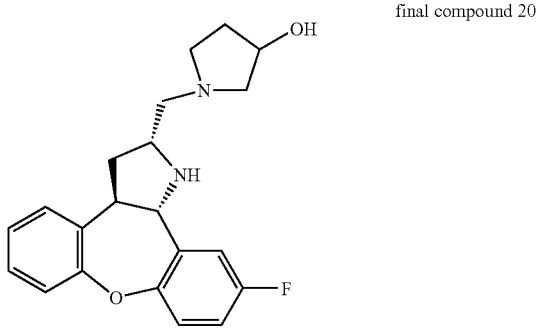 [SMILES: OC1CCN(C[C@H]2C[C@@H]3c4ccccc4Oc4ccc(F)cc4[C@H]3N2)C1]

HRMS: Calculated 354.1744; found 354.1755

Example B21

[(2S,3aR,12bS)-11-fluoro-3,3a,8,12b-tetrahydro-2H-dibenzo[3,4:6,7]cyclohepta-[1,2-b]thien-2-yl]-N,N-dimethylmethanamine (Final Compound 21)

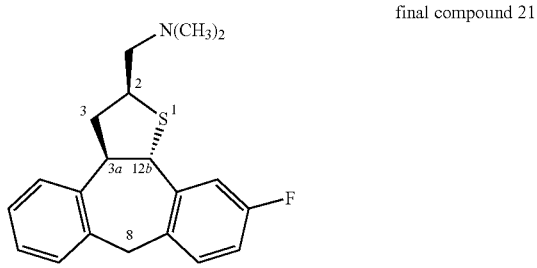 [SMILES: CN(C)C[C@@H]1C[C@@H]2c3ccccc3Cc3ccc(F)cc3[C@H]2S1]

To a solution of above intermediate 43 (81 mg, 0.25 mmol) in THF and water (3 mL/1 mL) was added Ph₃P (0.13 g, 0.50 mmol). The reaction mixture was stirred at room temperature for 1 night. After evaporation of the solvent, MeOH (5 mL), HCHO (37 wt % aq. solution, 0.20 mL, 2.5 mmol), AcOH (1 mL) and NaCNBH₃ (75 mg, 1.20 mmol) were added. Stirring was continued at room temperature for 1 day. Add Na₂CO₃ (sat. aq. sol.), extract 3 times with CH₂Cl₂. Column purification on silica gel using EtOAc gave final compound 21 as an oily product (70 mg, 86%).

Mass spectrum: —CI m/z (assignment, relative intensity) 328 (MH⁺, 100%), 308 (MH⁺—HF, 20%), 283 (MH⁺-Me₂NH, 40%), 249 (MH⁺-Me₂NH—H₂S, 12%).

Example B22

[(2S,3aR,12bS)-11-fluoro-1,1-dioxido-3,3a,8,12b-tetrahydro-2H-dibenzo[3,4:6,7]-cyclohepta[1,2-b]thien-2-yl]-N,N-dimethylmethanamine (Final Compound 22)

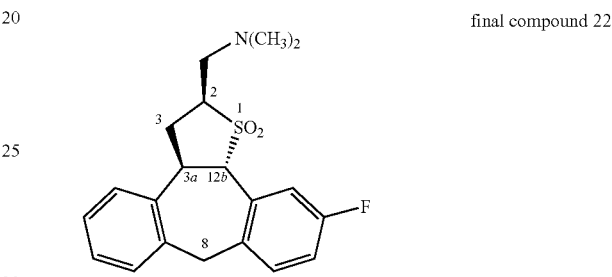

To a solution of above sulfone azide intermediate 44 (133.5 mg, 0.37 mmol) in THF (8 mL) was added water (67.0 μL, 3.74 mmol) and Ph₃P (0.13 g, 0.50 mmol). The reaction mixture was stirred at room temperature for 1 night. After evaporation of the solvent, 5 mL of MeOH, HCHO (37 wt % aq. solution, 0.24 mL, 2.98 mmol), AcOH (0.5 mL) and NaCNBH₃ (94 mg, 1.49 mmol) were added. Stirring was continued at room temperature for 1 day. Add Na₂CO₃ (sat. aq. sol.), extract 3 times with CH₂Cl₂. Column purification on silica gel using CH₂Cl₂/MeOH (95/05) gave final compound 22 as an oil product (60.7 mg, 45%).

Mass spectrum: —CI m/z (assignment, relative intensity) 360 (MH⁺, 100%), 358 (6%), 340 (MH⁺—HF, 12%), 303 (8%), 294 (MH⁺H₂SO₂, 4%), 250 (1%).

Example B23

[(2R,3aR,12bS)-11-fluoro-3,3a,8,12b-tetrahydro-2H-dibenzo[3,4:6,7]cyclohepta-[1,2-b]thien-2-yl]-N,N-dimethylmethanamine (Final Compound 23)

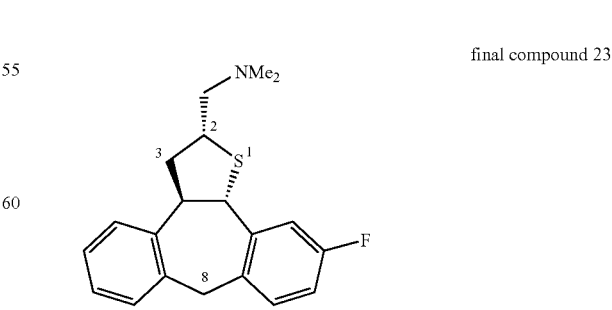

To a solution of above intermediate 47 (0.15 g, 0.46 mmol) in THF and water (5 mL/1 mL) was added Ph₃P (0.13 g, 0.50 mmol). After stirring at room temperature for 1 night and evaporation of the solvent, 5 mL of MeOH, HCHO (37 wt % aq. solution, 0.20 mL, 2.5 mmol), AcOH (1 mL) and NaCNBH$_3$ (75 mg, 1.20 mmol) were added. Stirring was continued at room temperature for 1 day. Add Na$_2$CO$_3$ (sat. aq. sol.), extract 3 times with CH$_2$Cl$_2$. Column purification on silica gel using EtOAc gave final compound 23 as an oily product (70 mg, 86%).

Mass spectrum: —CI m/z (assignment, relative intensity) 328 (MH$^+$, 100%), 308 (MH$^+$HF, 20%), 283 (MH$^+$-Me$_2$NH, 40%), 249 (MH$^+$-Me$_2$NH—H$_2$S, 12%).

Example B24

[(2R,3aR,12bS)-11-fluoro-1,1-dioxido-3,3a,8,12b-tetrahydro-2H-dibenzo[3,4:6,7]-cyclohepta[1,2-b]thien-2-yl]-N,N-dimethylmethanamine (Final Compound 24)

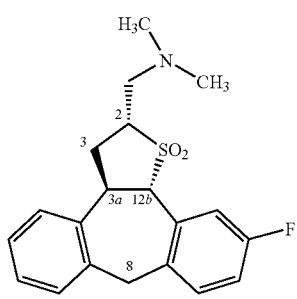

final compound 24

To a solution of above sulfone azide intermediate 48 (146.5 mg, 0.41 mmol) in THF (8 mL) was added water (74.0 µL, 4.10 mmol) and Ph$_3$P (0.215 mg, 0.82 mmol). The reaction mixture was stirred at room temperature for 1 night. After evaporation of the solvent, 5 mL of MeOH, HCHO (37 wt % aq. solution, 0.28 mL, 3.51 mmol), AcOH (0.5 mL) and NaCNBH$_3$ (110.0 mg, 1.75 mmol) were added. Stirring was continued at room temperature for 1 day. Add Na$_2$CO$_3$ (sat. aq. sol.), extract 3 times with CH$_2$Cl$_2$. Column purification on silica gel using CH$_2$Cl$_2$/MeOH (90/10) gave final compound 24 as an oily product (105.0 mg, 71%).

Mass spectrum: —CI m/z (assignment, relative intensity) 360 (MH$^+$, 100%), 358 (6%), 340 (MH$^+$—HF, 12%), 303 (8%), 294 (MH$^+$H$_2$SO$_2$, 4%), 250 (1%).

Example B25

[(2S,3aR,12bS)-11-fluoro-1-oxido-3,3a,8,12b-tetrahydro-2H-dibenzo[3,4:6,7]-cyclohepta[1,2-b]thien-2-yl]-N,N-dimethylmethanamine (Final Compound 25)

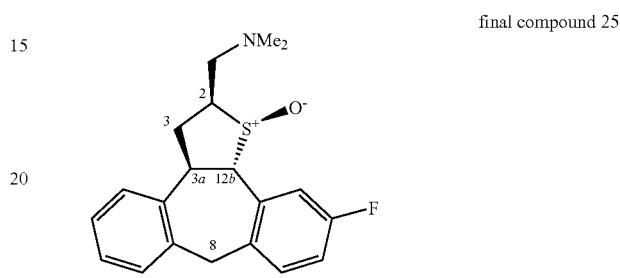

final compound 25

To a solution of above intermediate 49 (107.9 mg, 0.32 mmol) in THF (5 mL) was added water (57 µL, 3.16 mmol) and Ph$_3$P (166.0 mg, 0.63 mmol). The reaction mixture was stirred at room temperature for 1 night. After evaporation of the solvent 5 mL of MeOH, HCHO (37%, 0.26 mL, 3.33 mmol), AcOH (0.5 mL) and NaCNBH$_3$ (104.7 mg, 1.67 mmol) were added. Stirring was continued at room temperature for 1 day. Add Na$_2$CO$_3$ (sat. aq. sol.), extract 3 times with CH$_2$Cl$_2$. Column purification on silica gel using CH$_2$Cl$_2$/MeOH (95/05) gave final compound 25 as an oily product (80.4 mg, 74%).

Mass spectrum: —CI m/z (assignment, relative intensity) 344 (MH$^+$, 100%), 328 (MH$^+$—O, 13%), 326 (MH$^+$—H$_2$O, 15%), 324 (MH$^+$—HF, 15%), 182 (14%), 100 (27%).

Example B26

[(2S,3aR,12bS)-11-fluoro-1-oxido-3,3a,8,12b-tetrahydro-2H-dibenzo[3,4:6,7]-cyclohepta[1,2-b]thien-2-yl]-N,N-dimethylmethanamine (Final Compound 26)

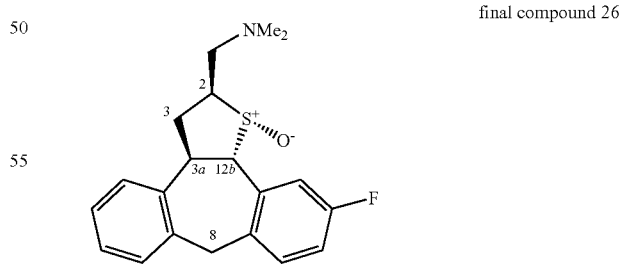

final compound 26

To a solution of above intermediate 50 (133.4 mg, 0.39 mmol) in THF (5 mL) was added water (70 µL, 3.91 mmol) and Ph$_3$P (205.2 mg, 0.78 mmol). The reaction mixture was stirred at room temperature for 1 night. After evaporation of the solvent, 5 mL of MeOH, HCHO (37%, 0.24 mL, 2.99 mmol), AcOH (0.4 mL) and NaCNBH$_3$ (94.0 mg, 1.50 mmol) were added. Stirring was continued at room temperature for 1 day. Add Na$_2$CO$_3$ (sat. aq. sol.), extract 3 times with CH$_2$Cl$_2$. Column purification on silica gel using CH$_2$Cl$_2$/MeOH (95/05) gave final compound 26 as an oily product (85.2 mg, 63%).

Mass spectrum: —CI m/z (assignment, relative intensity) 344 (MH$^+$, 100%), 328 (MH$^+$—O, 10%), 327 (12%), 326 (MH$^+$—H$_2$O, 46%), 324 (MH$^+$—HF, 22%), 283 (12%).

Example B27

[(2R,3aR,12bS)-11-fluoro-1-oxido-3,3a,8,12b-tetrahydro-2H-dibenzo[3,4:6,7]-cyclohepta[1,2-b]thien-2-yl]-N,N-dimethylmethanamine (Final Compound 27)

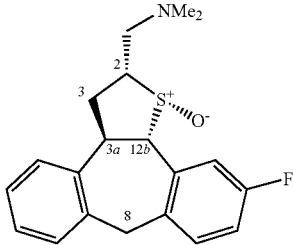

final compound 27

To a solution of intermediate 51 (85 mg, 0.25 mmol) in THF (5 mL) was added water (45 µL, 2.49 mmol) and Ph$_3$P (130.8 mg, 0.50 mmol). The reaction mixture was stirred at room temperature for 1 night. After evaporation of the solvent, 5 mL of MeOH, HCHO (37%, 0.08 mL, 1.03 mmol), AcOH (0.3 mL) and NaCNBH$_3$ (32 mg, 0.52 mmol) were added. Stirring was continued at room temperature for 1 day. Add Na$_2$CO$_3$ (sat. aq. sol.), extract 3 times with CH$_2$Cl$_2$. Column purification on silica gel using CH$_2$Cl$_2$/MeOH (95/05) gave final compound 27 as an oily product (35 mg, 41%).

Mass spectrum: —CI m/z (assignment, relative intensity) 344 (MH$^+$, 100%), 328 (MH$^+$—O, 4%), 327 (3%), 326 (MH$^+$—H$_2$O, 10%), 324 (MH$^+$—HF, 8%), 281 (6%).

Example B28

[(2R,3aR,12bS)-11-fluoro-1-oxido-3,3a,8,12b-tetrahydro-2H-dibenzo[3,4:6,7]-cyclohepta[1,2-b]thien-2-yl]-N,N-dimethylmethanamine (Final Compound 28)

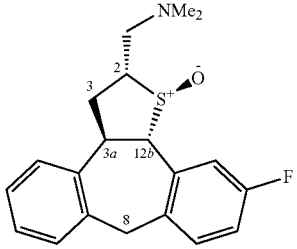

final compound 28

To a solution of above intermediate 52 (158.5 mg, 0.46 mmol) in THF (5 mL) was added water (84 µL, 4.65 mmol) and Ph$_3$P (243.8 mg, 0.93 mmol). The reaction mixture was stirred at room temperature for 1 night. After evaporation of the solvent, 5 mL of MeOH, HCHO (37%, 0.32 mL, 4.05 mmol), AcOH (0.5 mL) and NaCNBH$_3$ (130 mg, 2.03 mmol) were added. Stirring was continued at room temperature for 1 day. Add Na$_2$CO$_3$ (sat. aq. sol.), extract 3 times with CH$_2$Cl$_2$. Column purification on silica gel using CH$_2$Cl$_2$/MeOH (95/05) gave final compound 28 as an oily product (115.7 mg, 72%).

Mass spectrum: —CI m/z (assignment, relative intensity) 344 (MH$^+$, 100%), 328 (MH$^+$—O, 3%), 327 (3%), 326 (MH$^+$—H$_2$O, 13%), 324 (MH$^+$—HF, 14%), 281 (6%).

Example B29

(3R,4aR,13bR)-12-fluoro-2,3,4,4a,9,13b-hexahydrodibenzo[3,4:6,7]cyclohepta[1,2-b]pyran-3-ol (Final Compound 29)

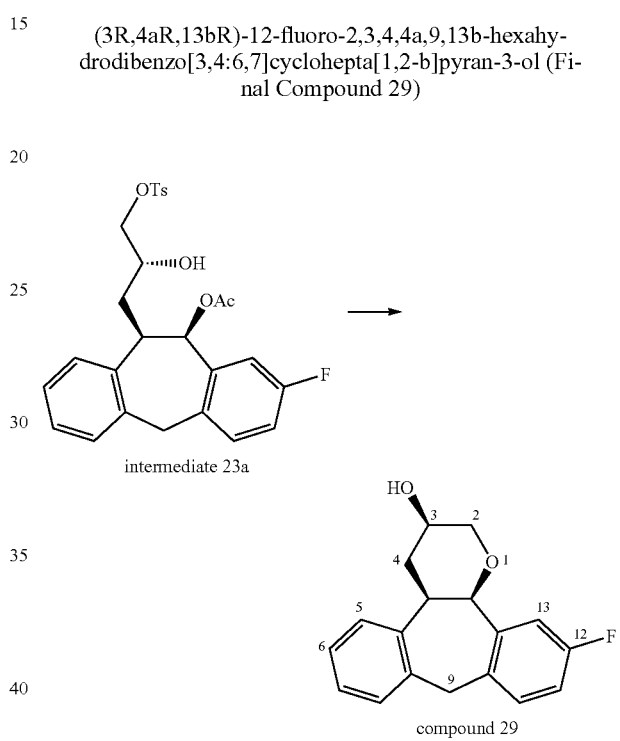

Dissolve intermediate 23a (1.31 g, 2.63 mmol) in CH$_2$Cl$_2$ (50 mL). Add dihydropyran (1.20 mL, 13.2 mmol) and camphorsulfonic acid (6 mg, 0.026 mmol). Stir at room temperature for 5 hours. Evaporate the solvent and dissolve the residue in 50 mL MeOH. Add K$_2$CO$_3$ (0.73 g, 5.26 mmol) and stir at room temperature for 1 night. Work up by adding sat. aq. NH$_4$Cl (30 mL), extract with CH$_2$Cl$_2$ (3×15 mL) and dry with MgSO$_4$. Evaporate the solvent and dissolve the residue in dry THF (50 mL). Add NaH (0.24 g, 7.78 mmol) and stir at room temperature for 1 day. Add 30 mL sat. aq. NH$_4$Cl, extract with CH$_2$Cl$_2$ (3×20 mL) and dry the organic phases with MgSO$_4$. Column purification on silica gel using ether/hexane (35/65) gave an oil (0.86 g, 90% from 2). Dissolve this oil (0.86 g, 2.34 mmol) in 20 mL MeOH/H$_2$O (9/1) and add Dowex 50WX8-100 (1.00 g). Heat the mixture at 50° C. for 1 night. Filter through a P3 filter, wash the solids with CH$_2$Cl$_2$ (5×15 mL) and evaporate the solvent. Column purification on silica gel using ether/hexane (70:30) yielded final compound 29 as an oil (0.61 g, 93%).

Mass spectrum: —CI m/z (assignment, relative intensity) 285 (MH$^+$, 25%), 267 (MH$^+$—H$_2$O, 100%), 249 (MH$^+$-2H$_2$O, 36%); EI: m/z (assignment, relative intensity) 284

($M^+$, 1%), 209 ($M^+$—CH$_2$CHOHCH$_2$OH, 100%); High resolution EI Calculated C$_{18}$H$_{17}$FO$_2$ ($M^+$): 284.1213, Found: 284.1204 (2%).

Example B30 a) (3R,4aR,13bR)-12-fluoro-2,3,4,4a,9,13b-hexahydrodibenzo[3,4:6,7]cyclohepta-[1,2-b]pyran-3-yl methanesulfonate (Intermediate 53)

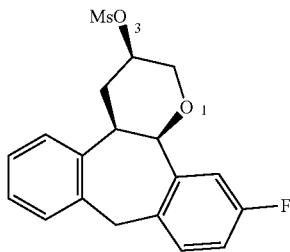

intermediate 53

Dissolve final compound 29 (0.61 g, 2.16 mmol) in CH$_2$Cl$_2$ (50 mL). Add Et$_3$N (0.60 mL, 4.32 mmol), DMAP (0.13 g, 1.08 mmol) and MsCl (0.25 mL, 3.24 mmol). Stir at room temperature for 4 hours. Work up by adding sat. aq. NH$_4$Cl (20 mL), extract with CH$_2$Cl$_2$ (3×20 mL) and dry with MgSO$_4$. Column purification on silica gel using CH$_2$Cl$_2$ yielded intermediate 53 as an oil (0.76 g, 97%).

Mass spectrum: —CI m/z (assignment, relative intensity) 363 (MH$^+$, 1%), 267 (MH$^+$-MsOH, 100%), 249 (MH$^+$-MsOH—H$_2$O, 33%); EI: m/z (assignment, relative intensity) 362 ($M^+$, 5%), 266 ($M^+$-MsOH, 3%), 248 ($M^+$-MsOH—H$_2$O, 4%), 209 ($M^+$—CH$_2$CHOMsCH$_2$OH, 100%); High resolution EI Calculated C$_{19}$H$_{19}$FO$_4$S ($M^+$): 362.0988, Found: 362.0984 (12%).

b) (3S,4aR,13bR)-3-azido-12-fluoro-2,3,4,4a,9,13b-hexahydrodibenzo[3,4:6,7]-cyclohepta[1,2-b]pyran (Intermediate 54)

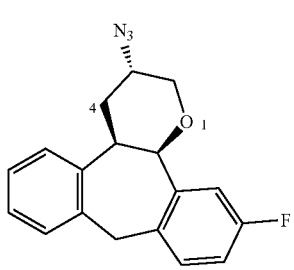

intermediate 54

Dissolve mesylate intermediate 53 (0.29 g, 0.79 mmol) in DMF (10 mL), add NaN$_3$ (0.10 g, 1.58 mmol) and heat the mixture at 90° C. for 2 hours. Add sat. aq. NH$_4$Cl (10 mL), extract with CH$_2$Cl$_2$ (3×10 mL) and dry with MgSO$_4$. Column purification on silica gel using CH$_2$Cl$_2$/heptane (40:60) yielded intermediate 54 as a crystalline product (0.22 g, 88%); mp: 91-93° C.

Mass spectrum: —CI m/z (assignment, relative intensity) 310 (MH$^+$, 13%), 282 (MH$^+$—N$_2$, 100%); EI: m/z (assignment, relative intensity) 281 ($M^+$—N$_2$, 28%), 208 (100%); High resolution EI Calculated C$_{18}$H$_{16}$FNO ($M^+$—N$_2$): 309.1216, Found: 309.1223 (40%).

c) (3S,4aR,13bR)-12-fluoro-2,3,4,4a,9,13b-hexahydrodibenzo[3,4:6,7]cyclohepta-[1,2-b]pyran-3-amine (Final Compound 30)

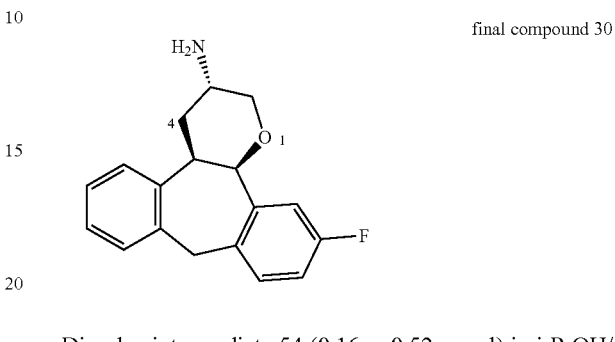

final compound 30

Dissolve intermediate 54 (0.16 g, 0.52 mmol) in i-PrOH/THF (2:1, 15 mL). Add 10% Pd—C (ca. 100 mg) and subject to hydrogenation (1 atmospheric pressure) for 1 night. Filter through a pad of celite, wash the solids with CH$_2$Cl$_2$ (5×10 mL) and evaporate the filtrate. The residue is purified by column chromatography on silica gel using CHCl$_3$/MeOH (75:25) to give final compound 30 as a crystalline product (0.14 g, 94%); mp: 74-76° C.

Mass spectrum: —CI m/z (assignment, relative intensity) 284 (MH$^+$, 100%); EI: m/z (assignment, relative intensity) 283 ($M^+$, 5%), 209 ($M^+$—CH$_2$CHNH$_2$CH$_2$OH, 100%); High resolution EI Calculated C$_{18}$H$_{18}$FNO ($M^+$): 283.1372, Found: 283.1370 (43%).

Example B31

(4aR,13bR)-12-fluoro-4,4a,9,13b-tetrahydrodibenzo[3,4:6,7]cyclohepta[1,2-b]-pyran-3(2H)-one (Final Compound 31)

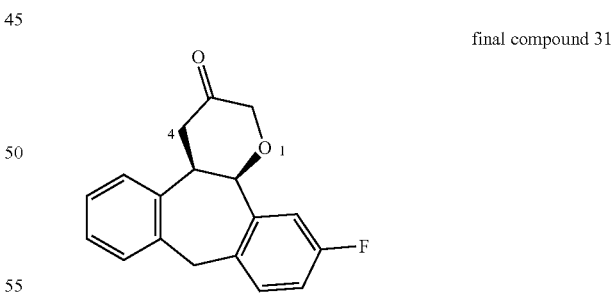

final compound 31

Dissolve final compound 29 (77 mg, 0.27 mmol) in CH$_2$Cl$_2$ (10 mL) and add pyridinium chlorochromate (131 mg, 0.54 mmol). Stir at room temperature for 20 hours. Filter through a pad of celite, wash the solids with CH$_2$Cl$_2$ (5×20 mL) and evaporate the filtrates. Column purification on silica gel using ether/hexane (50:50) yielded final compound 31 as a white crystalline product (61 mg, 80%); mp: 146-148° C.

Mass spectrum: —CI m/z (assignment, relative intensity) 283 (MH$^+$, 11%), 265 (MH$^+$—H$_2$O, 100%), 237 (MH$^+$—H$_2$O—CO, 22%); EI: m/z (assignment, relative intensity)

282 (M+·, 26%), 209 (M+·—CH$_2$COCH$_2$OH, 100%); High resolution EI Calculated C$_{18}$H$_{15}$FO$_2$ (M+·): 282.1056, Found: 282.1057 (40%).

Example B32

(3S,4aR,13bR)-12-fluoro-N,N-dimethyl-2,3,4,4a,9,13b-hexahydrodibenzo[3,4:6,7]-cyclohepta[1,2-b]pyran-3-amine (Final Compound 32)

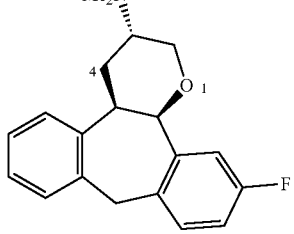

final compound 32

Intermediate 54 (0.24 g, 0.76 mmol) was dissolved in i-PrOH/THF (2:1, 15 mL). Add 10% Pd—C (ca. 150 mg) and subject the mixture to hydrogenation (1 atmospheric pressure) for 1 night. Add 35% aq. CH$_2$O (0.60 mL, 7.6 mmol) and continue hydrogenation for 2 days. Filter through celite and wash with CH$_2$Cl$_2$ (5×15 mL). Combine the organic phases and dry with MgSO$_4$. The solution was filtered and evaporated, and the residue was purified by column chromatography on silica gel using CHCl$_3$/MeOH (90:10) to yield final compound 32 MH-170 as an oil (0.22 g, 93%).

Mass spectrum: —CI m/z (assignment, relative intensity) 312 (MH+, 100%); EI: m/z (assignment, relative intensity) 311 (M+·, 7%).

Example B33

(3R,4aR,13bR)-12-fluoro-N-methyl-2,3,4,4a,9,13b-hexahydrodibenzo[3,4:6,7cyclohepta[1,2-b]pyran-3-amine (Final Compound 33)

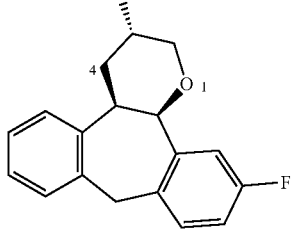

final compound 33

Dissolve final compound 31 (0.18 g, 0.63 mmol) in i-PrOH/THF (2:1, 10 mL). Add 10% Pd—C (ca. 100 mg), Et$_3$N (0.87 mL, 6.3 mmol) and MeNH$_2$.HCl (0.42 g, 6.3 mmol). Subject the mixture to hydrogenation (1 atmospheric pressure) for 1 night. Filter through a pad of celite and wash the solids with CH$_2$Cl$_2$ (5×15 mL). The solution was filtered and evaporated and the residue was purified by column chromatography on silica gel using CHCl$_3$/MeOH (90:10) to yield two diastereoisomers (0.18 g, 95%) with a ratio of 5:1, from which the major (3R)-isomer (final compound 33) can be partly separated.

Mass spectrum: —CI m/z (assignment, relative intensity) 298 (MH+, 100%); EI: m/z (assignment, relative intensity) 297 (M+, 5%), 266 (M+·—CH$_3$NH$_2$, 19%); High resolution EI Calculated C$_{19}$H$_{20}$FNO (M+·): 297.1529, Found: 297.1528 (3.5%).

Example B34

(4aR*,13bS*)-12-fluoro-4,4-a,9,13b-tetrahydrodibenzo[3,4:6,7]cyclohepta[1,2-b]pyran-3(2H)-one (Final Compound 34)

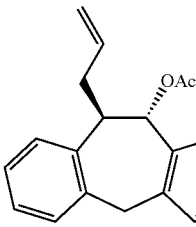

intermediate 56

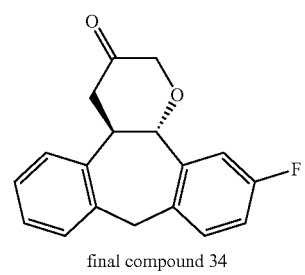

final compound 34 a) Conversion of alkene into diastereoisomeric diols. Dissolve intermediate 56 (1.40 g, 4.52 mmol) in acetone (30 mL). Add a small crystal of OsO$_4$ (catalytic amount) and N-methylmorpholine N-oxide (0.63 g, 5.42 mmol). Stir at room temperature for 1 day. The solvent was removed under reduced pressure, and the residue was purified by column chromatography on silica gel using EtOAc/hexane (80:20) to yield a mixture of two diastereoisomeric diols (oil, 1.45 g, 93%).

b) Selective mono-tosylation of primary alcohol group. Dissolve the above diols (1.45 g, 4.22 mmol) in toluene (50 mL). Add Et$_3$N (1.76 mL, 12.6 mmol), TsCl (1.05 g, 5.48 mmol) and Bu$_2$SnO (0.10 g, 0.42 mmol). Stir at room temperature for 1 day. Add sat. aq. NH$_4$Cl (30 mL), extract with CH$_2$Cl$_2$ (3×20 mL) and dry with MgSO$_4$. The solution was filtered and evaporated and the residue was purified by column chromatography using EtOAc/hexane (40:60) to yield the diastereoisomeric monotosylate derivatives corresponding to selective sulfonylation of the primary OH group (oil, 1.74 g, 83%).

c) Protection of secondary alcohol group. Dissolve the monotosylates (1.74 g, 3.49 mmol) in CH$_2$Cl$_2$ (60 mL) and add dihydropyran (1.59 mL, 17.5 mmol), camphorsulfonic acid (10 mg, 0.035 mmol). Stir at room temperature for 1 h and remove the solvent under reduced pressure.

d) Deprotection and cyclisation of benzylic alcohol. The residue was dissolved in MeOH (50 mL). Add K$_2$CO$_3$ (0.79 g, 6.99 mmol) and stir at room temperature for 1 night. Work up by adding sat. aq. NH$_4$Cl (30 mL), extract 3 times with CH$_2$Cl$_2$ (3×20 mL) and dry with MgSO$_4$. The solvent was evaporated and the residue containing the benzylic alcohol was dissolved in dry THF (50 mL). Add NaH (0.21 g, 6.99 mmol) and stir at room temperature for 3 days to effect cyclisation. Work it up by adding sat. aq NH$_4$Cl (30 mL) and extract with CH$_2$Cl$_2$ (3×20 mL). Dry with MgSO$_4$ and evaporate the solvent.

e) Deprotection and oxidation of secondary alcohol group. Dissolve the residue (1.70 g) in 20 mL MeOH/H$_2$O (9:1) and add Dowex 50WX8-100 (1.00 g). Heat the mixture at 50° C. for 2 hours. Filter through P3 filter, wash the solids with CH$_2$Cl$_2$ (5×15 mL) and evaporate. Column purification on silica gel using ether/hexane (70:30) yielded an oil (two diastereoisomeric alcohols) (0.87 g, 88%). Dissolve the above oil (0.87 g, 3.06 mmol) in CH$_2$Cl$_2$ (40 mL). Add pyridinium chlorochromate (1.32 g, 6.13 mmol) and stir at room temperature for 1 night. Filter through a pad of celite, wash the solids with CH$_2$Cl$_2$ (5×20 mL) and evaporate.

Column purification on silica gel using CH$_2$Cl$_2$/hexane (80:20) yielded final compound 34 as an oil (0.66 g, 76%).

Mass spectrum: —CI m/z (assignment, relative intensity) 283 (MH$^+$, 25%), 265 (MH$^+$—H$_2$O, 100%); EI: m/z (assignment, relative intensity) 282 (M$^+$·, 39%), 209 (M$^+$. —CH$_2$COCH$_2$OH, 100%).

Example B35

(3S*,4aR*,13bS*)-12-fluoro-N-methyl-2,3,4,4a,9, 13b-hexahydrodibenzo[3,4:6,7]-cyclohepta[1,2-b] pyran-3-amine (Final Compound 35)

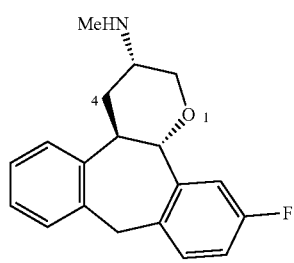

final compound 35

Dissolve final compound 34 (0.23 g, 0.83 mmol) in i-PrOH (15 mL). Add Et$_3$N (1.15 mL, 8.25 mmol), MeNH$_2$.HCl (0.56 g, 8.25 mmol) and 10% Pd/C (ca. 150 mg). Subject to hydrogenation (1 atmospheric pressure) for 1 night. Filter through a pad of celite and wash the solids with CH$_2$Cl$_2$ (5×10 mL). The solution was filtered and evaporated, and the residue was purified by column chromatography on silica gel using CHCl$_3$/MeOH (90:10) to yield final compound 35 as the nearly exclusive diastereoisomer (0.23 g, 95%).

Mass spectrum: —CI m/z (assignment, relative intensity) 298 (MH$^+$, 100%); EI: m/z (assignment, relative intensity) 209 (M$^+$. —CH$_2$CH(NHMe)CH$_2$OH, 100%).

Example B36 a) Methyl(2R,3aR,12bS)-2-(aminomethyl)-11-fluoro-3,3a,8,12b-tetrahydrodibenzo[3,4:6,7]-cyclohepta[1,2-b]pyrrole-1(2H)-carboxylate (Intermediate 62b), [(2R,3aR,12bS)-1-acetyl-11-fluoro-1,2,3,3a,8, 12b-hexahydrodibenzo[3,4:6,7]cyclohepta[1,2-b] pyrrol-2-yl]methanamine (Intermediate 62c), and (2R,3aR,12bS)-2-(aminomethyl)-11-fluoro-3,3a,8, 12b-tetrahydrodibenzo[3,4:6,7]cyclohepta-[1,2-b] pyrrole-1(2H)-carbaldehyde (Intermediate 62d)

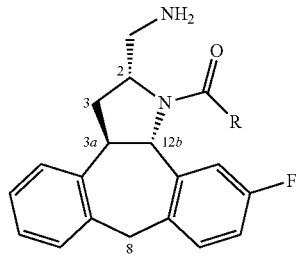

intermediate 62b R = OMe
intermediate 62c R = Me
intermediate 62d R = H

Representative Procedure—Synthesis of Methyl(2R,3aR, 12bS)-2-(Aminomethyl)-11-fluoro-3,3a,8,12b-tetrahydrodibenzo[3,4:6,7]cyclohepta[1,2-b]pyrrole-1(2H)-carboxylate (intermediate 62b): A solution of triphenylphosphine (996 mg, 3.8 mmol) in dry THF (20 mL) was placed in two-necked 100 mL flask, equipped with septum, argon inlet and magnetic stirrer; cooled down to −15° C. Neat diisopropyl azodicarboxylate (768 mg, 3.8 mmol) was added through a septum with intensive stirring. Resulting yellow suspension was stirred at above temperature for 30 minutes, then carbamate intermediate 62 (650 mg, 1.9 mmol) in THF (5 mL) was added in one portion. After 5 minutes of stirring, diphenylphosphoryl azide (606 mg, 2.2 mmol) in THF (3 mL) was added dropwise for 3 minutes, resulting turbid mixture allowed to warm up to room temperature and stirred then for 12 hours. After this time water (0.2 mL) and triphenylphosphine (996 mg, 3.8 mmol) was added, and solution stirred at 45° C. for 2 hours. After cooling down to room temperature, silica gel (Kieselgel 60, 70-230 mesh, 4 g) was added, THF removed in vacuo, and silica powder submitted to the flash chromatography (Kieselgel 60, 230-400 mesh, CH$_2$Cl$_2$-MeOH, 100/0, gradually to 85/15) to give desired amine intermediate 62b (401 mg, 1.18 mmol, 62%) as colorless oil, darkening on standing.

Intermediate 62b

HRMS Calcd. for C$_{20}$H$_{21}$FN$_2$O$_2$: 340.1587; Found: 340.1588.

Intermediate 62c: Two Rotamers Present (ca. 2:1 ratio)

CI-MS (CH$_4$) 325 (MH$^+$, 100%); 305 (MH$^+$—HF, 10%).

HRMS Calcd. for C$_{20}$H$_{21}$FN$_2$O: 324.1638; Found: 324.1644.

Intermediate 62d: Two Rotamers Present (ca. 5:2 ratio)

HRMS Calcd. for $C_{19}H_{19}FN_2O$: 310.1481; Found: 310.1480.

b) Methyl(2R,3aR,12bS)-2-[(dimethylamino)methyl]-11-fluoro-3,3a,8,12b-tetrahydro-dibenzo[3,4:6,7]cyclohepta[1,2-b]pyrrole-1(2H)-carboxylate (final compound 36a),

[(2R,3aR,12bS)-1-acetyl-11-fluoro-1,2,3,3a,8,12b-hexahydrodibenzo[3,4:6,7]-cyclohepta[1,2-b]pyrrol-2-yl]-N,N-dimethylmethanamine (Final Compound 36b) and (2R,3aR,12bS)-2-[(dimethylamino)methyl]-11-fluoro-3,3a,8,12b-tetrahydrodibenzo[3,4:6,7]cyclohepta[1,2-b]pyrrole-1(2H)-carbaldehyde (Final Compound 36c)

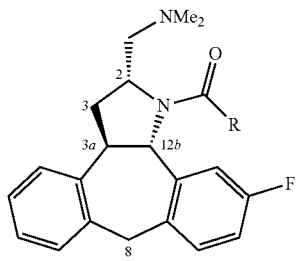

final compound 36a R = OMe
final compound 36b R = Me
final compound 36c R = H

Representative Procedure—Synthesis of Methyl(2R,3aR,12bS)-2-[(Dimethylamino)methyl]-11-fluoro-3,3a,12b-tetrahydrodibenzo[3,4:6,7]cyclohepta[1,2-b]pyrrole-1(2H)-carboxylate (Final Compound 36a)

Amine intermediate 62b (401 mg, 1.18 mmol) was dissolved in MeOH (30 mL), AcOH (1 mL) and 35% aqueous formaldehyde (1 g, 11.7 mmol) added, followed by sodium cyanoborohydride (628 mg, 10 mmol). The resulting mixture was stirred at room temperature for 4 hours, quenched with concentrated HCl (5 mL), treated with solid NaHCO₃ (8.4 g, 100 mmol), 1N sodium hydroxide (15 mL). The precipitated product was filtered off, washed with water (5×25 mL), dissolved in ethyl acetate, washed with brine (30 mL), dried ($K_2CO_3$), evaporated in vacuo and purified by column chromatography (Kieselgel 60, 230-400 mesh, $CH_2Cl_2$-MeOH 95/5 to 90/10 to 85/15) to give final compound 36a (313 mg, 0.85 mmol, 72%) as yellowish oil.

Final Compound 36a:

HRMS Calcd. for $C_{22}H_{25}FN_2O_2$: 368.1900; Found: 368.1895.

Final Compound 36b: Two Rotamers, Ca. 3:2 Ratio.

HRMS Calcd. for $C_{22}H_{25}FN_2O$: 352.1951; Found: 352.1955.

Final compound 36c: Two rotamers, ca. 5:3 ratio.

HRMS Calcd. for $C_{21}H_{23}FN_2O$ 338.1794; Found: 338.1790.

Example 37

[(2R,3aR,12bS)-11-fluoro-1,2,3,3a,8,12b-hexahydrodibenzo[3,4:6,7]cyclohepta-[1,2-b]pyr-rol-2-yl]N,N-dimethylmethanamine (Final Compound 37)

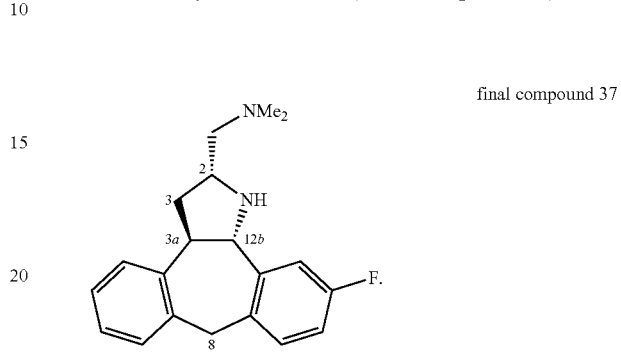

final compound 37

A mixture of final compound 36a (100 mg, 0.27 mmol), i-PrOH (10 mL), potassium hydroxide (560 mg, 10 mmol) and water (0.1 mL) was refluxed under nitrogen atmosphere for 12 hours (oil bath temperature 135° C.), then cooled to room temperature. After dilution with water (50 mL), extraction with EtOAc (3×40 mL), the combined organics were washed with water (3×40 mL), brine (40 mL), dried over $K_2CO_3$ and evaporated to give pure final compound 37 (84 mg, 100%) as yellowish semisolid, which was converted to the hydrochloride salt (Final Compound 37a).

HRMS Calcd. for $C_{20}H_{23}FN_2$: 310.1845; Found: 310.1851.

Example B38

(2R,3aR,12bS)-11-fluoro-2-[(methylamino)methyl]-3,3a,8,12b-tetrahydrodibenzo-[3,4:6,7]-cyclohepta[1,2-b]pyrrole-1(2H)-carbaldehyde (Final Compound 38)

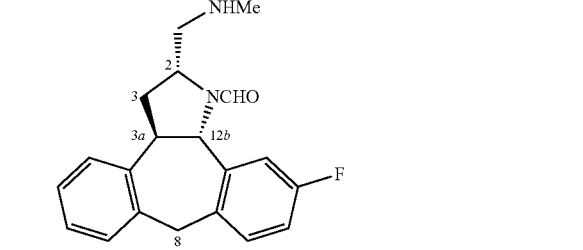

final compound 38

A mixture of aldehyde intermediate 63 (50 mg, 0.162 mmol), methylamine hydrochloride (218 mg, 3.24 mmol), Et₃N (405 mg, 4.0 mmol), 10% Pd—C (30 mg) and MeOH (12 mL) was hydrogenated for 2 hours at atmospheric pressure. The reaction mixture was filtered through Kieselguhr, which was subsequently washed with EtOAc (2×10 mL). The combined solutions were evaporated in vacuo and residue was purified by column chromatography (Kieselgel 60, 70-230 mesh, $CH_2Cl_2$/MeOH 100/0 to 85/15) to give final compound 38 (21 mg, 0.065 mmol, 40%) as brown oil; Four rotamers present (10:6:4:1 ratio).

CI-MS (CH$_4$): 325 (100%, M+H$^+$), 305 (12%, —HF). HRMS Calcd. for C$_{20}$H$_{21}$FN$_2$O: 324.1638; Found: 324.1650.

Example B39

2-((2R,3aR,12bS)-2-[(dimethylamino)methyl]-11-fluoro-3,3a,8,12b-tetrahydrodibenzo[3,4:6,7]cyclohepta[1,2-b]pyrrol-1(2H)-yl)ethanol (Final Compound 39)

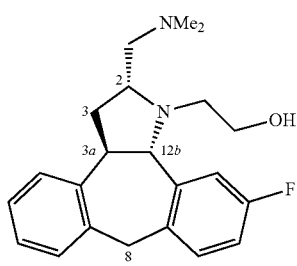

final compound 39

Hydroxyacetaldehyde dimer (2,5-dihydroxy-1,4-dioxane) (240 mg, 2.0 mmol) was dissolved in MeOH (25 mL) and stirred at 40° C. for 30 minutes, then amine compound 37 (124 mg, 0.40 mmol) was added and stirring at 40° C. continued for another 30 minutes. After cooling down to room temperature, AcOH (120 mg, 2.0 mmol) was added, followed by sodium cyanoborohydride (188 mg, 3.0 mmol) and the resulting mixture was stirred for 2 hours. After this time it was quenched with concentrated HCl (2 mL), treated with solid NaHCO$_3$ (2.94 g, 35 mmol), 1N sodium hydroxide (3 mL). About 20 mL of MeOH was removed in vacuo, the residue diluted with water (30 mL), and extracted with EtOAc (3×30 mL). The combined organics were washed with water (5×25 mL), brine (30 mL), dried (K$_2$CO$_3$), evaporated in vacuo and purified by column chromatography (Kieselgel 60, 230-400 mesh, CH$_2$Cl$_2$-MeOH 95/5 to 90/10 to 85/15) to give amine compound 39 (80 mg, 0.244 mmol, 61%) as colorless oil.

HRMS Calcd. for C$_{22}$H$_{27}$FN$_2$O: 354.2107; Found: 354.2107.

Example B40

[(2R,3aR,12bS)-11-Fluoro-1-(2-methoxyethyl)-1,2,3,3a,8,12b-hexahydrodibenzo-[3,4:6,7]-cyclohepta[1,2-b]pyrrol-2-yl]-N,N-dimethylmethanamine (Final Compound 40)

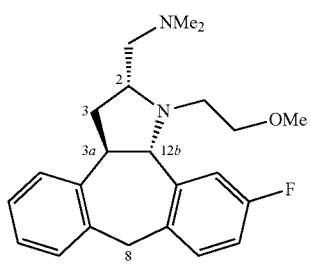

final compound 40

2-((2R,3aR,12bS)-2-[(Dimethylamino)methyl]-11-fluoro-3,3a,8,12b-tetrahydrodibenzo[3,4:6,7]cyclohepta[1,2-b]pyrrol-1(2H)-yl)ethanol compound 39 (50 mg, 0.153 mmol) was dissolved in dry THF (10 mL), then 60% NaH dispersion (8 mg, 0.2 mmol) was added, followed by dimethyl sulfate (25 mg, 0.2 mmol). The resulting mixture was stirred under argon atmosphere at 60° C. for 5 hours, then cooled, quenched with concentrated ammonium hydroxide (2 mL), diluted with water (40 mL). After extraction of product with EtOAc (3×25 mL) the combined organics were washed with water (3×25 mL), brine (25 mL), dried over K$_2$CO$_3$, evaporated in vacuo, and the residue purified by column chromatography (Kieselgel 60, 230-400 mesh, CH$_2$Cl$_2$-MeOH 95/5 to 90/10 to 85/15) to give final compound 40 (39 mg, 0.107 mmol, 70%) as yellowish oil.

HRMS Calcd. for C$_{23}$H$_{29}$FN$_2$O: 368.2264; Found: 368.2270.

Example B41

[(2R,3aR,12bS)-1-cyano-11-fluoro-1,2,3,3a,8,12b-hexahydrodibenzo[3,4:6,7]-cyclohepta[1,2-b]pyrrol-2-yl]-N,N-dimethylmethanamine (Final Compound 41)

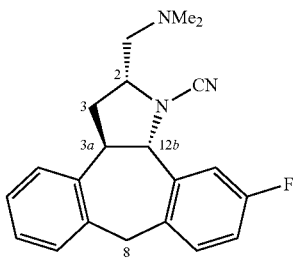

final compound 41

Poly(4-vinylpyridine) crosslinked with 2% divinylbenzene (0.5 g) was swollen for 1 hour with CH$_2$Cl$_2$ (10 mL), then final compound 37 (57 mg, 0.184 mmol) in CH$_2$Cl$_2$ (2 mL) was added in one portion, followed by cyanogen bromide (39 mg, 0.367 mmol), then suspension stirred at room temperature for 30 minutes. The resin was filtered off, filtrate treated with saturated aqueous K$_2$CO$_3$ (10 mL), organic phase was separated, evaporated in vacuo, and the residue purified by column chromatography (Kieselgel 60, 230-400 mesh, CH$_2$Cl$_2$-MeOH 95/5 to 90/10→87/13) to give final compound 41 (24 mg, 0.077 mmol, 42%) as brownish oil.

CI-MS (CH$_4$): 308 (100%, M+H$^+$), 288 (8%, —HF).

HRMS Calcd. for C$_{19}$H$_{18}$FN$_3$: 307.1485; Found: 307.1499.

Example B42

(2R,3aR,12bS)-11-fluoro-2-(4-morpholinylmethyl)-1,2,3,3a,8,12b-hexahydrodibenzo[3,4:6,7]cyclohepta[1,2-b]pyrrole (Final Compound 42)

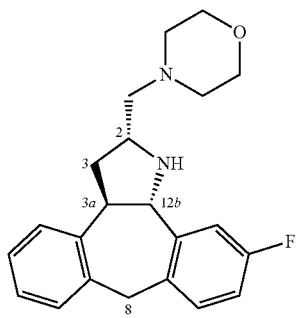

final compound 42

To a solution of the aziridine intermediate 64 (63 mg, 0.237 mmol) in acetonitrile (1 mL) was added sodium iodide (107 mg, 0.711 mmol) and trimethylsilyl chloride (90 μL, 0.711 mmol) at room temperature. After the solution was stirred for 2 hours, morpholine (44 mg, 0.5 mmol) in acetonitrile (0.5 mL) was added dropwise to the mixture. The solution was heated to the boiling point of the solvent for 2 hours. The dark brown reaction mixture was quenched with aqueous 1.2N HCl solution and then was treated with sat. NaHCO$_3$. The organic layer was separated and the aqueous layer was extracted with methylene chloride (3×10 mL). The combined organic extracts were washed with 20 mL of brine, dried over anhydrous MgSO$_4$, filtered and concentrated in vacuo. The residue was purified by column chromatography on basic alumina (Brockmann III, EtOAc-MeOH, 100/0 to 98/2 to 95/5) gave final compound 42 (38 mg, 0.11 mmol, 45%) as brownish oil.

CI-MS (CH$_4$): 353 (100%, M+H$^+$); 333 (—HF, 7%).
HRMS Calcd. for C$_{22}$H$_{25}$FN$_2$O: 352.1951; Found: 352.1966.

Example B43

2-(4-{[(2R,3aR,12bS)-11-fluoro-1,2,3,3a,8,12b-hexahydrodibenzo[3,4:6,7]-cyclohepta[1,2-b]pyrrol-2-yl]methyl}-1-piperazinyl)ethanol (Final Compound 43a) and 2-[{[(2R,3aR,12bS)-11-fluoro-1,2,3,3a,8,12b-hexahydrodibenzo[3,4:6,7]cyclohepta[1,2-b]pyrrol-2-yl]methyl}(methyl)amino]-pethanol (Final Compound 43b)

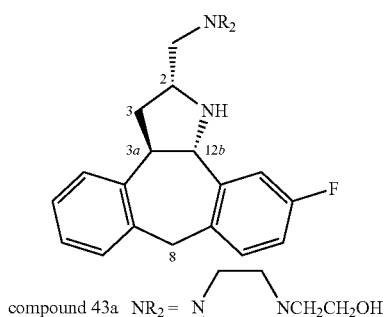

compound 43a NR$_2$ = N⌐NCH$_2$CH$_2$OH compound 43b NR$_2$ = N(Me)CH$_2$CH$_2$OH A mixture of appropriate nosylamide intermediate 66a or 66b (ca 0.4 mmol), thiophenol (110 mg, 1.0 mmol), anhydrous K$_2$CO$_3$ (138 mg, 1 mmol) and DMF (20 mL) was stirred at 80° C. for 4 hours, cooled to ambient temperature, diluted with water, product extracted with EtOAc (3×50 mL), combined organics washed with water (4×50 mL), brine (35 mL), dried (K$_2$CO$_3$), evaporated and purified by solid phase extraction on basic alumina (Brockmann II, heptane-ethyl acetate 50/50, then EtOAc-MeOH 100/0 to 96/4 to 90/10) to give compound 43a (111 mg, 0.28 mmol, 52% from intermediate 65) or compound 43b (80 mg, 0.24 mmol, 44% from intermediate 65), both as brownish oils.

Compound 43a (TK-895):
HRMS: Calcd. for C$_{24}$H$_{30}$FN$_3$O: 395.2373; Found: 395.2374.

Compound 43b (TK-1013):
HRMS Calcd. for C$_{11}$H$_{25}$FN$_2$O: 340.1951; 340.1943.

Example B44

[(2R,4aR,13bS)-12-fluoro-2,3,4,4a,9,13b-hexahydro-1H-dibenzo[3,4:6,7]cyclohepta[1,2-b]pyridin-2-yl]-N,N-dimethylmethanamine (Compound 44)

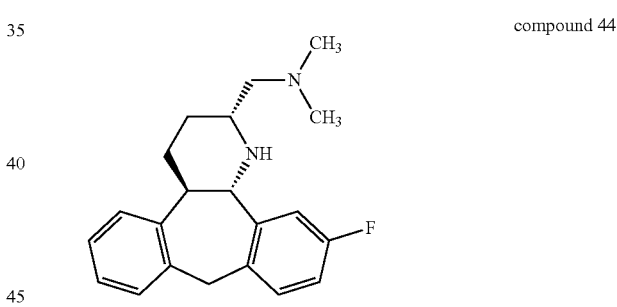

compound 44

Tosylate intermediate 67k (153 mg, 0.338 mmol), 40% aqueous methylamine (15 mL), and THF (35 mL) were heated in stainless-steel bomb at 135° C. for 15 hours. After cooling, the bomb was opened, THF and methylamine evaporated in vacuo, residue extracted with CH$_2$Cl$_2$ (4×20 mL). The combined organics were washed with water (3×20 mL), dried (K$_2$CO$_3$), evaporated and purified by column chromatography (Kieselgel 60, 230-400 mesh, CH$_2$Cl$_2$-MeOH 98/2 to 85/15) to afford final compound 44 (32 mg, 0.098 mmol, 29%) as a brown oil, which was converted to the oxalate salt (final compound 44a).

HRMS Calcd. for C$_{11}$H$_{25}$FN$_2$: 324.2002; Found: 324.1995.

Example B45

Methyl(2R,4aR,13bS)-2-[(dimethylamino)methyl]-12-fluoro-2,3,4,4a,9,13b-hexahydro-1H-dibenzo[3,4:6,7]cyclohepta[1,2-b]pyridine-1-carboxylate (Final Compound 45)

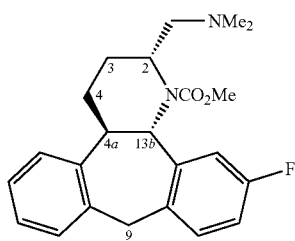

final compound 45

Conversion of final compound 44 (48 mg, 0.15 mmol) with methyl chloroformate was carried out in the same way as described for the preparation of intermediate 62 Column chromatography (Kieselgel 60, 70-230 mesh, MeOH—$CH_2Cl_2$ 3/97 to 15/85) afforded final compound 45 (45 mg, 0.118 mmol, 79%) as colorless oil.

HRMS Calcd. for $C_{23}H_{27}FN_2O_2$: 382.2057; Found: 382.2064.

Example B46

[(2R,4aR,13bS)-12-fluoro-2,3,4,4a,9,13b-hexahydrodibenzo[3,4:6,7]cyclohepta-[1,2-b]pyran-2-yl]-N-methylmethanamine (Final Compound 46)

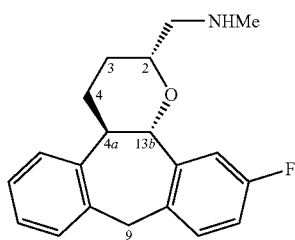

final compound 46

Tosylate intermediate 68e (282 mg, 0.62 mmol), 40% aqueous methylamine (25 mL), and THF (35 mL) were heated in a steel bomb at 135° C. for 15 hours. After cooling, bomb was opened, THF and methylamine evaporated in vacuo. The residue was extracted with $CH_2Cl_2$ (4×30 mL) and the combined organics were washed with water (3×20 mL), dried ($K_2CO_3$) and evaporated. Crystallization from $CH_2Cl_2$/hexane gave final compound 46 (70 mg, 0.225 mmol, 36%) as beige powder.

HRMS Calcd. for $C_{20}H_{22}FNO$: 311.1685; Found: 311.1700.

Example B47

[(3aR,12bS)-11-fluoro-3,3a,8,12b-tetrahydro-2H-dibenzo[3,4:6,7]cyclohepta[1,2-b]furan-3-yl]-N,N-dimethylmethanamine (Final Compound 47)

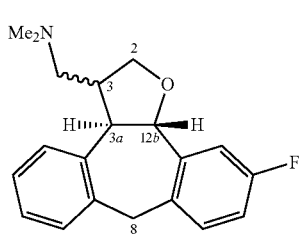

final compound 47

Azide intermediate 69i (122 mg, 0.39 mmol) was dissolved in MeOH (10 mL), 10% palladium on carbon (40 mg) was added and the mixture submitted to the hydrogenation under atmospheric pressure for 1.5 hour, then 35% aqueous formaldehyde (1 g) and AcOH (120 mg, 2 mmol) were added, and hydrogenation continued for 2 hours. After filtration through short pad of Celite, and addition of EtOAc (45 mL), the reaction mixture was washed with saturated aqueous sodium bicarbonate (25 mL), water (2×50 mL), brine (30 mL), dried over $K_2CO_3$ and evaporated in vacuo. The residue was purified by column chromatography (Kieselgel 60, 70-230 mesh, ethyl acetate-MeOH, 100/0 to 95/5 to 92/8 to 87/13) to afford final compound 47 (77 mg, 0.248 mmol, 63%) as yellow oil. Product is a mixture of 2 epimers (12.8:1 ratio).

HRMS Calcd. for $C_{20}H_{22}FNO$: 311.1685; Found: 311.1680.

CI-MS ($CH_4$) 312 ($MH^+$, 100%); 292 ($MH^+$—HF, 9%).

Example B48

[(3aR,12bR)-11-fluoro-3,3a,8,12b-tetrahydro-2H-dibenzo[3,4:6,7]cyclohepta[1,2-b]furan-3-yl]-N,N-dimethylmethanamine (Final Compound 48)

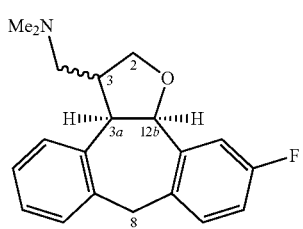

final compound 48

Reaction of intermediate 70d (100 mg, 0.304 mmol) was carried out was carried out in the same way as described for final compound 47. Purification by solid phase extraction (Alltech $C_{18}$ 2 g cartridge, water-MeOH, 100/0 to 50/50 to 0/100) furnished compound 48 (57 mg, 0.18 mmol, 59%). Product is a mixture of 2 epimers (2:1 ratio).

HRMS Calcd. for $C_{20}H_{22}FNO$: 311.1685; Found: 311.1692.

CI-MS ($CH_4$) 312 ($MH^+$, 100%); 292 ($MH^+$—HF, 12%).

Example B49

[(3aR,12bS)-11-fluoro-1,2,3,3a,8,12b-hexahydrodibenzo[3,4:6,7]cyclohepta[1,2-b]pyrrol-3-yl]-N,N-dimethylmethanamine (Final Compound 49)

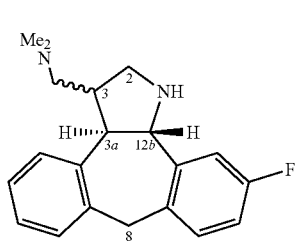

final compound 49

A mixture of intermediate 71f (194 mg, 0.53 mmol) and 10% palladium on carbon (50 mg) in MeOH (35 mL) was hydrogenated at atmospheric pressure for 40 minutes, then 35% aqueous formaldehyde (1 mL) was added and hydrogenation continued for another 40 minutes. After filtration through short pad of Celite, reaction mixture was evaporated in vacuo. The residue was dissolved i-PrOH (20 mL), KOH (560 mg, 10 mmol) and water (0.1 mL) were added and resulting solution was refluxed under nitrogen atmosphere for 12 hours (oil bath temperature 135° C.), then cooled to room temperature. After dilution with water (50 mL), extraction with EtOAc (3×40 mL), the combined organics were washed with water (3×40 mL), brine (40 mL), dried over $K_2CO_3$ and evaporated in vacuo. The residue was purified by column chromatography (basic alumina, Brockmann activity I, ethyl acetate-MeOH, 100/0 to 85/15) to give purefinal compound 49 (102 mg, 0.33 mmol, 62%) as brown oil. Product is a mixture of 2 epimers (1:1 ratio)

HRMS Calcd. for $C_{20}H_{23}FN_2$: 310.1845; Found: 310.1833.

Tables 1-3 list compounds of Formula (I), which were prepared according to one of the above examples.

TABLE 1

| Co. No. | Ex. No. | X | Y | ---$R^a$ | ---$R^b$ | Stereochemical/ salt data |
|---|---|---|---|---|---|---|
| 17 | B17 | —O— | NH | ----H | CH₂N(CH₃)₂ | 2R,3aR,12bS |
| 18 | B18 | —O— | NH | ----H | N(CH₃)(CH₂CH₂OH) | 2R,3aR,12bS |
| 19 | B19 | —O— | NH | ----H | piperazinyl-CH₂CH₂OH | 2R,3aR,12bS |
| 20 | B20 | —O— | NH | ----H | 3-hydroxypyrrolidinyl | 2R,3aR,12bS |
| 2 | B2 | —CH₂— | NH | ----H | CH₂N(CH₃)₂ | 2S,3aR,12bS |
| 37 | B37 | —CH₂— | NH | ----H | CH₂N(CH₃)₂ | 2R,3aR,12bS |
| 37a | B37 | —CH₂— | NH | ----H | CH₂N(CH₃)₂ | •HCl 2R,3aR,12bS |

TABLE 1-continued

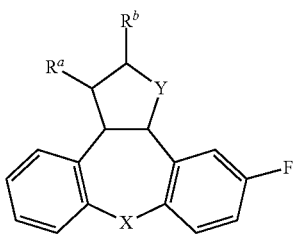

| Co. No. | Ex. No. | X | Y | ---R$^a$ | ---R$^b$ | Stereochemical/ salt data |
|---|---|---|---|---|---|---|
| 11 | B11 | —CH$_2$— | \NH | ----H | \N(CH$_2$)—C(=O)—O—CH$_3$, H | 2R,3aR,12bS |
| 43b | B43 | —CH$_2$— | \NH | ----H | \N(CH$_3$)—CH$_2$—CH$_2$—OH | 2R,3aR,12bS |
| 42 | B42 | —CH$_2$— | \NH | ----H | morpholinyl-CH$_2$— | 2R,3aR,12bS |
| 43a | B43 | —CH$_2$— | \NH | ----H | piperazinyl-CH$_2$-CH$_2$-OH | 2R,3aR,12bS |
| 5 | B5 | —CH$_2$— | \N—CH$_3$ | ----H | —N(CH$_3$)$_2$ | 2R,3aR,12bS |
| 39 | B39 | —CH$_2$— | \N—CH$_2$—CH$_2$—OH | ----H | —N(CH$_3$)$_2$ | 2R,3aR,12bS |
| 40 | B40 | —CH$_2$— | \N—CH$_2$—CH$_2$—O—CH$_3$ | ----H | —N(CH$_3$)$_2$ | 2R,3aR,12bS |
| 36c | B36c | —CH$_2$— | \N—CH=O | ----H | —N(CH$_3$)$_2$ | (2R,3aR,12bS |
| 38 | B38 | —CH$_2$— | \N—CH=O | ----H | —NH(CH$_3$) | 2R,3aR,12bS |
| 41 | B41 | —CH$_2$— | \N—C≡N | ----H | —N(CH$_3$)$_2$ | 2R,3aR,12bS |
| 36b | B36 | —CH$_2$— | \N—C(=O)—CH$_3$ | ----H | —N(CH$_3$)$_2$ | 2R,3aR,12bS |
| 10 | B10 | —CH$_2$— | \N—C(=O)—CH$_2$—O—CH$_3$ | ----H | —N(CH$_3$)$_2$ | 2R,3aR,12bS |

TABLE 1-continued
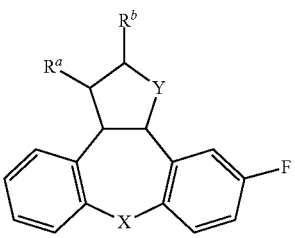
| Co. No. | Ex. No. | X | Y | ---R$^a$ | ---R$^b$ | Stereochemical/ salt data |
|---|---|---|---|---|---|---|
| 36a | B36 | —CH$_2$— | 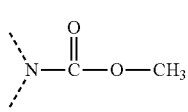 | ----H | 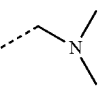 | 2R,3aR,12bS |
| 21 | B21 | —CH$_2$— |  | ----H | 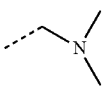 | 2S,3aR,12bS |
| 23 | B23 | —CH$_2$— |  | ----H | 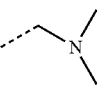 | 2R,3aR,12bS |
| 25 | B25 | —CH$_2$— |  | ----H | 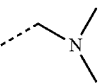 | 2S,3aR,12bS |
| 26 | B26 | —CH$_2$— |  | ----H | 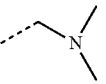 | 2S,3aR,12bS |
| 27 | B27 | —CH$_2$— |  | ----H | 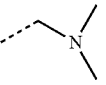 | 2R,3aR,12bS |
| 28 | B28 | —CH$_2$— |  | ----H | 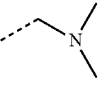 | 2R,3aR,12bS |
| 22 | B22 | —CH$_2$— |  | ----H | 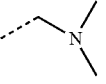 | 2S,3aR,12bS |
| 24 | B24 | —CH$_2$— |  | ----H | 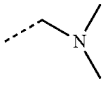 | 2R,3aR,12bS |
| 49 | B49 | —CH$_2$ |  | 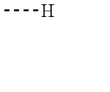 | ----H | 3aR,12bS |

TABLE 2

| Co. No. | Ex. No. | D | Stereochemical/salt data |
|---|---|---|---|
| 1 | B1 | CH₂–N(CH₃)–CH₂ (ring) | 4aS,13bR,14aS |
| 6 | B6 | CH₂–NH–C(=O) | 4aS,13bR,14aR |
| 15 | B15 | CH₂–NH–C(=O) | 4aS,13bR,14aS |
| 7 | B7 | CH₂–N(CH₃)–C(=O) | 4aS,13bR,14aR |
| 16 | B16 | CH₂–N(CH₃)–C(=O) | 4aS,13bR,14aS |
| 8 | B8 | CH₂–NH–C(=S) | 4aS,13bR,14aR |
| 3 | B3 | CH₂–NH–C(=S) | 4aS,13bR,14aS |
| 9 | B9 | CH₂–N=C(–S–CH₃) | 4aS,13bR,14aR |
| 4 | B4 | H₂C–N(CH₃)–CH₂–C(=O) | 5aS,14bR,15aS |

TABLE 2-continued

| Co. No. | Ex. No. | D | Stereochemical/salt data |
|---|---|---|---|
| 13 | B13 | H₂C–N(CH₃)–CH₂–C(=O) | 5aS,14bR,15aR |
| 12 | B12 | H₂C–N(H)–CH₂–C(=O) | 5aS,14bR,15aR |
| 14 | B14 | H₂C–N(CH₃)–CH₂–CH₂ | 5aS,14bR,15aR |
| 14a | B14 | H₂C–N(CH₃)–CH₂–CH₂ | Oxalate (1:1) 5aS,14bR,15aR |

TABLE 3
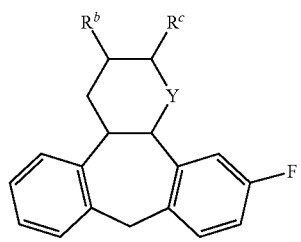
| Co. No. | Ex. No. | ---Y--- | ---R$^b$ | ---R$^c$ | Stereochemical/salt data |
|---|---|---|---|---|---|
| 29 | B29 | O | ----OH | ----H | 3R,4aR,13bR |
| 31 | B31 | O | =O | ----H | 4aR,13bR |
| 34 | B34 | O | =O | ----H | 4aR*,13bS* |
| 30 | B30 | O | ----NH$_2$ | ----H | 3S,4aR,13bR |
| 33 | B33 | O | ----NH—CH$_3$ | ----H | 3R,4aR,13bR |
| 35 | B35 | O | ----NH—CH$_3$ | ----H | 3S*,4aR*,13bS*- |
| 32 | B32 | O | ----CH$_2$N(CH$_3$)$_2$ | ----H | 3S,4aR,13bR |
| 46 | B46 | O | ----H | ----CH$_2$N(CH$_3$)$_2$ | 2R,4aR,13bS |
| 44 | B44 | NH | ----H | ----CH$_2$N(CH$_3$)$_2$ | 2R,4aR,13bS |
| 44a | B44 | NH | ----H | ----CH$_2$N(CH$_3$)$_2$ | oxalate (1:2) 2R,4aR,13bS |
| 45 | B45 | N—C(=O)—O—CH$_3$ | ----H | ----CH$_2$N(CH$_3$)$_2$ | 2R,4aR,13bS |

C. Pharmacological Examples

Example C.1

In Vitro Binding Affinity for 5-HT$_{2A}$ and 5-HT$_{2C}$ Receptors

The interaction of the compounds of Formula (I) with 5-HT$_{2A}$ and 5-HT$_{2C}$ receptors was assessed in in vitro radioligand binding experiments. In general, a low concentration of a radioligand with a high binding affinity for the receptor is incubated with a sample of a tissue preparation enriched in a particular receptor (1 to 5 mg tissue) in a buffered medium (0.2 to 5 ml). During the incubation, the radioligands bind to the receptor. When equilibrium of binding is reached, the receptor bound radioactivity is separated from the non-bound radioactivity, and the receptor bound activity is counted. The interaction of the test compounds with the receptors is assessed in competition binding experiments. Various concentrations of the test compound are added to the incubation mixture containing the tissue preparation and the radioligand. Binding of the radioligand will be inhibited by the test compound in proportion to its binding affinity and its concentration. The affinities of the compounds for the 5-HT$_2$ receptors were measured by means of radioligand binding studies conducted with: (a) human cloned 5-HT$_{2A}$ receptor, expressed in L929 cells using [$^{125}$I]R91150 as radioligand and (b) human cloned 5-HT$_{2C}$ receptor, expressed in CHO cells using [$^3$H] mesulergine as radioligand.

Example C.2

In Vitro Determination of NET Reuptake Inhibition

Cortex from rat brain was collected and homogenised using an Ultra-Turrax T25 and a Dual homogeniser in ice-cold homogenising buffer containing Tris, NaCl and KCl (50 mM, 120 mM and 5 mM, respectively, pH 7.4) prior to dilution to an appropriate protein concentration optimised for specific and non-specific binding. Binding was performed with radioligand [$^3$H]Nixosetine (NEN, NET-1084, specific activity ~70 Ci/mmol) diluted in ice cold assay buffer containing Tris, NaCl and KCl (50 mM, 300 mM and 5 mM, respectively, pH 7.4). at a concentration of 20 nmol/L. Prepared radioligand (50 µl) was then incubated (60 min, 25° C.) with membrane preparations pre-diluted to an appropriate protein concentration (4000, and with 50 µl of either the 10% DMSO control, Mazindol (10$^{-6}$ mol/L final concentration), or compound of interest. Membrane-bound activity was detected by filtration through a Packard Filtermate harvester onto GF/B Unifilterplates, washed with ice-cold Tris-HCl buffer, containing NaCl and KCl (50 mM, 120 mM and 4 mM; pH 7.4; 6×0.5 ml). Filters were allowed to dry for 24 h before adding scintillation fluid. Scintillation fluid was allowed to saturate filters for 24 h before counting in a Topcount scintillation counter. Percentage specific bound and competition binding curves were calculated using S-Plus software (Insightful).

Example C.3

In Vitro Binding Affinity for Human D2$_L$ Receptor

Frozen membranes of human Dopamine D2$_L$ receptor-transfected CHO cells were thawed, briefly homogenised using an Ultra-Turrax T25 homogeniser and diluted in Tris-HCl assay buffer containing NaCl, CaCl$_2$, MgCl$_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 µl), along with 50 µl of either the 10% DMSO control, Butaclamol (10$^{-6}$ mol/l final concentration), or compound of interest, was then incubated (30 min, 37° C.) with 400 µl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful).

TABLE 4

Pharmacological data.

| Co.No. | h-5HT$_{2A}$ | h-5HT$_{2C}$ | h-D2L | NET Reuptake Inhibition |
|---|---|---|---|---|
| 17 | 6.24 | 6.30 | 5.63 | 8.13 |
| 37a | 7.35 | 7.30 | 6.45 | 8.10 |
| 47 | 5.42 | 5.80 | n.d. | 7.96 |
| 43b | 7.17 | 7.05 | 6.36 | 7.80 |
| 32 | 6.17 | 6.88 | <6 | 7.71 |
| 23 | 6.18 | 6.64 | 5.30 | 7.55 |
| 1 | 6.94 | 6.82 | 5.65 | 6.94 |
| 39 | 7.06 | 7.33 | <6 | 6.90 |
| 28 | 5.11 | 5.75 | n.d. | 6.84 |
| 48 | 5.21 | 5.52 | n.d. | 6.65 |
| 36c | 6.26 | 7.11 | 5.31 | 6.65 |
| 5 | 7.56 | 8.27 | 6.88 | 6.54 |
| 30 | 6.57 | 6.84 | <6 | 6.52 |
| 46 | 7.86 | 8.23 | 5.20 | 6.40 |
| 20 | n.d. | 6.96 | 6.45 | 6.38 |
| 40 | 6.43 | 6.58 | <6 | 6.32 |
| 38 | 6.20 | 6.73 | 5.15 | 6.31 |
| 36a | <6 | <6 | <6 | 6.16 |
| 45 | n.d. | 5.65 | <5 | 6.10 |
| 7 | <6 | <6 | <6 | 6.05 |
| 8 | 7.07 | 6.60 | <5 | 5.66 |
| 15 | 5.08 | 5.63 | <5 | 5.62 |
| 25 | <5 | 5.65 | n.d. | 5.54 |
| 14a | 8.90 | 9.05 | 8.81 | 5.50 |
| 12 | n.d. | 7.23 | 6.08 | 5.46 |
| 36b | <6 | <6 | <6 | 5.41 |
| 9 | <6 | <6 | <6 | 5.40 |
| 22 | 5.07 | 5.87 | n.d. | 5.32 |
| 10 | 6.16 | 6.37 | <6 | 5.32 |
| 42 | 6.20 | 6.26 | n.d. | 5.26 |
| 3 | <6 | 6.62 | <6 | 5.24 |
| 13 | 7.06 | 6.92 | 6.37 | <5 |
| 35 | <6 | 5.58 | <6 | <6 |
| 43a | 6.37 | 6.39 | n.d. | <5 |
| 26 | <5 | <5 | <5 | <5 |
| 19 | n.d. | 5.37 | 6.95 | <5 |
| 16 | <5 | <5 | <5 | <5 |
| 4 | <6 | <6 | <6 | <5 | n.d. = not determined

D. Composition Examples

"Active ingredient" (A.I.) as used throughout these examples relates to a compound of Formula (I), a pharmaceutically acceptable acid addition salt, a stereochemically isomeric form thereof or a N-oxide form thereof.

Example D.1

Oral Solution

Methyl 4-hydroxybenzoate (9 g) and propyl 4-hydroxybenzoate (1 g) were dissolved in boiling purified water (41). In 31 of this solution were dissolved first 2,3-dihydroxybutanedioic acid (10 g) and thereafter A.I (20 g). The latter solution was combined with the remaining part of the former solution and 1,2,3-propanetriol (121) and sorbitol 70% solution (31) were added thereto. Sodium saccharin (40 g) were dissolved in water (500 ml) and raspberry (2 ml) and gooseberry essence (2 ml) were added. The latter solution was combined with the former, water was added q.s. to a volume of 201 providing an oral solution comprising 5 mg of the active ingredient per teaspoonful (5 ml). The resulting solution was filled in suitable containers.

Example D.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in dichloromethane (150 ml). Then there were added dichloromethane (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

Example D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and A.I. (4 g). The solution was cooled to room temperature and supplemented with water for injection q.s. ad 1000 ml, giving a solution comprising 4 mg/ml of A.I. The solution was sterilized by filtration and filled in sterile containers.

The invention claimed is:

1. A compound according to Formula (I)

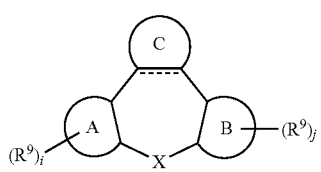

(I)

an N-oxide form, a pharmaceutically acceptable addition salt or a stereochemically isomeric form thereof, wherein:

the dotted line represents an optional bond;

i and j are integers, independently from each other, equal to zero, 1, 2, 3 or 4;

A and B are, each independently from each other, benzo, naphtho or a radical selected from the group of furo; thieno; pyrrolo; oxazolo; thiazolo; imidazolo; isoxazolo; isothiazolo; oxadiazolo; triazolo; pyridino; pyridazino; pyrimidino; pyrazino; indolo; indolizino; isoindolo; benzofuro; isobenzofuro; benzothieno; indazolo; benzimidazolo; benzthiazolo; quinolizino; quinolino; isoquinolino; phthalazino; quinazolino; quinoxalino; chromeno and naphthyridino;

each $R^9$ is, independently from each other, selected from the group of hydrogen; halo; cyano; hydroxy; carboxyl; nitro; amino; mono- or di(alkyl)amino; alkylcarbonylamino; aminosulfonyl; mono- or di(alkyl)aminosulfonyl; alkyl; alkyloxy; alkylcarbonyl and alkyloxycarbonyl;

X represents O, S(=O) or S(=O)$_2$; wherein:

C is a group of formula (c-1), (c-2), (c-3) or (c-4);

(c-1)

(c-2)

(c-3)

(c-4)

wherein:

$Y^1$ is S; S(=O); S(=O)$_2$ or $NR^{10}$; wherein $R^{10}$ is selected from the group of hydrogen, cyano, alkyl, alkyloxyalkyl, formyl, alkylcarbonyl, alkyloxycarbonyl, alkyloxyalkylcarbonyl, arylcarbonyl, arylalkyl, arylalkylcarbonyl, alkylsulfonyl, arylsulfonyl and arylalkylsulfonyl;

$Y^2$ is $Y^1$ or O;

$R^{10}$ and $R^{11}$ may form together a bivalent radical (e-1), (e-2) or (e-3);

—CH$_2$—NH—CH$_2$— (e-1)

—CH$_2$—NH—CH$_2$—CH$_2$— (e-2)

—CH$_2$CH$_2$—NH—CH$_2$— (e-3)

each bivalent radical (e-1), (e-2) and (e-3) optionally substituted by one or more substituents selected from oxo, thioxo, alkyl and alkylthio;

$R^{12}$ is hydrogen or alkyl;

$R^{13}$ is hydrogen or alkyl;

$R^{14}$ is hydrogen, hydroxy, oxo or a group of formula (d-1)

$R^{11}$ is a group of formula (d-1);

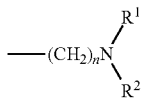
(d-1)

wherein:

n is zero, 1, 2, 3, 4, 5 or 6;

$R^1$ and $R^2$ each independently are hydrogen; alkyl; alkylcarbonyl; alkyloxyalkyl; alkylcarbonyloxyalkyl; alkyloxycarbonylalkyl; arylalkyl; arylcarbonyl; alkyloxycarbonyl; aryloxycarbonyl; arylalkylcarbonyl; alkyloxycarbonylalkylcarbonyl; mono- or di(alkyl)aminocarbonyl; mono- or di(aryl)aminocarbonyl; mono- or di(arylalkyl)aminocarbonyl; mono- or di(alkyloxycarbonylalkyl)aminocarbonyl; alkylsulphonyl; arylsulphonyl; arylalkylsulphonyl; mono- or di(alkyl)amino-thiocarbonyl; mono- or di(aryl)aminothiocarbonyl; mono -or di(arylalkyl)aminothiocarbonyl; mono-, di- or tri(alkyl)amidino; mono-, di- or tri(aryl)amidino and mono-, di- or tri(arylalkyl)amidino; or $R^1$ and $R^2$ taken together with the nitrogen atom to which they are attached form a radical of formula (a-1), (a-2), (a-3), (a-4), (a-5) or (a-6);

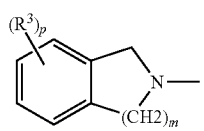
(a-1)

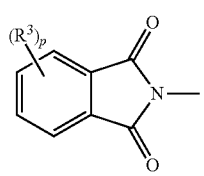
(a-2)

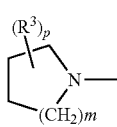
(a-3)

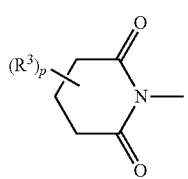
(a-4)

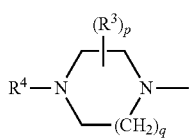
(a-5)

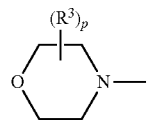
(a-6)

wherein:

P is zero, 1, 2, 3 or 4;

q is 1 or 2;

m is zero, 1, 2, or 3;

each $R^3$ independently is selected from the group of hydrogen; halo; hydroxy; cyano; alkyl; alkyloxyalkyl; aryloxyalkyl; mono- or di(alkyl)aminoalkyl; hydroxycarbonylalkyl; alkyloxycarbonylalkyl; mono- or di(alkyl)aminocarbonylalkyl; mono- or di(aryl)aminocarbonylalkyl; mono- or di(alkyl)aminocarbonyloxyalkyl; alkyloxycarbonyloxyalkyl; arylaminocarbonyloxyalkyl; arylalkylaminocarbonyloxyalkyl; aryl; alkyloxy; aryloxy; alkylcarbonyloxy; arylcarbonyloxy; arylalkylcarbonyloxy; alkylcarbonyl; arylcarbonyl; aryloxycarbonyl; hydroxycarbonyl; alkyloxycarbonyl; alkylcarbonylamino; arylalkylcarbonylamino; arylcarbonylamino; alkyloxycarbonylamino; amino-carbonylamino; mono- or di(arylalkyl)aminocarbonylamino; alkylsulphonylalkylaminocarbonylamino; or two $R^3$-radicals may form together a bivalent radical —$CR^5R^5$—$CR^5R^5$—O— (b-1)

—O—$CR^5R^5$—$CR^5R^5$— (b-2)

—O—$CR^5R^5$—$CR^5R^5$—O— (b-3)

—O—$CR^5R^5$—$CR^5R^5$—$CR^5R^5$— (b-4)

—$CR^5R^5$—$CR^5R^5$—$CR^5R^5$—O— (b-5)

—O—$CR^5R^5$—$CR^5R^5$—$CR^5R^5$—O— (b-6)

—O—$CR^5R^5$—$CR^5R^5$—$CR^5R^5$—$CR^5R^5$— (b-7)

—$CR^5R^5$—$CR^5R^5$—$CR^5R^5$—$CR^5R^5$—O— (b-8)

—O—$CR^5R^5$—$CR^5R^5$—$CR^5R^5$—O— (b-9)

wherein $R^5$ is selected from the group of hydrogen, halo, hydroxy, alkyloxy and alkyl;

$R^4$ is selected from the group of hydrogen; alkyl; arylalkyl; alkyloxyalkyl; alkylcarbonyloxyalkyl; alkyloxycarbonylalkyl; arylcarbonylalkyl; alkylsulphonyloxyalkyl; aryloxyaryl; alkyloxycarbonylaryl; alkylcarbonyl; arylalkylcarbonyl; alkyloxycarbonylalkylcarbonyl; arylcarbonyl; alkyloxycarbonyl; aryloxycarbonyl; arylalkyloxycarbonyl; mono- or di(alkyl)aminocarbonyl; mono- or di(aryl)aminocarbonyl; mono-or di (aryl-alkyl)aminocarbonyl; mono- or di(alkyloxycarbonylalkyl)aminocarbonyl; alkyloxyalkylaminocarbonyl; mono-, di- or tri(alkyl)amidino; mono-, di- or tri(aryl)amidino; mono-, di- or tri(arylalkyl)amidino; alkylsulphonyl; arylalkylsulphonyl or arylsulphonyl;

aryl is phenyl or naphthyl; each radical optionally substituted with 1, 2 or 3 substituents selected from the group of halo, nitro, cyano, hydroxy, alkyloxy or alkyl;

alkyl represents a straight or branched saturated hydrocarbon radical having from 1 to 10 carbon atoms, a cyclic saturated hydrocarbon radical having from 3 to 8 carbon atoms or a saturated hydrocarbon radical containing a straight or branched moiety having from 1 to 10 carbon atoms and a cyclic moiety having from 3 to 8 carbon atoms, optionally substituted with one or more halo, cyano, oxo, hydroxy, formyl, carboxyl or amino radicals; and halo represents fluoro, chloro, bromo and iodo.

2. A compound according to claim 1, wherein A and B are each benzo, optionally substituted with fluoro.

3. A compound according to claim 1 wherein C is a group of formula (c-1) or (c-2); wherein $Y^1$ is S; S(=O); S(=O)$_2$ or NR$^{10}$; wherein R$^{10}$ is selected from the group of hydrogen, cyano, alkyl, alkyloxyalkyl, formyl, alkylcarbonyl, alkyloxycarbonyl and alkyloxyalkylcarbonyl;

adjacent R$^{10}$ and R may form together a bivalent radical (e-1), (e-2) or (e-3); each radical optionally substituted by one or more substituents selected from oxo, thioxo, alkyl and alkylthio; and $_R12$ is hydrogen.

4. A compound according to claim 1, wherein C is a group of formula (c-3) or (c-4); wherein $Y^2$ is O;

$R^{12}$ is hydrogen;

$R^{13}$ is hydrogen; and $R^{14}$ is hydrogen; hydroxy, oxo or a group of formula (d-1).

5. A compound according to claim 1, wherein (d-1) is defined as in claim 1, wherein:

n is zero or 1;

$R^1$ and $R^2$ each independently are hydrogen; alkyl or alkyloxycarbonylalkyl; or $R^1$ and $R^2$ taken together with the nitrogen atom to which they are attached may form a radical of formula (a-3), (a-5) or (a-6); wherein :

p is zero or 1;

q is 1;

m is 1;

each $R^3$ independently is selected from the group of hydrogen and hydroxy; and $R^4$ is alkyl.

6. A compound according to claim 1, wherein:

i and j are integers, independently from each other, equal to zero or 1;

A and B are, each independently from each other, benzo, optionally substituted with fluoro;

each $R^9$ is, independently from each other, selected from the group of hydrogen and halo;

X represents O;

C is a group of formula (c-1), (c-2), (c-3) or (c-4); wherein $Y^1$ is S; S(=O); S(=O)$_2$ or NR$^{10}$; wherein R$^{10}$ is selected from the group of hydrogen, cyano, alkyl, alkyloxyalkyl, formyl, alkylcarbonyl, alkyloxycarbonyl and alkyloxyalkylcarbonyl;

$Y^2$ is O;

adjacent R$^{10}$ and R$^{11}$ may form together a bivalent radical (e-1), (e-2) or (e-3); each radical optionally substituted by one or more substituents selected from oxo, thioxo, alkyl and alkylthio;

$R^{12}$ is hydrogen;

$R^{13}$ is hydrogen;

$R^{14}$ is hydrogen, hydroxy, oxo or a group of formula (d-1)

$R^{11}$ is a group of formula (d-1); wherein :

n is zero or 1;

$R^1$ and $R^2$ each independently are hydrogen; alkyl or alkyloxycarbonylalkyl; or $R^1$ and $R^2$ taken together with the nitrogen atom to which they are attached may form a radical of formula (a-3), (a-5) or (a-6); wherein:

p is zero or 1;

q is 1;

m is 1;

each $R^3$ independently is selected from the group of hydrogen and hydroxy; and $R^4$ is alkyl.

7. A compound according to claim 1, wherein the hydrogen atoms on carbon atoms 3a and 12b have a trans configuration and those having the (2α, 3aα, 12bβ) stereochemical configuration.

8. A compound according to claim 1, wherein the compounds have the formulate

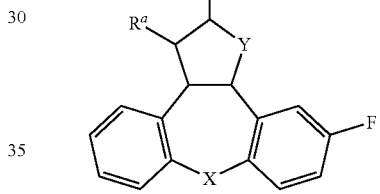

and are compounds selected from the compounds with the substitutions shown in the table below:

| X | Y | ---R$^a$ | ---R$^b$ | Stereochemical/ salt data |
|---|---|---|---|---|
| —O— | NH | ----H | ![CH2N(CH3)2] | 2R,3aR,12bS |
| —O— | NH | ----H | ![CH3, N, CH2CH2OH] | 2R,3aR,12bS |
| —O— | NH | ----H | ![piperazine-CH2CH2OH] | 2R,3aR,12bS. |

9. A pharmaceutical composition comprising a pharmaceutically acceptable carrier and, as active ingredient, a therapeutically effective amount of a compound according to claim 1.

* * * * *